US011324697B2

(12) United States Patent
Puder et al.

(10) Patent No.: US 11,324,697 B2
(45) Date of Patent: May 10, 2022

(54) METHODS AND COMPOSITIONS RELATING TO EMULSIONS COMPRISING FISH OIL AND/OR OMEGA-3 FATTY ACIDS

(71) Applicant: THE CHILDREN'S MEDICAL CENTER CORPORATION, Boston, MA (US)

(72) Inventors: Mark Puder, Medfield, MA (US); Kathleen Marie Gura, Norfolk, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 110 days.

(21) Appl. No.: 16/634,194

(22) PCT Filed: Aug. 10, 2018

(86) PCT No.: PCT/US2018/046206
§ 371 (c)(1),
(2) Date: Jan. 27, 2020

(87) PCT Pub. No.: WO2019/032959
PCT Pub. Date: Feb. 14, 2019

(65) Prior Publication Data
US 2020/0345638 A1 Nov. 5, 2020

Related U.S. Application Data

(60) Provisional application No. 62/543,437, filed on Aug. 10, 2017.

(51) Int. Cl.
*A61K 9/107* (2006.01)
*A23L 33/11* (2016.01)
*A23L 33/115* (2016.01)
*A23L 33/15* (2016.01)
*A23L 33/00* (2016.01)
*A61K 31/202* (2006.01)
*A61K 31/23* (2006.01)
*A61K 31/355* (2006.01)
*A61K 35/60* (2006.01)
*A61K 9/00* (2006.01)

(52) U.S. Cl.
CPC .............. *A61K 9/107* (2013.01); *A23L 33/11* (2016.08); *A23L 33/115* (2016.08); *A23L 33/15* (2016.08); *A23L 33/40* (2016.08); *A61K 31/202* (2013.01); *A61K 31/23* (2013.01); *A61K 31/355* (2013.01); *A61K 35/60* (2013.01); *A61K 9/0019* (2013.01)

(58) Field of Classification Search
CPC ...... A61K 9/107; A61K 31/202; A61K 31/23; A61K 31/355; A61K 35/60; A61K 9/0019; A23L 33/11; A23L 33/115; A23L 33/15; A23L 33/40

See application file for complete search history.

(56) References Cited

U.S. PATENT DOCUMENTS

| | | | |
|---|---|---|---|
| 4,820,731 A | 4/1989 | Masciolo et al. | |
| 5,434,183 A | 7/1995 | Larsson-Backstrom et al. | |
| 5,723,283 A | 3/1998 | Classen | |
| 5,874,470 A | 2/1999 | Nehne et al. | |
| 8,241,672 B2 * | 8/2012 | Driscoll | A61K 9/0019 424/523 |
| 9,034,389 B2 | 5/2015 | Driscoll | |
| 9,144,562 B2 | 9/2015 | Deckelbaum | |
| 9,566,260 B2 | 2/2017 | Puder et al. | |
| 9,629,821 B2 | 4/2017 | Puder et al. | |
| 9,861,605 B2 | 1/2018 | Driscoll | |
| 2003/0068385 A1 | 4/2003 | Moyer et al. | |
| 2014/0099345 A1 | 4/2014 | Deckelbaum et al. | |
| 2014/0120171 A1 | 5/2014 | Driscoll | |
| 2015/0011515 A1 | 1/2015 | Kaspar et al. | |
| 2015/0246013 A1 | 9/2015 | Driscoll | |

FOREIGN PATENT DOCUMENTS

| | | |
|---|---|---|
| EP | 0311091 A1 | 4/1989 |
| EP | 0567653 A1 | 11/1993 |
| EP | 0298293 B1 | 3/1994 |
| WO | 1997019683 A1 | 6/1997 |
| WO | 2003009828 A1 | 2/2003 |
| WO | 2003092395 A1 | 11/2003 |
| WO | 2005046669 A1 | 5/2005 |

(Continued)

OTHER PUBLICATIONS

Buchman et al., "Choline Deficiency Causes Reversible Hepatic Abnormalities in Patients Receiving Parenteral Nutrition: Proof of a Human Choline Requirement: A Placebo-Controlled Trial", Journal of Parenteral and Enteral Nutrition 25(5):260-267 (2001).
Buchman et al., "Choline Deficiency: A Cause of Hepatic Steatosis During Parenteral Nutrition That Can Be Reversed with Intravenous Choline Supplementation", Hepatology 22(5):1399-1403 (1995).
Buchman et al., "Lecithin Increases Plasma Free Choline and Decreases Hepatic Steatosis in Long-Term Total Parenteral Nutrition Patients", Gastroenterology 102:1363-1370 (1992).
Buchman et al., "Parenteral Nutrition-Associated Liver Disease and the Role for Isolated I Intestine and Intestine/Liver Transplantation", Hepatology 43(1)9-19 (2006).

(Continued)

*Primary Examiner* — Shirley V Gembeh
(74) *Attorney, Agent, or Firm* — Nixon Peabody LLP; David S. Resnick; Nicole D. Kling

(57) ABSTRACT

Described herein are emulsion compositions comprising fish oil and medium-chain triglycerides (MCT) and/or omega-3 fatty acids and medium-chain triglycerides (MCT). In some embodiments, the compositions further comprise, e.g., alpha-tocopherol, or one or more fatty acids. Further provided herein are methods of using the compositions, e.g., to provide nutrion, e.g., parenteral nutrition to a subject and/or to treat or prevent certain conditions described herein.

26 Claims, 24 Drawing Sheets

(56) References Cited

FOREIGN PATENT DOCUMENTS

| WO | 2010104575 A2 | 9/2010 |
|---|---|---|
| WO | 2011091019 A1 | 7/2011 |
| WO | 2016040570 A2 | 3/2016 |

OTHER PUBLICATIONS

Carlson et al., "First Year Growth of Preterm Infants Fed Standard Compared to Marine Oil n-3 Supplemented Formula", Lipids 27:901-907 (1992).
Cavicchi et al., "Prevalence of Liver Disease and Contributing Factors in Patients Receiving Home Parenteral Nutrition for Permanent Intestinal Failure." Ann Intern Med. 132:525-532 (2000).
Chao et al., "Effects of Parenteral Infusion with Fish-Oil or Safflower-Oil Emulsion on Hepatic Lipids, Plasma Amino Acids and Inflammatory Mediators in Septic Rats", Nutrition 16:284-288 (2000).
Chen et al., "Effects of dietary supplementation with fish oil on prostanoid metabolism during acute coronary occlusion with or without reperfusion in diet-induced hypercholesterolemic rabbits", Int. J. of Cardiology 36:297-304 (1992).
Chen et al., "Effects of fat emulsions with different fatty acid composition on plasma and hepatic lipids in rats receiving total parenteral nutrition." Clinical Nutrition 15:24-28 (1996).
Chen et al., "Effects offish oil in parenteral nutrition." Nutrition 19:275-279 (2003).
Colomb et al., "Role of Lipid Emulsions in Cholestatsis Associated with Long-Term Parenteral Nutrition in Children", Journal of Parenteral and Enteral Nutrition 24(6):345-350 (2000).
Cooke, Robert, "How fish oil may have saved babies' lives", Boston Globe, Jul. 3, 2006 edition.
Cooke, Robert, Newsday, Jan. 23, 2007. ALIVE, Thanks to Liver Treatment.
Driscoll "Regarding A Comparison of Fish Oil Sources for Parenteral Lipid Emulsions in a Murine Model" Journal of Parenteral and Enteral Nutrition 41(5):1703-705 (2017).
Fell et al. "Response to Driscoll" Journal of Parenteral and Enteral Nutrition 41(5):1704-705 (2017).
Fell et al., "A comparison offish oil sources for parenteral lipid emulsions in a murine model." Journal of Parenteral and Enteral Nutrition 41(2):1181-187 (2017).
Gura et al., "Safety and Efficacy of a Fish Oil-Based Fat Emulsion in the Treatment of Parenteral Nutrition-Associated Liver Disease" manuscript pp. 1-24.
Illingworth et al., "Inhibition of Low Density Lipoprotein Synthesis by Dietary Omega-3 Fatty Acids in Humans", Arteriosclerosis 493:1270-275 (1984).
Kaufman, "Prevention of parenteral nutriotion-associated liver disease in children", Pedriatric Transplantation 6(1):137-42 (2002).
Kohl et al., "Influence of Different Intravenous Lipid Emulsions on Hepatobiliary Dysfunction in a Rabbit Model", Journal of Pediatric Gastroenterology and Nutrition 441237-244 (2007).
La Scala et al., "The Addition of Lipids Increase the Total Parenteral Nutrition-Associated Cholestasis in the Rat." Eur. J Pediatr. Surg. 3 224-227 (1993).
Marcus, Amy Dockser, The Wall Street Journal Online, Nov. 13, 2006. "Different Rx: A Doctor's Push for Drug Pits Him Against Its Maker." Accessed Dec. 12, 2006 at 12:01am.
Muto et al., "Supplemental Parenteral Vitamin E Into Conventional Soybean Lipid Emulsion Does Not Prevent Parenteral Nutrition—Associated Liver Disease in Full-Term Neonatal Piglets." Journal of Parenteral and Enteral Nutrition 41(4):1575-582 (2017).
Nagakura et al., "Dietary supplementation with fish oil rich in omega-3 polyunsaturated fatty acids in children with bronchial asthma", Eur Respir J.16(5):861-865 (2000).
National Institute of Health (NIH) Guidelines, "Fish Oil" (2010).
Ng et al., "Vitamin E in new-generation lipid emulsions protects against parenteral nutrition-associated liver disease in parenteral nutrition-fed preterm pigs." Journal of Parenteral and Enteral Nutrition 40(5):656-671 (2016).
Omegaven Manufacturer Sheet.
Quigley et al., "Hepatobiliary Complications of Total Parenteral Nutrition", Gastroenterology 104(1):286-301 (1993).
Quinn. "Comparing rat's to human's age: how old is my rat in people years?", Nutrition 21(6):775-777 (2005).
Quiros-Tejeira et al., Long Term Parenteral Nutritional Support and Intestinal Adaptation in Children with Short Bowel Syndrome: A 25 year Experience, The Journal of Pediaticts 145:157-163 (2004).
Roth et al., "Lipid deposition in Kupffer cells after parenteral fat nutrition in rats: a biochemical and ultrastructural study", Intensive Care Med. 22:1224-1231 (1996).
Saboori et al., "Effect of vitamin E supplementation on serum C-reactive protein level: a meta-analysis of randomized controlled trials" European Journal of Clinical Nutrition 69(8):867-873 (2015).
Shing et al., "Effect of tocopherol on atherosclerosis, vascular function, and inflammation in apolipoprotein E knockout mice with subtotal nephrectomy." Cardiovascular therapeutics 32(6):270-275 (2014).
Simopoulos, "Omega-3 Fatly Acids in Inflammation and Autoimmune Diseases", JACN 21(6):495-505 (2002).
Stedman's Medical Dictionary 27th Edition, Lippincott Williams and Wilkins, 2000.
Teitelbaum et al., "Use of cholecystokinin-octapeptide for the prevention of Parenteral Nutrition-Associated Cholestasis", Pediatrics 115:1132-1340 (2005).
Van Aerde et al., "Intravenous fish oil emulsion attenuates total parenteral nutrition-induced cholestasis in newborn piglets" Pediatric Research 45(2):202-208 (1999).
Yeh et al., "Effects of fish oil and safflower oil emulsions on diet-induced hepatic steatosis in rats receiving total parenteral nutrition." Clinical Nutrition 15(2):80-83 (1996).
Yeh et al., "Effects of n-3 and n-6 fatty acids on plasma eicosanoids and liver antioxidant enzymes in rats receiving total parenteral nutrition" Nutrition 13 (1):32-36 (1997).
Grimm. "A balanced lipid emulsion—A new concept in parenteral nutrition." Clinical Nutrition Supplements 1(3): 25-30 (005).

* cited by examiner

*p < 0.003 compared to chow
p < 0.006 compared to FO

*p < 0.05 compared to chow

*p < 0.05 compared to PN FO

Phytosterols and Alpha-tocopherol Levels in Emulsions

| Emulsion | Phytosterols (mg/L) | Alpha-Tocopherol (mg/L) |
|---|---|---|
| OM | 10 | 193 |
| IL | 570 | 12 |
| FO | 46 | 133 |
| FO+P | 424 | 129 |
| SO | 461 | 7 |
| SO+AT | 446 | 164 |

Emulsion USP <729> Particle Size Analysis

| Emulsion | Mean Globule Size (nm) | PFAT5 (%) |
|---|---|---|
| FO | 238.7 | 0.032 |
| FO+P | 242.3 | 0.015 |
| SO | 252.8 | 0.009 |
| SO+AT | 252.8 | 0.013 |

*FIG. 18*

METHODS AND COMPOSITIONS RELATING TO EMULSIONS COMPRISING FISH OIL AND/OR OMEGA-3 FATTY ACIDS

CROSS-REFERENCE TO RELATED APPLICATIONS

This application is a 35 U.S.C. § 371 National Phase Entry Application of International Application No. PCT/US2018/046206 filed Aug. 10, 2018, which designates the U.S. and claims benefit under 35 U.S.C. § 119(e) of U.S. Provisional Application No. 62/543,437 filed Aug. 10, 2017, the contents of which are incorporated herein by reference in their entireties.

GOVERNMENT SUPPORT

This invention was made with government support under Grant Nos. 1F32DK104525-01; 5T32HL007734-22; and T35HL110843 awarded by the National Institutes of Health. The government has certain rights in the invention.

TECHNICAL FIELD

The technology described herein relates to lipid emulsions for administration to patients, e.g., orally or parenterally.

BACKGROUND

Long-term and short-term PN-dependent patients can be vulnerable to inflammatory insults. For long-term PN-dependent patients, chronic disease states and a long-term indwelling central venous catheter for the delivery of PN can precipitate a pro-inflammatory state. Short-term PN-dependent patients, such as trauma patients, post-operative patients, and acutely ill patients requiring an intensive care unit, are also subject to pro-inflammatory challenges.

In addition to the use of PN itself, the particular lipid emulsion administered via PN can modulate the inflammatory response and affect the inflammatory status of PN-dependent patients. Soybean oil-based lipid emulsions are rich in pro-inflammatory omega-6 fatty acids while fish oil lipid emulsions contain an abundance of the more anti-inflammatory omega-3 fatty acids. Fish oil lipid emulsions have been utilized to treat parenteral nutrition-associated liver disease (PNALD) in patients, a condition characterized by hepatic inflammation and cholestasis.

SUMMARY

Development of lipid emulsions which further lower the risk of developing inflammatory responses and/or liver disease can improve the treatment of a number of patients for whom normal nutritional intake is not recommended or adequate. As described herein, the inventors have found that mixed emulsions of a) MCTs and b) fish oil and/or omega-3 fatty acids (e.g., omega-3 predominate fatty acid oil) provide improved anti-inflammatory performance over fish oil or MCTs alone. Further described herein is the surprising efficacy obtained with particular ratios of a) MCTs and b) fish oil and/or omega-3 fatty acids (e.g., omega-3 predominate fatty acid oil).

In particular, it is demonstrated herein that mixed emulsions of FO and MCT provide improved anti-inflammatory benefit in response to an inflammatory stimulus compared to FO alone. In particular, mixtures between ratios of 30:70 to 70:30 provided a suprisingly improved balance of hepatic protection and blunting of the inflammatory response as compared to less balanced mixtures. The ratio of 50:50 was surprisingly optimal in providing such effects. As used herein, ratios of MCT to fish oil or omega-3 fatty acids relative to each other are provided in w/w units. The w/v amount of MCT, fish oil, and/or omega-3 fatty acids in the present compositions are described elsewhere herein.

Furthermore, many prior art formulations explicitly require vegetable oils, as their developers believe that a lack of vegetable oils will result in essential fatty acid deficiency (EFAD) (see, e.g., US Patent Publication 2010/0233280). In contrast, embodiments of the formulations and methods described herein do not comprise of vegetable oil and are not predominately omega-6 fatty acids and yet do not induce EFAD, despite the statements of experts that such an outcome would result.

In one aspect of any of the embodiments, described herein is an emulsion composition comprising: a combination of fish oil and medium-chain triglycerides (MCT) at a ratio of about 30:70 to about 70:30; or a combination of omega-3 fatty acids and medium-chain triglycerides (MCT) at a ratio of about 30:70 to about 70:30. In one aspect of any of the embodiments, described herein is an emulsion composition comprising: a combination of fish oil and medium-chain triglycerides (MCT) or a combination of omega-3 fatty acids and MCTs at a ratio between, but not inclusive of, 30:70 and 70:30. In some embodiments of any of the aspects, the composition comprises a combination of fish oil and medium-chain triglycerides (MCT) at a ratio of about 40:60 to about 60:40; or a combination of omega-3 fatty acids and medium-chain triglycerides (MCT) at a ratio of about 40:60 to about 60:40. In some embodiments of any of the aspects, the composition comprises a combination of fish oil and medium-chain triglycerides (MCT) at a ratio of about 50:50; or a combination of omega-3 fatty acids and medium-chain triglycerides (MCT) at a ratio of about 50:50. In some embodiments of any of the aspects, the composition comprises a combination of fish oil and medium-chain triglycerides (MCT) at a ratio of 50:50; or a combination of omega-3 fatty acids and medium-chain triglycerides (MCT) at a ratio of 50:50. In some embodiments of any of the aspects, the composition the omega-3 fatty acids are provided as an omega-3 predominate fatty acid oil. In some embodiments of any of the aspects, the composition the omega-3 fatty acids are provided as an omega-3 predominate fatty acid oil which has not undergone re-esterification.

As used herein, "omega-3 predominant fatty acid oil" refers to a fatty acid oil which comprises a greater proportion of omega-3 fatty acids than omega-6 fatty acids. In some embodiments of any of the aspects, the fatty acids in an omega-3 predominant fatty acid oil are more than 50%, e.g., more than 50%, more than 60%, more than 70%, more than 80%, more than 90%, more than 95%, or more than 98% omega-3 fatty acids (foregoing percentages are % of fatty acids in the fatty acid oil by weight).

In some embodiments of any of the aspects, the composition further comprises alpha-tocopherol. In some embodiments of any of the aspects, the alpha-tocopherol is present at a level of at least 100 mg/L of the entire composition. In some embodiments of any of the aspects, the alpha-tocopherol is present at a level of at least 120 mg/L. In some embodiments of any of the aspects, the emulsion composition comprises alpha-tocopherol and other forms of vitamin E (e.g., beta tocopherol, gamma tocopherol, delta tocopherol, alpha tocotrienol, beta tocotrienol, gamma tocotrienol, and/or delta tocotrienol) at a ratio of at least 2:1 by weight in the entire composition. In some embodiments of any of the aspects, the emulsion composition comprises alpha-tocopherol and other forms of vitamin E at a ratio of at least 10:1. In some embodiments of any of the aspects, the emulsion composition does not comprise forms of vitamin E other than alpha-tocopherol.

In some embodiments of any of the aspects, phytosterols are not present in the composition. In some embodiments of any of the aspects, phytosterols are present in the composition. In some embodiments of any of the aspects, phytosterols are present in the composition at a concentration of less than 50 mg/L. Phytosterols can include plant sterols and plant stanols, e.g., beta-sitosterol, campesterol, stigmasterol, ergosterol, sitostanol, campestanol, avenasterol, and/or stigmastanol.

In some embodiments of any of the aspects, arachidonic acid is present in the composition at a concentration of at least 900 mg/L. In some embodiments of any of the aspects, docosahexaenoic acid is present in the composition at a concentration of at least 13.4 g/L. In some embodiments of any of the aspects, eicosapentaenoic acid is present in the composition at a concentration of at least 11.6 g/L.

In some embodiments of any of the aspects, the composition is formulated for oral administration. In some embodiments of any of the aspects, the composition is formulated for parenteral or intravenous administration. In some embodiments of any of the aspects, the composition further comprises an additive of one or more additional fatty acids or a mixture thereof. In some embodiments of any of the aspects, the additive comprises one or more fatty acids which are therapeutic for a disease.

In one aspect of any of the embodiments, described herein is a method comprising administering an emulsion formulation as described herein to a subject in need thereof. In some embodiments of any of the aspects, the administration is parenteral administration. In some embodiments of any of the aspects, the administration is total parenteral administration. In some embodiments of any of the aspects, the administration is oral administration. In some embodiments of any of the aspects, the subject is a subject in need of treatment or prevention of a condition selected from the group consisting of: hepatic steatosis; intestinal failure; parenteral nutrition-associated liver disease (PNALD); sepsis; cystic fibrosis; sickle cell anemia; pancreatitis; inflammatory bowel disease; Crohn's disease; biliary atresia; primary sclerosis cholangitis; an inflammatory infection; an inflammatory condition; systemic inflammatory response syndrome (SIRS); hypertriglyceridemia; severe hypertriglyceridemia; severe hepatic steatosis; retinopathy of prematurity; acute tubular necrosis; IgA nephropathies; ischemia-reperfusion injury; traumatic brain injury; multisystem organ failure; respiratory distress syndrome; acute myocardial infarction; myocardial infarction; status anginosus; status asthmaticus; status epilepticus; status lacunaris; inflammatory bowel disease; regional enteritis; ulcerative colitis; severe or debilitating arthritis; arthritis; psoriasis; severe psoriasis; burns; third degree burns; pancreatitis; acute pancreatitis; intestinal failure associated liver disease (IFALD), parenteral nutrition associated cholestasis (PNAC), essential fatty acid deficiency (EFAD), parenteral nutrition dependency complicated by soy allergy or allergy to lipid emulsions comprising ingredients other than MCTs and fish oil and/or omega-3 fatty acids. In some embodiments of any of the aspects, the subject is a subject in need of treatment or prevention of parenteral nutrition-associated liver disease (PNALD).

In some embodiments of any of the aspects, the subject is in need of parenteral nutrition. In some embodiments of any of the aspects, the subject is in need of total parenteral nutrition. In some embodiments of any of the aspects, the patient does not receive oral nutrition. In some embodiments of any of the aspects, the patient does not receive other parenteral formulations. In some embodiments of any of the aspects, the patient does not receive oral nutrition which is sufficient to maintain a nutritional balance. In some embodiments of any of the aspects, the patient does not receive other parenteral formulations which are sufficient to maintain a nutritional balance. In some embodiments of any of the aspects, the patient does not receive other topical formulations which are sufficient to maintain a nutritional balance. In some embodiments of any of the aspects, the patient does not receive other nutritional sources of fatty acids. In some embodiments of any of the aspects, the patient does not receive other parenteral nutritional sources of fatty acids. In some embodiments of any of the aspects, the patient does not receive other nutritional sources of essential fatty acids. In some embodiments of any of the aspects, the patient does not receive other parenteral nutritional sources of essential fatty acids.

In some embodiments of any of the aspects, the emulsion formulation is administered as a monotherapy. In some embodiments of any of the aspects, the emulsion formulation is administered as a monotherapy for therapeutic benefit. In some embodiments of any of the aspects, the emulsion formulation is administered as a monotherapy for nutritional needs.

In some embodiments of any of the aspects, the patient is a patient in need of treatment for a condition selected from the group consisting of: hepatic steatosis; intestinal failure; parenteral nutrition-associated liver disease (PNALD); sepsis; cystic fibrosis; sickle cell anemia; pancreatitis; inflammatory bowel disease; Crohn's disease; biliary atresia; primary sclerosis cholangitis; an inflammatory infection; an inflammatory condition; systemic inflammatory response syndrome (SIRS); hypertriglyceridemia; severe hypertriglyceridemia; severe hepatic steatosis; retinopathy of prematurity; acute tubular necrosis; IgA nephropathies; ischemia-reperfusion injury; traumatic brain injury; multisystem organ failure; respiratory distress syndrome; acute myocardial infarction; myocardial infarction; status anginosus; status asthmaticus; status epilepticus; status lacunaris; inflammatory bowel disease; regional enteritis; ulcerative colitis; severe or debilitating arthritis; arthritis; psoriasis; severe psoriasis; burns; third degree burns; pancreatitis; acute pancreatitis; intestinal failure associated liver disease (IFALD), parenteral nutrition associated cholestasis (PNAC), essential fatty acid deficiency (EFAD), parenteral nutrition dependency complicated by soy allergy or allergy to lipid emulsions comprising ingredients other than MCTs and fish oil and/or omega-3 fatty acids.

In some embodiments of any of the aspects, the dose administered is from about 0.5 g total fatty acids in the emulsion/kg/day to about 5 g total fatty acids in the emulsion/kg/day. In some embodiments of any of the aspects, the dose administered is from about 1 g total fatty acids in the emulsion/kg/day to about 3 g total fatty acids in the emulsion/kg/day. In some embodiments of any of the aspects, the dose administered is about 2 g total fatty acids in the emulsion/kg/day. In the foregoing doses, "kg" refers to the mass of the subject being administered the composition. In some embodiments of any of the aspects, the method further comprises administering an additive of one or more additional fatty acids or a mixture thereof.

BRIEF DESCRIPTION OF THE DRAWINGS

FIG. 2A: No group that received a fat source developed biochemical EFAD, only the PN-fed group receiving saline developed EFAD. *=p<0.05 compared to chow. FIG. 2B: SO and SO+AT contain more omega-6 fatty acids than FO-treated groups. *=p<0.05 compared to FO. FIG. 2C: FO and FO+P contain more omega-3 fatty acids compared to SO-treated groups. 8=p<0.05 compared to FO. All statistical analysis performed with single-factor ANOVA.

FIG. 5A: Western blot images for ACC, PPARg, and the housekeeping gene beta-actin. FIG. 5B: Quantification of protein expression for each group, normalized to beta-actin and compared to chow.

FIG. 11A: Body masses were monitored every other day over the course of the PN regimen with no statistical differences in growth between groups. Liver (FIG. 11B), spleen (FIG. 11C), and right kidney (FIG. 11D) masses at euthanasia after 19 days of the PN diet. There were no differences in organ masses between groups. N=10 mice per treatment group. Statistical analysis was with one-way ANOVA.

FIG. 12A: Triene to tetraene ratios. Only mice receiving no fat source (PN+saline) met biochemical criteria for EFAD. Distribution of the principle omega-6 fatty acids (FIG. 12B) and omega-3 fatty acids (FIG. 12C) reflect the fat source administered to each group. N=3 samples per treatment group randomly selected. Statistical analysis was with one-way ANOVA.

FIG. 15C: Western Blot image.

FIG. 16 demonstrates that fat emulsions formulated in the laboratory recapitulate the effects of similar commercially available intravenous fat emulsions in a murine model of PN-induced liver injury. Fat-free PN results in the development of steatosis over 19 days (bottom left panel). FO formulated in the laboratory (PN+FO) and commercially available FO emulsion (OM) preserve normal hepatic architecture with the PN diet, while SO formulated in the laboratory (PN+SO) and commercially available SO (IL) do not.

FIG. 17 and FIG. 18 depict tables of content and particle size of the fat emulsions used in Example 3.

DETAILED DESCRIPTION

Figure 1A:
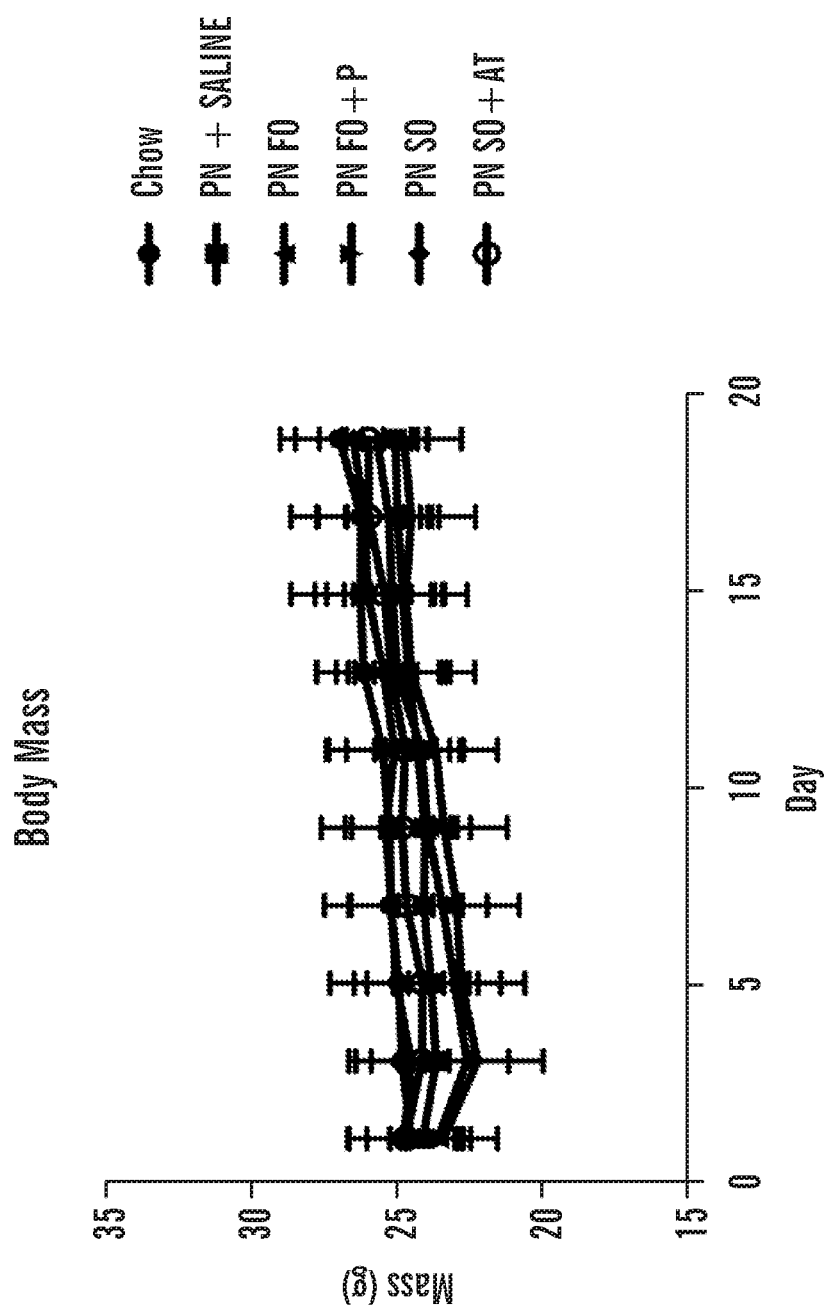
FIGS. 1A-1B demonstrate that there are no differences in growth (FIG. 1A) or in organ masses (FIG. 1B) between treatment groups. N=9-10 mice per group, statistical analysis single-factor ANOVA.

As described herein, the inventors have discovered that particular emulsions of a) fish oil or omega-3 fatty acids and b) medium-chain trigylcerides (MCTs), provide surprising efficacy as a nutritional source and perform better, e.g., in preventing and reducing inflammatory responses, than either of the components alone. Additionally, the emulsions described herein have improved stability. Finally, in contrast to earlier work in this area, the emulsions described herein do not induce essential fatty acid deficiency and can be used as a monotherapy with respect to nutritional fat sources for a patient. In one aspect of any of the embodiments, described herein is an emulsion composition comprising a) a combination of fish oil and medium-chain triglycerides (MCT) at a ratio of about 70:30 to about 30:70; or b) a combination of omega-3 fatty acids and medium-chain triglycerides (MCT) at a ratio of about 70:30 to about 30:70.

As used herein, the term "emulsion" refers to a heterogeneous system comprising at least two or more substantially immiscible liquids, wherein one liquid is dispersed in another liquid in the form of droplets. By way of example only, emulsions can be biphasic systems comprising two immiscible liquid phases intimately mixed and dispersed with each other. Examples of an emulsion include, but are not limited to, water-in-oil emulsions, oil-in-water emulsion, water-in-water, water-in-oil-in-water emulsions, and oil-in-water-in-oil emulsions. In some embodiments of any of the aspects, the continuous phase of the emulsion is water.

In some embodiments of any of the aspects, the emulsion comprises water. In some embodiments, the emulsion is about 20% total fats in water by weight/volume. In some embodiments, the emulsion is from about 10% total fats in water by weight/volume to about 50% total fats in water by weight/volume. In some embodiments, the emulsion is about 20% total fats in water by weight/volume. In some embodiments, the emulsion is from 10% total fats in water by weight/volume to 50% total fats in water by weight/volume.

Emulsions are generally unstable mixtures and do not form spontaneously, thus, in order to mix the continuous and dispersed phases and form the emulsion, an energy input is required. This energy can be applied, for example, by shaking, stirring, homogenizing, spray processing, high pressure pumping and ultrasonic emulsification. The emulsion formulation described herein can be made by blending the fat components listed herein with any proteins, carbohydrates, and/or other additional additives, and homogenizing the mixture into a stable emulsion. In some embodiments of any of the aspects, the both the MCT and the fish oil and/or omega-3 fatty acids are emulsified, e.g., not merely mixed or mixed into an emulsion of the other. Over time however, the emulsion formed may tend to revert to the stable state of separate oil and aqueous layers. Accordingly, in some embodiments, the emulsion formulation described herein can further comprise any natural or synthetic emulsifier known in the art. The addition of an emulsifier can increase the kinetic stability of emulsions so that, once formed, the emulsion does not change significantly in long term storage.

Emulsion as described herein can be prepared by a number of conventional techniques known to those skilled in the art. For example, the core lipid(s) are first mixed with one or more emulsifiers and the antioxidant, if one is being used. The emulsion is then prepared by slowly adding this oil phase into water with constant agitation. If an osmolality modifier is being used, it is added to the water prior to mixture with the oil phase. The pH can be adjusted at this stage, if necessary, and the final volume adjusted with water, if required.

In some embodiments of any of the aspects, the particle size of the oil globules in the emulsion, e.g., when formulated for parenteral administration are within or below the size range of the naturally occurring chylomicron, which is 0.4-1.0 um. If the particle size is larger than this, the lipid particles may be deposited in the liver, spleen and lungs resulting in significant fat load following infusion (Rahui C. M., et I al., Am. Hosp. Pharm. 1992, 49:2749-2755). Lipids with small particle sizes disperse better in the emulsion and tend to produce safer and more stable emulsions. Selection of appropriate conditions for the preparation of the emulsions according to the present invention is considered to be within the ordinary skills of a worker in the art.

In some embodiments, the emulsion is a stable emulsion. As used herein, the term "stable emulsion" refers to an emulsion in which droplets remain substantially evenly dispersed throughout a continuous phase (or a carrier liquid) for an extended time period (e.g., at least about 1 month or longer), including reasonable storage and usage times. For example, the droplets do not aggregate or settle out after an extended time period (e.g., at least about 1 month or longer).

As used herein, the term "substantially immiscible" refers to two or more liquids that do not form a homogenous mixture when they are in contact with each other. In some embodiments, when two or more substantially immiscible liquids are in contact with each other, one of the liquids can have a partial solubility (e.g., no more than 10% or lower) in another substantially immiscible liquid. The term "homogenous mixture" as used herein means that all components and/or liquids in a mixture are readily present in a single phase. For instance, one or more of the components and/or liquids do not separate into different phases even when the mixture is left stationary for an extended period of time (e.g., at least about 6 hours or longer, including, e.g., at least about 12 hours, at least about 18 hours, at least about 24 hours, or longer). When referring to miscibility of the droplets and the carrier liquid, the term "substantially immiscible" refers to a liquid (e.g., a thin liquid layer) forming at least the outer surface of the droplets and the carrier liquid that do not form a homogenous mixture when they are in contact with each other.

As used herein and throughout the specification, the term "droplet" refers to a finite volume of matter comprising at least one liquid or at least one liquid phase, including, e.g., at least two or more liquids or liquid phases. The droplets can be of any dimension, configuration, and/or shape. In some embodiments of various aspects described herein, the droplets can have a droplet size that is smaller (e.g., at least 50% smaller) than the inner diameter of a needle that is used to administer an emulsion comprising the droplets. It will be understood by one of ordinary skill in the art that droplets usually exhibit a distribution of droplet sizes around the indicated "size." Unless otherwise stated, the term "droplet size" or "size" as used herein refers to the mode of a size distribution of droplets, i.e., the value that occurs most frequently in the size distribution. Methods for measuring the droplet size are known to a skilled artisan, e.g., by dynamic light scattering (such as photo-correlation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments of any of the aspects, the emulsion formulation is about 10-50% emulsion, which means that the MCT and fish oil and/or omega-3 fatty acids described herein are present in an amount of about 10 g to about 50 g per 100 mL of the formulation. In some embodiments of any of the aspects, the emulsion formulation is about 20-40% emulsion.

In some embodiments of any of the aspects, the emulsion formulation is about 10-50% emulsion. In some embodiments of any of the aspects, the MCT and fish oil and/or omega-3 fatty acids described herein provide 1.1 kcal/mL to 5 kcal/mL of the formulation.

While the compositions for total enteral or parenteral nutrition described herein are intended to be administered as emulsions, other forms of the formulations are also encompassed by the invention. For example, the compositions described herein as emulsions can also be made in powder form by increasing the percent total solids in the formula, using procedures well known to those skilled in the art. The concentrate or powder can be reconstituted for feeding by adding water (tap or deionized-sterilized water) to form an emulsion.

As used herein, "fish oil" refers to an oil derived from a fish or fish tissue. Fish oil is available commercially, for example 10% (wt/wt) fish oil triglycerides can be obtained from Nisshin Flour Milling Co. located in Nisshin, Japan. OMEGAVEN (Fresnius Kabi) is suitable for use in the methods and compositions described herein. In some embodiments of any of the aspects, the fish oil can comprise omega-3 fatty acids, DHA, and/or EPA. In some embodiments of any of the aspects, a fish oil can be a fish oil derived from one or more cold-water fish, which are known for having high omega-3 fatty acid content. Non-limiting examples of cold water fish can include a deep-sea fish, shark, salmon, cod, salmon, bonito, mackerel, Atlantic mackerel, haddock, herring, mahi mahi, menhaden, mackerel, caplin, tilapia, pacific saury, krill, anchovies, pollock, trout, whitefish, tuna, smelt, shad, and sardines. In some embodiments of any of the aspects, a fish oil can be a fish oil derived from one or more saltwater cold-water fish. In some embodiments of any of the aspects, a fish oil can be a fish oil derived from shark, salmon, cod, salmon, bonito, mackerel, Atlantic mackerel, haddock, herring, mahi mahi, menhaden, mackerel, caplin, tilapia, pacific saury, krill, anchovies, pollock, trout, whitefish, tuna, smelt, shad, sardines, or any combination thereof.

As used herein, the term "fatty acid" includes fatty acids such as unsaturated (e.g., monounsaturated, polyunsaturated) or saturated fatty acids, as well as pharmaceutically-acceptable esters, free acids, mono-, di- and triglycerides, derivatives, conjugates, precursors, salts, and mixtures thereof.

As used herein, the term "omega-3 fatty acids" includes natural and synthetic omega-3 fatty acids, as well as pharmaceutically acceptable esters, free acids, triglycerides, derivatives, conjugates, precursors, salts, and mixtures thereof. Omega-3 fatty acids can include, but are not limited to, hexadecatrienoic acid (HTA); α-Linolenic acid (ALA); Stearidonic acid (SDA); Eicosatrienoic acid (ETE); Eicosatetraenoic acid (ETA); Eicosapentaenoic acid (EPA); Heneicosapentaenoic acid (HPA); Docosapentaenoic acid (DPA); Clupanodonic acid; Docosahexaenoic acid (DHA); Tetracosapentaenoic acid; and Tetracosahexaenoic acid (Nisinic acid). Omega-3 fatty acids for use in the emulsions described herein can have a high content of eicosapentaenoic acid (EPA) as well as docosahexaenoic acid (DHA). The omega-3-fatty acids may be from marine or synthetic origin. For example, a suitable source of omega-3 fatty acids is fish or seal oil. Suitable fish oil sources include deep-sea fish, shark, salmon, cod, salmon, bonito, mackerel, Atlantic mackerel, haddock, herring, mahi mahi, menhaden, mackerel, caplin, tilapia, pacific saury, krill, anchovies, pollock, trout, whitefish, tuna, smelt, shad, and sardines, cold-water fish as described elsewhere herein, and the like.

The fatty acid(s) according to the present disclosure may be derived from animal oils and/or non-animal oils. In some embodiments of the present disclosure, the fatty acid(s) are derived from at least one oil chosen from marine oil, algae oil, plant-based oil, and microbial oil. Marine oils include, for example, fish oil, such as tuna fish oil, krill oil, and lipid composition derived from fish. Plant-based oils include, for example, flaxseed oil, canola oil, mustard seed oil, and soybean oil. Microbial oils include, for example, products by Martek. In at least one embodiment of the present disclosure, the fatty acid(s) are derived from a marine oil, such as a fish oil. In at least one embodiment, the marine oil is a purified fish oil.

In some embodiments of any of the aspects, the omega-3 fatty acids of an emulsion described herein can comprise EPA, DHA, or a combination thereof. In some embodiments of any of the aspects, the omega-3 fatty acids of an emulsion described herein can consist essentially of EPA, DHA, or a combination thereof. In some embodiments of any of the aspects, the omega-3 fatty acids of an emulsion described herein can consist of EPA, DHA, or a combination thereof.

Examples of further omega-3 fatty acids (e.g., omega-3 predominate oils) and mixtures thereof encompassed by the present disclosure include the omega-3 fatty acids as defined in the European Pharmacopoeia Omega-3 Triglycerides, or the Fish oil rich in omega-3 acids monograph; which are incorporated by reference herein in their entireties. Examples of further omega-3 fatty acids (e.g., omega-3 predominate oils) and mixtures thereof encompassed by the present disclosure include the omega-3 fatty acids as defined in the European Pharmacopoeia Omega-3 Triglycerides, the European Pharmacopoeia Omega-3 acid Ethyl Esters 60, or the Fish oil rich in omega-3 acids monograph; which are incorporated by reference herein in their entireties.

Commercial examples of omega-3 fatty acids suitable for the present disclosure comprise different fatty acid mixtures (e.g., that can be in the form of triglycerides (TG), ethyl esters (EE), free fatty acid form (FA) and/or as phospholipids) including, but not limited to: Incromega™ omega-3 marine oil concentrates such as Incromega™ E1070, Incromega™ TG7010 SR, Incromega™ E7010 SR, Incromega™ TG6015, Incromega™ EPA500TG SR, Incromega™ E400200 SR, Incromega™ E4010, Incromega™ DHA700TG SR, Incromega™ DHA700E SR, Incromega™ DHA500TG SR, Incromega™ TG3322 SR, Incromega™ E3322 SR, Incromega™ TG3322, Incromega™ E3322, Incromega™ Trio TG/EE (Croda International PLC, Yorkshire, England); EPAX6000FA, EPAX5000FA, EPAX4510TG, EPAX2050TG, EPAX7010EE, EPAX5500EE, EPAX5500TG, EPAX5000EE, EPAX5000TG, EPAX6000EE, EPAX6000TG, EPAX6000FA, EPAX6500EE, EPAX6500TG, EPAX4510TG, EPAX1050TG, EPAX2050TG, EPAX 7010TG, EPAX7010EE, EPAX6015TG/EE, EPAX4020TG, and EPAX4020EE (EPAX is a wholly-owned subsidiary of Norwegian company Austevoll Seafood ASA); MEG-3® EPA/DHA fish oil concentrates (Ocean Nutrition Canada); DHA FNO "Functional Nutritional Oil" and DHA CL "Clear Liquid" (Lonza); Superba™ Krill Oil (Aker); omega-3 products comprising DHA produced by Martek; Neptune krill oil (Neptune); cod-liver oil products and anti-reflux fish oil concentrate (TG) produced by Mollers; Lysi Omega-3 Fish oil; Seven Seas Triomega® Cod Liver Oil Blend (Seven Seas); and Fri Flyt Omega-3 (Vesterålens).

The fish oil and/or omega-3 fatty acids used herein can be purified, e.g., to meet the quality standards for parenteral administration. In some embodiments of any of the aspects, the fish oil and/or omega-3 fatty acids can be enriched with additional or further omega-3 fatty acid triglycerides, e.g., purified or synthesized omega-3 fatty acid triglycerides from another source can be added to the fish oil and/or omega-3 fatty acids to increase the omega-3 fatty acid triglyceride content. Methods of extracting and refining oils are well known in the art. It is not necessary for the oils to undergo re-esterification in order to purify, extract, or refine them.

In some embodiments of any of the aspects, the fish oil and/or omega-3 fatty acids described herein can comprise from 0-100 percent DHA and 0-100 EPA.

In some embodiments of any of the aspects described herein, the omega-3 fatty acids and/or fish oil can be highly refined, e.g., highly enriched beyond the initial content of omega-3 fatty acids and their triglycerin compound as part of this specific procedure. In some embodiments of any of the aspects, these compositions can comprise a minimum of 95% weight, e.g., 96% weight, 97% weight, 98% weight or greater, of monomeric triglycerides. In some embodiments of any of the aspects, these compositions can comprise less than 1% weight percent of oxidized triglycerides, less than 0.2% weight percent of trimeric and oligomeric triglycerides and less than 0.8% weight percent of dimeric polyglycerides, and less than 1.5% weight, of unemulsifiable particularly carbohydrates and sterane. In some embodiments of any of the aspects, the total content of eicosapentaenoic acid and docosahexanoic acid in the fish oil and/or omega-3 fatty acids is from about 25%-50% weight. In some embodiments of any of the aspects, the total content of eicosapentaenoic acid and docosahexanoic acid in the fish oil and/or omega-3 fatty acids is from about 35%-50% weight. While fish oils generally can usually have a cholesterol content of 4000 to 12000 ppm, the cholesterol content of the fish oild and/or omega-3 fatty acids as used herein (e.g., after refinement or enrichment) comprise less than 2500 ppm, e.g., less than 1500 ppm.

In some embodiments of any of the aspects, the fish oil and/or omega-3 fatty acid of the compositions described herein are natural triglycerides, e.g., they have not been distilled or re-esterified. Distillation and/or re-esterification of trigylcerides is utilized in certain compositions known in the art (e.g., to remove mysristic or pamitoleic acids), but it is specifically contemplated herein that such procedures alter the triglycerides to induce toxicity therein and increase the presence of diglyceride, monoglyceride, and free fatty acids. In some embodiments of any of the aspects, the omega-3 fatty acids of the compositions described herein are triglycerides, e.g, they are not diglycerides as described elsewhere. For example, the omega-3 fatty acids of the compositions described herein can comprise no more than 10%, no more than 9%, no more than 8%, no more than 7%, no more than 6%, no more than 5%, no more than 4%, no more than 3%, no more than 2%, no more than 1%, or less, or no diglycerides, e.g., as a proportion of the total diglyceride+triglyceride content.

As used herein, "medium-chain triglycerides" or "MCT" refer to triglycerides having fatty acids of 6-12 carbon atom chains. MCT have saturated fatty acids. A triglyceride ("TG") (also known as triacylglycerol or triacylglyceride) is a glyceride in which the glycerol is esterified with three fatty acids. MCTs can comprise fatty acids selected from, e.g., caprylic acid, capric acid, lauric acid, and caproic acid. MCTs can be derived from a plant such as a fruit or vegetable, for example, a plurality of plants. The description of the MCT for use in this disclosure can, for example, meet the requirements of EP monograph 0868, entitled "Triglycerides, Medium Chain" (Triglycerida saturate media) (EP 0868, 2008); which is incorporated by reference herein in its entirety.

In some embodiments of any of the aspects, MCT can comprise 90% or more C8 and/or C10 fatty acids. In some embodiments of any of the aspects, MCT can comprise 95% or more C8 and/or C10 fatty acids. In some embodiments of any of the aspects, MCT can comprise 30%-50% C10 fatty acids and 45%-65% C8 fatty acids. In some embodiments of any of the aspects, MCT can comprise about 41% C10 fatty acids and about 54% C8 fatty acids.

In some embodiments of any of the aspects, the emulsion can comprise a) a combination of fish oil and medium-chain triglycerides (MCT) at a ratio of 70:30 to 30:70; or b) a combination of omega-3 fatty acids and medium-chain triglycerides (MCT) at a ratio of 70:30 to 30:70. In some embodiments of any of the aspects, the emulsion can comprise a) a combination of fish oil and medium-chain triglycerides (MCT) at a ratio of about 60:40 to about 30:70; or b) a combination of omega-3 fatty acids and medium-chain triglycerides (MCT) at a ratio of about 60:40 to about 30:70. In some embodiments of any of the aspects, the emulsion can comprise a) a combination of fish oil and medium-chain triglycerides (MCT) at a ratio of 60:40 to 30:70; or b) a combination of omega-3 fatty acids and medium-chain triglycerides (MCT) at a ratio of 60:40 to 30:70.

In some embodiments of any of the aspects, the emulsion can comprise a) a combination of fish oil and medium-chain triglycerides (MCT) at a ratio of about 50:50 to about 30:70; or b) a combination of omega-3 fatty acids and medium-chain triglycerides (MCT) at a ratio of about 50:50 to about 30:70. In some embodiments of any of the aspects, the emulsion can comprise a) a combination of fish oil and medium-chain triglycerides (MCT) at a ratio of 50:50 to 30:70; or b) a combination of omega-3 fatty acids and medium-chain triglycerides (MCT) at a ratio of 50:50 to 30:70.

In some embodiments of any of the aspects, the emulsion can comprise a) a combination of fish oil and medium-chain triglycerides (MCT) at a ratio of about 40:60 to about 60:40; or b) a combination of omega-3 fatty acids and medium-chain triglycerides (MCT) at a ratio of about 40:60 to about 60:40. In some embodiments of any of the aspects, the emulsion can comprise a) a combination of fish oil and medium-chain triglycerides (MCT) at a ratio of 40:60 to 60:40; or b) a combination of omega-3 fatty acids and medium-chain triglycerides (MCT) at a ratio of 40:60 to 60:40.

In some embodiments of any of the aspects, the emulsion can comprise a) a combination of fish oil and medium-chain triglycerides (MCT) at a ratio of about 50:50; or b) a combination of omega-3 fatty acids and medium-chain triglycerides (MCT) at a ratio of about 50:50. In some embodiments of any of the aspects, the emulsion can comprise a) a combination of fish oil and medium-chain triglycerides (MCT) at a ratio of 50:50; or b) a combination of omega-3 fatty acids and medium-chain triglycerides (MCT) at a ratio of 50:50.

In some embodiments of any of the aspects, the emulsion compositions described herein comprise from about 5% w/v to about 50% w/v of total fats in the total volume of the composition. Total fats can refer to the MCT and fish oil/omega-3 fatty acids collectively. In some embodiments of any of the aspects, the emulsion compositions described herein comprise from about 15% w/v to about 25% w/v of total fats in the total volume of the composition. In some embodiments of any of the aspects, the emulsion compositions described herein comprise from about 5% w/v to about 50% w/v of total fats in the total volume of the composition. In some embodiments of any of the aspects, the emulsion compositions described herein comprise from about 20% w/v of total fats in the total volume of the composition. In some embodiments of any of the aspects, the emulsion compositions described herein comprise from 5% w/v to 50% w/v of total fats in the total volume of the composition. In some embodiments of any of the aspects, the emulsion compositions described herein comprise from 15% w/v to 25% w/v of total fats in the total volume of the composition. In some embodiments of any of the aspects, the emulsion compositions described herein comprise from 5% w/v to 50% w/v of total fats in the total volume of the composition. In some embodiments of any of the aspects, the emulsion compositions described herein comprise 20% w/v of total fats in the total volume of the composition.

In some embodiments of any of the aspects, the emulsions described herein can further comprise alpha-tocopherol. As used herein, "alpha-tocopherol" refers to the form of vitamin E having the structure of Formula I, in any of its stereoisomers.

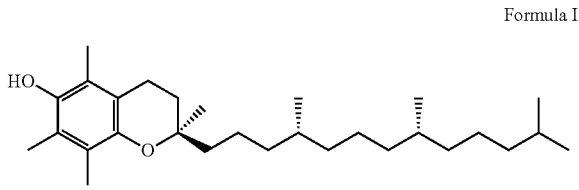 [SMILES: Cc1c(C)c2c(c(C)c1O)CC[C@@](C)(CCC[C@H](C)CCC[C@H](C)CCCC(C)C)O2]

Formula I

In some embodiments of any of the aspects, alpha-tocopherol is present in the emulsion at a level of at least 50 mg/L. In some embodiments of any of the aspects, alpha-tocopherol is present in the emulsion at a level of at least 75 mg/L. In some embodiments of any of the aspects, alpha-tocopherol is present in the emulsion at a level of at least 100 mg/L. In some embodiments of any of the aspects, alpha-tocopherol is present in the emulsion at a level of at least 120 mg/L. In some embodiments of any of the aspects, alpha-tocopherol is present in the emulsion at a level of at least 150 mg/L. In some embodiments of any of the aspects, alpha-tocopherol is present in the emulsion at a level of at least 200 mg/L.

In some embodiments of any of the aspects, the emulsion composition comprises alpha-tocopherol and other forms of vitamin E (e.g., beta tocopherol, gamma tocopherol, delta tocopherol, alpha tocotrienol, beta tocotrienol, gamma tocotrienol, and/or delta tocotrienol) at a ratio of at least 2:1 by weight. In some embodiments of any of the aspects, the emulsion composition comprises alpha-tocopherol and other forms of vitamin E at a ratio of at least 3:1 by weight. In some embodiments of any of the aspects, the emulsion composition comprises alpha-tocopherol and other forms of vitamin E at a ratio of at least 5:1 by weight. In some embodiments of any of the aspects, the emulsion composition comprises alpha-tocopherol and other forms of vitamin E at a ratio of at least 10:1 by weight. In some embodiments of any of the aspects, the emulsion composition does not comprise forms of vitamin E other than alpha-tocopherol.

In some embodiments of any of the aspects, an emulsion as described herein can comprise a) MCTs, and b) fish oil and/or omega-3 fatty acids. In some embodiments of any of the aspects, an emulsion as described herein can consist essentially of a) MCTs, and b) fish oil and/or omega-3 fatty acids. In some embodiments of any of the aspects, an emulsion as described herein can consist of a) MCTs, and b) fish oil and/or omega-3 fatty acids. In some embodiments of any of the aspects, the omega-3 fatty acid is provided as an omega-3 predominate fatty acid oil.

In some embodiments of any of the aspects, an emulsion as described herein can comprise a) MCTs, b) fish oil and/or omega-3 fatty acids, and c) one or more of an emulsifier (e.g., egg phospholipid) phospholipids, glycerin, and sodium oleate. In some embodiments of any of the aspects, an emulsion as described herein can consist essentially of a) MCTs, and b) fish oil and/or omega-3 fatty acids. In some embodiments of any of the aspects, an emulsion as described herein can comprise a) MCTs, b) fish oil and/or omega-3 fatty acids, and c) one or more of an emulsifier (e.g. phospholipids and/or egg phospholids), glycerin, and sodium oleate. In some embodiments of any of the aspects, an emulsion as described herein can consist of a) MCTs, and b) fish oil and/or omega-3 fatty acids.

In some embodiments of any of the aspects, an emulsion as described herein can comprise a) MCTs, b) fish oil and/or omega-3 fatty acids, and c) one or more of an emulsifier, phospholipids, egg phospholipids, glycerin, and sodium oleate.

In some embodiments of any of the aspects, an emulsion as described herein can comprise a) MCTs, b) fish oil and/or omega-3 fatty acids, and c) alpha-tocopherol. In some embodiments of any of the aspects, an emulsion as described herein can consist essentially of a) MCTs, b) fish oil and/or omega-3 fatty acids, and c) alpha-tocopherol. In some embodiments of any of the aspects, an emulsion as described herein can consist of a) MCTs, b) fish oil and/or omega-3 fatty acids, and c) alpha-tocopherol.

In some embodiments of any of the aspects, an emulsion as described herein can comprise a) MCTs, b) fish oil and/or omega-3 fatty acids, c) alpha-tocopherol, and d) one or more of an emulsifier, phospholipids, egg phospholipids, glycerin, and sodium oleate. In some embodiments of any of the aspects, an emulsion as described herein can consist essentially of a) MCTs, b) fish oil and/or omega-3 fatty acids, c) alpha-tocopherol, and d) one or more of an emulsifier (e.g., phospholipids or egg phospholipids), glycerin, and sodium oleate. In some embodiments of any of the aspects, an emulsion as described herein can consist of a) MCTs, b) fish oil and/or omega-3 fatty acids, c) alpha-tocopherol, and d) one or more of an emulsifier (e.g. phospholipids and/or egg phospholids), glycerin, and sodium oleate.

In some embodiments of any of the aspects, an emulsion as described herein can comprise a) MCTs, b) fish oil and/or omega-3 fatty acids, c) water, d) one or more of egg phospholipid, glycerin, sodium oleate, and sodium hydroxide, and optionally, e) alpha-tocopherol and/or phytosterols. In some embodiments of any of the aspects, an emulsion as described herein can consist essentially of a) MCTs, b) fish oil and/or omega-3 fatty acids, c) water, d) one or more of egg phospholipid, glycerin, sodium oleate, and sodium hydroxide, and optionally, e) alpha-tocopherol and/or phytosterols. In some embodiments of any of the aspects, an emulsion as described herein can consist of a) MCTs, b) fish oil and/or omega-3 fatty acids, c) water, d) one or more of egg phospholipid, glycerin, sodium oleate, and sodium hydroxide, and optionally, e) alpha-tocopherol and/or phytosterols.

In some embodiments of any of the aspects, an emulsion as described herein can comprise a) MCTs, b) fish oil and/or omega-3 fatty acids, c) water, d) egg phospholipid, glycerin, sodium oleate, and sodium hydroxide, and optionally, e) alpha-tocopherol and/or phytosterols. In some embodiments of any of the aspects, an emulsion as described herein can consist essentially of a) MCTs, b) fish oil and/or omega-3 fatty acids, c) water, d) egg phospholipid, glycerin, sodium oleate, and sodium hydroxide, and optionally, e) alpha-tocopherol and/or phytosterols. In some embodiments of any of the aspects, an emulsion as described herein can consist of a) MCTs, b) fish oil and/or omega-3 fatty acids, c) water, d) egg phospholipid, glycerin, sodium oleate, and sodium hydroxide, and optionally, e) alpha-tocopherol and/or phytosterols.

In some embodiments of any of the aspects, an emulsion as described herein can comprise a) MCTs, b) fish oil and/or omega-3 fatty acids, c) water, d) egg phospholipid, glycerin, sodium oleate, and sodium hydroxide, and e) alpha-tocopherol. In some embodiments of any of the aspects, an emulsion as described herein can consist essentially of a) MCTs, b) fish oil and/or omega-3 fatty acids, c) water, d) egg phospholipid, glycerin, sodium oleate, and sodium hydroxide, and e) alpha-tocopherol. In some embodiments of any of the aspects, an emulsion as described herein can consist of a) MCTs, b) fish oil and/or omega-3 fatty acids, c) water, d) egg phospholipid, glycerin, sodium oleate, and sodium hydroxide, and e) alpha-tocopherol.

Under certain conditions, e.g., during TPN, phytosterols (e.g., β-sitosterol, campesterol, stigmasterol, sitostanol and campestanol) can induce inflammatory conditions and PNALD. In some embodiments of any of the aspects, the emulsion does not comprise phytosterols. In some embodiments of any of the aspects, the emulsion does not comprise omega-6 fatty acids. In some embodiments of any of the aspects, the emulsion does not comprise fats and/or fatty acids obtained from a plant source. In some embodiments of any of the aspects, the emulsion does not comprise long chain fatty acids obtained from a plant source.

As described herein, the formulations of the present invention can counteract the negative side effects of phytosterols (e.g., β-sitosterol, campesterol, stigmasterol, sitostanol and campestanolomega). Accordingly, in some embodiments of any of the aspects, phytosterols and/or omega-6 fatty acids are present in the emulsions described herein. In some embodiments of any of the aspects, phytosterols are present in the emulsion at a concentration of less than 50 mg/L. In some embodiments of any of the aspects, omega-6 fatty acids are present in the emulsion at a concentration of less than 50 mg/L.

In some embodiments of any of the aspects, phytosterols are present in the emulsion at a concentration of less than 100 mg/L. In some embodiments of any of the aspects, omega-6 fatty acids are present in the emulsion at a concentration of less than 100 mg/L.

In some embodiments of any of the aspects, phytosterols are present in the emulsion at a concentration of less than 25 mg/L. In some embodiments of any of the aspects, omega-6 fatty acids are present in the emulsion at a concentration of less than 25 mg/L.

In some embodiments of any of the aspects, fats and/or fatty acids obtained from a plant source are present in the emulsion at a concentration of less than 100 mg/L, e.g., less than 100 mg/L, less than 50 mg/L, or less than 25 mg/L.

As used herein, "phytosterol" refers to sterols and stanols of plant origin, e.g., phytosteroids. Non-limiting examples of phytosterols can include β-sitosterol, campesterol, stigmasterol, sitostanol and campestanol.

As used herein, "omega-6 fatty acid" includes natural and synthetic omega-6 fatty acids, as well as pharmaceutically acceptable esters, free acids, triglycerides, derivatives, conjugates, precursors, salts, and mixtures thereof. Omega-6 fatty acids can include, but are not limited to, Linoleic acid (LA); Gamma-linolenic acid (GLA); Calendic acid; Eicosa-dienoic acid; Dihomo-gamma-linolenic acid (DGLA); Arachidonic acid (AA, ARA); Docosadienoic acid; Adrenic acid; Osbond acid; Tetracosatetraenoic acid; and Tetracosapentaenoic acid. The omega-6 fatty acids may be from plant or synthetic origin.

In some embodiments of any of the aspects, arachidonic acid is present in the composition at a concentration of at least 900 mg/L. In some embodiments of any of the aspects, docosahexaenoic acid is present in the composition at a concentration of at least 13.4 grams/L. In some embodiments of any of the aspects, eicosapentaenoic acid is present in the composition of at least 11.6 grams/L.

In some embodiments of any of the asepcts, the emulsions described herein can further comprise one or more of an emulsifier (e.g. phospholipids and/or egg phospholids), glycerin, and sodium oleate. In some embodiments of any of the asepcts, the emulsion described herein can comprise 10-30% MCT and fish oil and/or omega-3 fatty acids, 0.5-2.5% egg phospholipid, 0.5-5.0% glycerin, and 0.005-0.1% sodium oleate. In some embodiments of any of the asepcts, the emulsion described herein can comprise about 20% MCT and fish oil and/or omega-3 fatty acids, about 1.2% egg phospholipid, about 2.5% glycerin, and about 0.03% sodium oleate. In some embodiments of any of the asepcts, the emulsion described herein can comprise 20% MCT and fish oil and/or omega-3 fatty acids, 1.2% egg phospholipid, 2.5% glycerin, and 0.03% sodium oleate.

The emulsion described herein can be administered, e.g., orally, parenterally, or intravenously. In some embodiments of any of the aspects, the emulsion described herein is formulated for oral administration. In some embodiments of any of the aspects, the emulsion described herein is formulated for parenteral and/or intravenous administration.

In some embodiments of any of the aspects, the compositions described herein can be prepared by first emulsifying each component as a separate emulusion and then mixing or combining those emulsions together, e.g., by emulsifying an omega-3 fatty acid oil source (e.g., an omega-3 fatty acid predominate oil) and/or fish oil, emulsifying an MCT, and then mixing or combining those two emulsifications together to yield the final combined MCT and fish oil (or omega-3 fatty acids) emulsion in the aforementioned combinations.

In some embodiments of any of the aspects, each emulsion can be individually formulated in the the following manner via high-pressure homogenization: first a lipid dispersion is created using an egg phospholipid emulsifier that is added to heated, (75-90° C.), USP-grade sterile water for injection (SWFI), under high-speed shear mixing conditions. The temperature is allowed to decrease to 40-45° C. Sodium oleate is then added and shear mixing continued at 3900-4000 RPM for 40 minutes. Heated SWFI is then serially added to maintain the temperature at 40-45° C. Glycerin is added under continuous shear mixing. This results in a dispersion comprised of 12% egg phospholipid, 25% glycerin, and 0.3% sodium oleate. The crude dispersion is then transferred to a homogenizer and homogenized at 9000 psi at 40-45° C. for 20 cycles, filtered through a 0.45 μm membrane, and pH is adjusted to 10.4 with 0.5N sodium hydroxide (NaOH). All steps are performed under a nitrogen atmosphere. To compound the emulsions, the oil (e.g., fish oil or MCT oil) is added to the dispersion agent in a thin stream under continuous shear mixing conditions at 3500-4500 RPM for 40-45 minutes, maintaining a 40-45° C. temperature. The resulting crude emulsions are transferred to the homogenizer and homogenized at 5000 psi and 40-45° C. for no less than 9 cycles of the emulsion. The pH of the emulsions are buffered to >8.8 using 0.1N NaOH. All steps of the compounding process are performed under a nitrogen atmosphere. The finished emulsions are aliquoted into glass serum vials and headspaces are flooded with nitrogen gas before sealing. All vials were heat sterilized. This allows optimal homogenization of each oil type to improve compliance with Chapter <729> of the United States Pharmacopoeia (USP) requirements that parenteral fat emulsions have a mean fat globule size <500 nm and a percent of fat globules >5 µm (PFAT5) ≤0.05%.

In some embodiments of any of the aspects, the lipid emulsions described herein can be a mixture of two or more emulsions. This approach can have the advantage of allowing additional components to be readily added to the mixture after the intial emulsification of the lipids. By way of non-limiting example, a 50:50 blend of 20% fish oil emulsion combined with 20% MCT oil emulsion can be further supplemented with, e.g., additional fish oil emulsion, trigylcerides, DHA, linoleic acid, or other lipids as needed, for a patient specific condition at the time of administration as opposed to the time of manufacture. This allows more flexibility for the prescriber to titrate the blend of oils for patient specific conditions and decreases the need for practitioners to maintain multiple combinations of finished MCT and fish oil (or omega-3 fatty acids) emulsion combinations.

In some embodiments of any of the aspects, the compositions described herein can be prepared by first mixing the components together and then preparing an emulsification of the mixture, e.g., by mixing an omega-3 fatty acid oil source and/or fish oil with a MCT, and then emulsifying the mixture. In some embodiments of any of the aspects, the lipid emulsions described herein can be an emulsification of a mixture of lipid preparations.

To prepare the lipid emulsions in accordance with the present invention, one or more emulsifying agents can be mixed with, e.g., the source of omega-3 fatty acids or MCTs. Emulsifying agents for this purpose are generally phospholipids of natural, synthetic or semi-synthetic origin. A variety of suitable emulsifying agents are known in the art. Examples of suitable emulsifying agents include, but are not limited to, egg phosphatidylcholine, egg lecithin, L-α-dipalmitoyl phosphatidylcholine (DPPC), DL-α-dipalmitoyl phosphatidylethanolamine (DPPE), and dioleoyl phosphatidylcholine (DOPC). In accordance with the present invention, the total concentration of diglycerides and monoglyceride as well as free fatty acids in the emulsifier should be low in order to minimize the contribution to the total oil concentration of the emulsion. In one embodiment of the present invention, the total concentration of triglycerides as well as free fatty acids in the emulsifier is less than about 3.5%. In some embodiments of any of the aspects, lecithin is used as the emulsifying agent in the lipid emulsions. Alternatively, egg lecithin can be used as the emulsifying agent. Egg lecithin containing 80-85% phosphatidyl choline and less than about 3.5% of fat can also be used as an emulsifying agent. One skilled in the art will appreciate that other components may be present in the egg lecithin without adversely affecting the emulsifying properties. For example, the egg lecithin may contain one or more of phosphatidyl ethanolamine, lysophosphatidyl choline, lysophosphatidyl ethanolamine, sphingomeylin and other natural components.

In some embodiments of any of the aspects, an emulsion as described herein comprises between about 0.5% and about 5% (w/v) emulsifying agent. In some embodiments of any of the aspects, an emulsion as described herein comprises between about 0.6% and about 2% (w/v) emulsifying agent. In some embodiments of any of the aspects, an emulsion as described herein comprises between about 0.8% and about 1.8% (w/v) emulsifying agent. In some embodiments of any of the aspects, an emulsion as described herein comprises between about 1.0% and about 1.5% (w/v) emulsifying agent. In some embodiments of any of the aspects, an emulsion as described herein comprises about 1.2% (w/v) emulsifying agent.

The ratio of lecithin to oil (e.g., MCT, fish oil, and/or omega-3 fatty acids) in the emulsion is important in determining the size of the oil globules formed within the emulsion. In some embodiments of any of the aspects, the ratio of lecithin to oil is between about 1:4 and about 1:20. In some embodiments of any of the aspects, the ratio is between about 1:4 and about 1:18. In some embodiments of any of the aspects, the ratio is between about 1:4 and about 1:15. In some embodiments of any of the aspects, the ratio is between about 1:4 and about 1:10.

The lipid emulsion in accordance with the present invention can further comprise additional components such as, antioxidants, chelating agents, osmolality modifiers, buffers, neutralization agents and the like that improve the stability, uniformity and/or other properties of the emulsion. Suitable antioxidants that can be added to the lipid emulsions include, but are not limited to, alpha-tocopherol (vitamin E) and tocotrienols. As is known in the art, tocotrienols are a natural blend of tocotrienols and vitamin E extract concentrated from rice bran oil distillate. Tocotrienols have a similar structure to vitamin E and contain three double bonds in the carbon side chain of the molecule. In some embodiments of any of the aspects, the concentration of antioxidant added to the emulsion is typically between about 0.002 and about 1.0% (w/v). In some embodiments of any of the aspects, the concentration of antioxidant used in the emulsion is between about 0.02% and about 0.5% (w/v). In some embodiments of any of the aspects, tocotrienols are added to the emulsion as an antioxidant. In some embodiments of any of the aspects, about 0.5% (w/v) tocotrienols are added to the emulsion. In some embodiments of any of the aspects, vitamin E is added to the emulsion as an antioxidant. In some embodiments of any of the aspects, about 0.02% (w/v) vitamin E is added to the emulsion.

The emulsion can further comprise a chelating agent to improve the stability of the emulsion and reduce the formation of oxidized fatty acids. Suitable chelating agents are known in the art and are those that are generally recognized as safe (GRAS) compounds. Examples include, but are not limited to, EDTA. In some embodiments of any of the aspects, the emulsion comprises EDTA. In some embodiments of any of the aspects, the emulsion comprises concentrations of EDTA between about $1 \times 10^{-6}$ M and $5 \times 10^{-5}$ M.

An osmolality modifier can also be incorporated into the emulsion to adjust the osmolality of the emulsion to a value suitable for parenteral administration. Amounts and types of osmolality modifiers for use in parenteral emulsions are well-known in the art. An example of a suitable osmolality modifier is glycerol. The concentration of osmolality modifier typically ranges from about 2% to about 5% (w/v). In some embodiments of any of the aspects, the amount of osmolality modifier added to the emulsion is between about 2% and about 4%. In some embodiments of any of the aspects, the amount of osmolality modifier added to the emulsion is between about 2% and about 3%. In some embodiments of any of the aspects, about 2.25% (w/v) glycerol is added to the emulsion as an osmolality modifier. In some embodiments of any of the aspects, the final product is isotonic so as to allow infusion of the emulsion through either a central or peripheral venous catheter.

The pH of the emulsion can be adjusted through the use of buffers or neutralization agents. Emulsions with pH values close to physiological pH or above have been shown to be less prone to fatty acid peroxidation. One skilled in the art will appreciate that the pH of the emulsions can be adjusted through the use of an appropriate base that neutralizes the negative charge on the fatty acids, through the use of an appropriate buffer, or a combination thereof. A variety of bases and buffers are suitable for use with the emulsions of the present invention. One skilled in the art will appreciate that the addition of buffer to the emulsion will affect not only on the final pH, but also the ionic strength of the emulsion. High ionic strengths may negatively impact the zeta potential of the emulsion (i.e. the surface charge of the oil globules) and are, therefore, not desirable. Selection of an appropriate buffer strength to provide a suitable pH is considered to be within the ordinary skills of a worker in the art. In some embodiments of any of the aspects, the pH of the emulsion is adjusted using sodium hydroxide. In some embodiments of any of the aspects, the pH is adjusted with a buffer. In some embodiments of any of the aspects, the buffer is a phosphate buffer. In some embodiments of any of the aspects, both sodium hydroxide and a phosphate buffer are added to the emulsion. In some embodiments of any of the aspects, the final pH of the emulsion is between about 6.0 and about 9.0. In some embodiments of any of the aspects, the pH of the emulsion is between about 7.0 and about 8.5. In some embodiments of any of the aspects, the pH of emulsion is between about 7.0 and about 8.0.

In some embodiments of any of the aspects, the lipid emulsion can further comprise components for adjusting the stability of the emulsion, for example, amino acids or carbohydrates, such as fructose or glucose. The lipid emulsion can also be formulated to include nutrients such as glucose, amino acids, vitamins, or other parenteral nutritional supplements. The formulation of the lipid emulsion to incorporate a therapeutic agent is also considered to be within the scope of the present invention. A "therapeutic agent" as used herein refers to a physiologically or pharmacologically active substance that produces a localized or systemic effect or effects in animals and refers generally to drugs, nutritional supplements, vitamins, minerals, enzymes, hormones, proteins, polypeptides, antigens and other therapeutically or diagnostically useful compounds.

In some embodiments of any of the aspects, the emulsion composition can further comprise an additive of one or more additional fatty acids or a mixture thereof. In some embodiments of any of the aspects, the methods described herein can further comprise administering an additive of one or more additional fatty acids or a mixture thereof. The additive can comprise one more more fatty acids which are therapeutic for a disease, e.g., a disease which the subject is in need of treatment for. For example, DHA can be therapeutic for patients with cystic fibrosis, and an additive for a subject with cystic fibrosis can comprise DHA, e.g., beyond what is necessary for nutritional balance. In some embodiments of any of the aspects, the additive comprises fatty acids in a ratio or blend which is therapeutic. In some embodiments of any of the aspects, the additive is provided at a dose of nanograms to grams/kg/day. In some embodiments of any of the aspects, the additive is provided at a dose of 1 nanogram to 10 grams/kg/day. In some embodiments of any of the aspects, the additive is provided at a dose of 1 nanogram to 100 grams/kg/day. In some embodiments of any of the aspects, the additive is provided at a dose of 1 nanogram to 1000 grams/kg/day.

In some embodiments of any of the aspects, the composition comprises a mixture of a) an emulsion of the additive (e.g., the additional fatty acid(s)) and b) one or more emulsions of i) the fish oil and/or omega-3 fatty acids and ii) the MCT. This approach, i.e., mixtures of emulsions, permits the mixture to be prepared during or immediately prior to administration (e.g., at the patient's bedside, or in an on-site pharmacy) and therefore the concentration and/or identity of the additive to be customized to the patient's needs as as clinically indicated, e.g., based on their symptoms, pathology, and/or age. In some embodiments of any of the aspects, the additive can be, e.g., additional fish oil emulsion, trigylcerides, DHA, linoleic acid, or other lipids as needed.

In one aspect, described herein is a kit comprising a composition as described herein, e.g., an emulsion as described herein. A kit is any manufacture (e.g., a package or container) comprising at least one reagent, e.g., the emulsion, being promoted, distributed, or sold as a unit for performing the methods described herein. The kits described herein can optionally comprise additional components useful for performing the methods described herein, e.g., needles, tubing, etc useful for administration by the desired route. By way of example, the kit can comprise fluids (e.g., buffers) suitable for use with the emulsions described herein, an instructional material which describes performance of a method as described herein, and the like. A kit can further comprise devices and/or reagents for delivery of the composition as described herein. Additionally, the kit may comprise an instruction leaflet and/or may provide information as to dosages, administration frequency, etc.

The kits of the invention comprise one or more packages or containers containing the emulsion in combination with a set of instructions, generally written instructions, relating to the use and dosage of the emulsion. The kits may further comprise additional containers containing one or more nutrients or therapeutic or diagnostic compounds that may be added to the emulsion prior to administration. The packages containing the emulsion may be in the form of unit doses or pharmacy bulk packages. The doses may be packaged in a format such that each dose is associated, for example, with a day of the week. There may also be associated with the kit a notice in the form prescribed by a governmental agency regulating the manufacture, use or sale of biological products, which notice reflects approval by the agency of manufacture, use or sale for human or animal administration.

Container design is also an important factor when manufacturing fat emulsions. For example, if the emulsion is packaged in glass, the container can be filled with nitrogen before the actual emulsion is added. After addition of the emulsion, the glass container can be filled again with nitrogen to remove dead space when the cap is affixed. Such nitrogen filling prevents peroxide formation. If the product is packaged in plastic, a DEHP free container that is gas impermeable can be used. The container can also have the appropriate overwrap to minimize peroxide formation in the lipids as well as leaching of the plasticizer from the container into the product itself. In addition, if plastic is used, a desiccant can be included in with the bag as well as an indicator that notes if there is a air leak in the overwrap. In some embodiments of any of the aspects, the container can be latex-free.

In one aspect of any of the embodiments, described herein is a method comprising administering an emulsion formulation as described herein to a subject in need thereof. A subject in need of an emulsion formulation as described herein can be a subject in need of supplemental nutrition (either orally or parenterally), a subject in need of parenteral nutrition, total parenteral nutrition, a subject in need of treatment for an inflammatory condition, and/or a subject in need of treatment for or reduction of inflammation. One of skill in the art can readily identify subjects who are in need of an emulsion formulation as described herein, e.g., subjects receiving parenteral nutrition who are evidencing symptoms of inflammation and/or symptoms which are accepted as indicators that traditional PN or TPN should be reduced or stopped due to risk of side effects (including inflammation and/or liver disease). Such subjects and their symptoms are described in detail, e.g., in Guidelines for the Provision and Assessment of Nutrition Support Therapy in the Adult Critically Ill Patient: Society of Critical Care Medicine (SCCM) and American Society for Parenteral and Enteral Nutrition (A.S.P.E.N.), Taylor et al., which is incorporated by reference herein in its entirety (available on the world wide web at journals.lww.com/ccmjournal/Fulltext/ 2016/02000/ Guidelines_for_the_Provision_and_Assessment_of.20.aspx)

In some embodiments of any of the apsects, the patient administered an emulsion formulation described herein can be a subject in need of treatment for a condition selected from the group consisting of: hepatic steatosis; intestinal failure; parenteral nutrition-associated liver disease (PNALD); sepsis; cystic fibrosis; sickle cell anemia; pancreatitis; inflammatory bowel disease; Crohn's disease; biliary atresia; primary sclerosis cholangitis; an inflammatory infection; an inflammatory condition; systemic inflammatory response syndrome (SIRS); hypertriglyceridemia; severe hypertriglyceridemia; severe hepatic steatosis; retinopathy of prematurity; acute tubular necrosis; IgA nephropathies; ischemia-reperfusion injury; traumatic brain injury; multi-system organ failure; respiratory distress syndrome; acute myocardial infarction; myocardial infarction; status anginosus; status asthmaticus; status epilepticus; status lacunaris; inflammatory bowel disease; regional enteritis; ulcerative colitis; severe or debilitating arthritis; arthritis; psoriasis; severe psoriasis; burns; third degree burns; pancreatitis; acute pancreatitis; intestinal failure associated liver disease (IFALD), parenteral nutrition associated cholestasis (PNAC), essential fatty acid deficiency (EFAD), parenteral nutrition dependency complicated by soy allergy or allergy to lipid emulsions comprising ingredients other than MCTs and fish oil and/or omega-3 fatty acids. In some embodiments of any of the apsects, the patient administered an emulsion formulation described herein can be a subject having or diagnosed as having a condition selected from the group consisting of: hepatic steatosis; intestinal failure; parenteral nutrition-associated liver disease (PNALD); sepsis; cystic fibrosis; sickle cell anemia; pancreatitis; inflammatory bowel disease; Crohn's disease; biliary atresia; primary sclerosis cholangitis; an inflammatory infection; an inflammatory condition; systemic inflammatory response syndrome (SIRS); hypertriglyceridemia; severe hypertriglyceridemia; severe hepatic steatosis; retinopathy of prematurity; acute tubular necrosis; IgA nephropathies; ischemia-reperfusion injury; traumatic brain injury; multi-system organ failure; respiratory distress syndrome; acute myocardial infarction; myocardial infarction; status anginosus; status asthmaticus; status epilepticus; status lacunaris; inflammatory bowel disease; regional enteritis; ulcerative colitis; severe or debilitating arthritis; arthritis; psoriasis; severe psoriasis; burns; third degree burns; pancreatitis; acute pancreatitis; intestinal failure associated liver disease (IFALD), parenteral nutrition associated cholestasis (PNAC), essential fatty acid deficiency (EFAD), parenteral nutrition dependency complicated by soy allergy or allergy to lipid emulsions comprising ingredients other than MCTs and fish oil and/or omega-3 fatty acids.

In some embodiments of any of the aspects, the subject administered an emulsion as described herein has or is in need of treatment for a liver disease, e.g., fatty liver disease. As used herein "fatty-liver disease" refers to a disease wherein fat (hepatocytes) is excessively accumulated in the liver and can cause severe diseases such as chronic hepatitis and hepatic cirrhosis. In patients with fatty liver disease, lipids, particularly neutral fat, accumulate in hepatocytes to the extent that the amount exceeds the physiologically permissible range. From a biochemical point of view, a standard for judgment of fatty liver is that the weight of neutral fat is about 10% (100 mg/g wet weight) or more of the wet weight of hepatic tissue. Fatty liver disease is generally detected by observation of elevated serum levels of liver-specific enzymes such as the transaminases ALT and AST, which serve as indices of hepatocyte injury, as well as by presentation of symptoms, which include fatigue and pain in the region of the liver, though definitive diagnosis often requires a biopsy.

In some embodiments of any of the aspects, a subject administered an emulsion as described herein has or is in need of treatment for PN associated or induced liver disease. This disease includes both biochemical, i.e., elevated serum aminotransferase, bilirubin, and alkaline phosphatase, and histologic alterations such as steatosis, steatohepatitis, lipidosis, cholestasis, fibrosis, and cirrhosis. The disease may be progressive and worsen with the course of PN administration and appears to be more prevalent in the pediatric population. Additional risk factors for this condition include prematurity, low birth weight, long-term use, the lack of concomitant oral intake, sepsis, and multiple operative procedures. Overall, the severity of PN-induced liver pathology is thought to be inversely related to the age of the patient.

In some embodiments of any of the aspects, the emulsion described herein is administered by parenteral administration (PN). In some embodiments of any of the aspects, the emulsion described herein is administered by total parenteral administration (TPN). In some embodiments of any of the aspects, the subject administered an emulsion described herein is in need of parenteral administration (PN). In some embodiments of any of the aspects, the subject administered an emulsion described herein is in need of total parenteral administration (TPN). Methods of administering lipid emulsions to patients for PN applications or therapeutic benefit are known in the art. Typically the emulsions are administered by infusion over a suitable period of time. Appropriate dosages and administration; regimens can readily be determined by one skilled in the clinical arts.

In some embodiments of any of the aspects, the subject administered an emulsion described herein, during the period of treatment in which they are administered the emulsion (e.g., the period of days or weeks in which they are administered the emulsion), is not administered and/or permitted any oral nutrition. In some embodiments of any of the aspects, the subject administered an emulsion described herein, during the period of treatment in which they are administered the emulsion (e.g., the period of days or weeks in which they are administered the emulsion), is not administered and/or permitted any oral nutrition comprising fats and/or fatty acids.

In some embodiments of any of the aspects, the subject administered an emulsion described herein, during the period of treatment in which they are administered the emulsion (e.g., the period of days or weeks in which they are administered the emulsion), is not administered any other parenteral formulations. In some embodiments of any of the aspects, the subject administered an emulsion described herein, during the period of treatment in which they are administered the emulsion (e.g., the period of days or weeks in which they are administered the emulsion), is not administered any other parenteral formulations comprising fats and/or fatty acids.

In some embodiments of any of the aspects, the subject administered an emulsion described herein, during the period of treatment in which they are administered the emulsion (e.g., the period of days or weeks in which they are administered the emulsion), is not administered and/or permitted any other nutritional sources of fats and/or fatty acids.

In some embodiments of any of the aspects, the subject administered an emulsion described herein, during the period of treatment in which they are administered the emulsion (e.g., the period of days or weeks in which they are administered the emulsion), is not administered and/or permitted any other nutritional sources of essential fatty acids. In some embodiments of any of the aspects, the subject administered an emulsion described herein, during the period of treatment in which they are administered the emulsion (e.g., the period of days or weeks in which they are administered the emulsion), is not administered and/or permitted any other oral nutritional sources of essential fatty acids. In some embodiments of any of the aspects, the subject administered an emulsion described herein, during the period of treatment in which they are administered the emulsion (e.g., the period of days or weeks in which they are administered the emulsion), is not administered and/or permitted any other parenteral nutritional sources of essential fatty acids.

In some embodiments of any of the aspects, the emulsion described herein is administered by oral administration.

In some embodiments of any of the aspects, the subject administered an emulsion described herein, during the period of treatment in which they are administered the emulsion (e.g., the period of days or weeks in which they are administered the emulsion), is not administered and/or permitted any other nutritional sources which would be sufficient to maintain a nutritional balance. In some embodiments of any of the aspects, the subject administered an emulsion described herein, during the period of treatment in which they are administered the emulsion (e.g., the period of days or weeks in which they are administered the emulsion), is not administered and/or permitted any other oral/enteral nutritional sources which would be sufficient to maintain a nutritional balance. In some embodiments of any of the aspects, the subject administered an emulsion described herein, during the period of treatment in which they are administered the emulsion (e.g., the period of days or weeks in which they are administered the emulsion), is not administered and/or permitted any other parenteral nutritional sources which would be sufficient to maintain a nutritional balance. As used herein, "nutritional balance" refers to the maintenance of growth, development, and the lack nutritional deficiencies by provision of appropriate nutrition. Nutritional balance meets each individual's requirements without excessive provision of any particular nutrient that may produce an adverse outcome.

As described elsewhere herein, the emulsions described herein are demonstrated to be suitable for monotherapy, e.g., they do not induce essential fatty acid deficiency, inflammation, and/or other nutritional deficiencies when administered as a monotherapy. This is a characteristic not shared by all fat/fatty acid compositions which may be otherwise suitable for administration (e.g., parenteral administration). Accordingly, in some embodiments of any of the aspects, the emulsion described herein is administered as a monotherapy for the condition the subject is in need of treatment for. In some embodiments of any of the aspects, the emulsion described herein is administered as a monotherapy for nutritional needs, e.g., an anti-inflammatory without significant nutritional value could be administered concurrently, but the emulsion would still be a monotherapy as regards nutritional needs. In some embodiments of any of the aspects, the emulsion described herein is administered as a monotherapy as regards fatty acids, e.g., no other source of fatty acids is administered to or consumed by the subject.

In some embodiments of any of the aspects, an emulsion described herein can be administered at a dose of from about 0.5 g fatty acids/kg/day to about 5 g fatty acids/kg/day. In some embodiments of any of the aspects, an emulsion described herein can be administered at a dose of from 0.5 g fatty acids/kg/day to 5 g fatty acids/kg/day. In some embodiments of any of the aspects, an emulsion described herein can be administered at a dose of from about 1 g fatty acids/kg/day to about 3 g fatty acids/kg/day. In some embodiments of any of the aspects, an emulsion described herein can be administered at a dose of from 1 g fatty acids/kg/day to 3 g fatty acids/kg/day. In some embodiments of any of the aspects, an emulsion described herein can be administered at a dose of about 2 g fatty acids/kg/day.

In some embodiments of any of the aspects, the administration of an emulsion as described herein is continued for at least 3 days, e.g., 3 or more days, 4 or more days, 5 or more days, 7 or more days, 2 or more weeks, 3 or more weeks, 4 or more weeks, 6 or more weeks, 2 months or more, or 3 months or more. In some embodiments of any of the aspects, the administration of an emulsion as described herein is continued for at least 3 weeks. In some embodiments of any of the aspects, the administration of an emulsion as described herein is continued for at least 6 weeks. In some embodiments of any of the aspects, the administration of an emulsion as described herein is continued for at least 3 months.

The compositions and methods described herein can be administered to a subject having or diagnosed as having a condition described herein. In some embodiments, the methods described herein comprise administering an effective amount of compositions described herein, e.g. an emulsion to a subject in order to alleviate a symptom of a condition described herein. As used herein, "alleviating a symptom" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, or intravenous administration.

The term "effective amount" as used herein refers to the amount of an emulsion described herein needed to alleviate at least one or more symptom of the disease or disorder, and relates to a sufficient amount of pharmacological composition to provide the desired effect. The term "therapeutically effective amount" therefore refers to an amount of an emulsion described herein that is sufficient to provide a particular effect (e.g., nutritional, or anti-inflammatory effect) when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the emulsion or components thereof, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inflammation or liver function among others. The dosage can be determined by a physician and adjusted, as necessary, to suit observed effects of the treatment.

In some embodiments, the technology described herein relates to a pharmaceutical composition comprising an emulsion described herein as described herein, and optionally a pharmaceutically acceptable carrier. In some embodiments, the active ingredients of the pharmaceutical composition comprise an emulsion described herein as described herein. In some embodiments, the active ingredients of the pharmaceutical composition consist essentially of an emulsion described herein as described herein. In some embodiments, the active ingredients of the pharmaceutical composition consist of an emulsion described herein as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (18) ethyl alcohol; (19) pH buffered solutions; (20) polyesters, polycarbonates and/or polyanhydrides; (21) bulking agents, such as polypeptides and amino acids (22) serum component, such as serum albumin, HDL and LDL; (23) $C_2$-$C_{12}$ alcohols, such as ethanol; and (24) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agents as described herein. It is noted that the emulsion itself can comprise water. The emulsion can be administered with other components used in parenteral nutrition solutions (e.g. dextrose, crystalline amino acids, trace elements, multivitamins, electrolytes and minerals).

In some embodiments, the pharmaceutical composition comprising an emulsion described herein as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Pharmaceutical compositions comprising an emulsion described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

The methods described herein can further comprise administering a second agent and/or treatment to the subject, e.g. as part of a combinatorial therapy. By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In certain embodiments, an effective dose of a composition comprising an emulsion described herein as described herein can be administered to a patient once. In certain embodiments, an effective dose of a composition comprising an emulsion described herein can be administered to a patient repeatedly, e.g., daily or several times a day for a period of at least 3 days, at least 4 days, at least 5 days, at least 6 days, at least 1 week, at least 2 weeks, at least 3 week, at least 4 weeks, at least 6 weeks, at least 2 months, or at least 3 months.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the components of the emulsion. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an emulsion described herein can be administered over a period of time, such as over a 5 minute, 10 minute, 15 minute, 20 minute, or 25 minute period.

The dosage ranges for the administration of an emulsion described herein, according to the methods described herein depend upon, for example, the form of the emulsion, its potency, and the extent to which symptoms, markers, or indicators of a condition described herein are desired to be reduced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an emulsion described herein in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. nutritional balance, inflammation, and/or liver function. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein. When using an experimental animal model, efficacy of treatment is evidenced when a statistically significant change in a marker is observed.

In vitro and animal model assays are provided herein which allow the assessment of a given dose of an emulsion as described herein. By way of non-limiting example, the effects of a dose of an emulsion can be assessed by administering the emulsion orally or parenterally and then assessing serum fatty acid levels, inflammatory markers (e.g., circulating TNF-alpha and/or IL-6), and liver, spleen, and/or kidney histology.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a staticaly significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of the diseases and conditions described herein. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. a condition, disease or disorder as described herein. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be an emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An emulsion composition comprising:
   a combination of fish oil and medium-chain triglycerides (MCT) at a ratio of about 30:70 to about 30:70; or
   a combination of omega-3 fatty acids and medium-chain triglycerides (MCT) at a ratio of about 30:70 to about 30:70.
2. The emulsion composition of paragraph 1, comprising:
   a combination of fish oil and medium-chain triglycerides (MCT) at a ratio of about 40:60 to about 60:40; or
   a combination of omega-3 fatty acids and medium-chain triglycerides (MCT) at a ratio of about 40:60 to about 60:40.
3. The emulsion composition of paragraph 1, comprising
   a combination of fish oil and medium-chain triglycerides (MCT) at a ratio of about 50:50; or
   a combination of omega-3 fatty acids and medium-chain triglycerides (MCT) at a ratio of about 50:50.
4. The emulsion composition of paragraph 1, comprising
   a combination of fish oil and medium-chain triglycerides (MCT) at a ratio of 50:50; or
   a combination of omega-3 fatty acids and medium-chain triglycerides (MCT) at a ratio of 50:50.
5. The emulsion composition of any of paragraphs 1-4, wherein the composition further comprises alpha-tocopherol.
6. The emulsion composition of any of paragraphs 1-5, wherein the alpha-tocopherol is present at a level of at least 100 mg/L.
7. The emulsion composition of any of paragraphs 1-6, wherein the alpha-tocopherol is present at a level of at least 120 mg/L.
8. The emulsion composition of any of paragraphs 1-7, wherein the emulsion composition comprises alpha-tocopherol and other forms of vitamin E at a ratio of at least 2:1.
9. The emulsion composition of any of paragraphs 1-8, wherein the emulsion composition comprises alpha-tocopherol and other forms of vitamin E at a ratio of at least 10:1.
10. The emulsion composition of any of paragraphs 1-9, wherein the emulsion composition does not comprise forms of vitamin E other than alpha-tocopherol.

11. The emulsion composition of any of paragraphs 1-10, wherein phytosterols are present in the composition.
12. The emulsion composition of any of paragraphs 1-11, wherein phytosterols are present in the composition at a concentration of less than 50 mg/L.
13. The emulsion composition of any of paragraphs 1-12, formulated for oral administration.
14. The emulsion composition of any of paragraphs 1-12, formulated for parenteral or intravenous administration.
15. The emulsion composition of any of paragraphs 1-14, further comprising an additive of one or more additional fatty acids or a mixture thereof.
16. The emulsion composition of paragraph 15, wherein the additive comprises one or more fatty acids which are therapeutic for a disease.
17. A method comprising administering an emulsion composition of any of paragraphs 1-16 to a subject in need thereof
18. The method of paragraph 17, wherein the administration is parenteral administration.
19. The method of paragraph 17, wherein the administration is total parenteral administration.
20. The method of paragraph 17, wherein the administration is oral administration.
21. The method of any of paragraphs 17-20, wherein the subject is in need of parenteral nutrition.
22. The method of any of paragraphs 17-21, wherein the subject is in need of total parenteral nutrition.
23. The method of any of paragraphs 17-22, wherein the patient does not receive oral nutrition.
24. The method of any of paragraphs 17-23, wherein the patient does not receive other parenteral formulations.
25. The method of any of paragraphs 17-24, wherein the patient does not receive oral nutrition which is sufficient to maintain a nutritional balance.
26. The method of any of paragraphs 17-25, wherein the patient does not receive other parenteral formulations which are sufficient to maintain a nutritional balance.
27. The method of any of paragraphs 17-26, wherein the patient does not receive other nutritional sources of fatty acids.
28. The method of any of paragraphs 17-27, wherein the patient does not receive other parenteral nutritional sources of fatty acids.
29. The method of any of paragraphs 17-28, wherein the patient does not receive other nutritional sources of essential fatty acids.
30. The method of any of paragraphs 17-29, wherein the patient does not receive other parenteral nutritional sources of essential fatty acids.
31. The method of any of paragraphs 17-30, wherein the emulsion composition of any of paragraphs 1-14 is administered as a monotherapy.
32. The method of any of paragraphs 17-31, wherein the emulsion composition of any of paragraphs 1-14 is administered as a monotherapy for nutritional needs.
33. The method of any of paragraphs 17-32, wherein the patient is a patient in need of treatment for a condition selected from the group consisting of:
    hepatic steatosis; intestinal failure; parenteral nutrition-associated liver disease (PNALD); sepsis; cystic fibrosis; sickle cell anemia; pancreatitis; inflammatory bowel disease; Crohn's disease; an inflammatory infection; an inflammatory condition; systemic inflammatory response syndrome (SIRS); intestinal failure associated liver disease (IFALD), parenteral nutrition associated cholestasis (PNAC), essential fatty acid deficiency (EFAD), parenteral nutrition dependency complicated by soy allergy or allergy to lipid emulsions comprising ingredients other than MCTs and fish oil and/or omega-3 fatty acids.
34. The method of any of paragraphs 17-33, wherein the dose administered is from about 0.5 g fatty acids/kg/day to about 5 g fatty acids/kg/day.
35. The method of any of paragraphs 17-34, wherein the dose administered is from about 1 g fatty acids/kg/day to about 3 g fatty acids/kg/day.
36. The method of any of paragraphs 17-35, wherein the dose administered is about 2 g fatty acids/kg/day.
37. The method of any of paragraphs 17-36, further comprising administering an additive of one or more additional fatty acids or a mixture thereof.
38. The method of paragraph 37, wherein the additive comprises one or more fatty acids which are therapeutic for a disease.

Some embodiments of the technology described herein can be defined according to any of the following numbered paragraphs:

1. An emulsion composition comprising:
    fish oil and medium-chain triglycerides (MCT) at a ratio between, but not inclusive of, 30:70 to about 70:30; or
    omega-3 fatty acids and medium-chain triglycerides (MCT) at a ratio of about 30:70 to about 70:30.
2. The emulsion composition of paragraph 1, comprising:
    fish oil and medium-chain triglycerides (MCT) at a ratio of about 40:60 to about 60:40; or
    omega-3 fatty acids and medium-chain triglycerides (MCT) at a ratio of about 40:60 to about 60:40.
3. The emulsion composition of paragraph 1, comprising fish oil and medium-chain triglycerides (MCT) at a ratio of about 50:50; or
    omega-3 fatty acids and medium-chain triglycerides (MCT) at a ratio of about 50:50.
4. The emulsion composition of paragraph 1, comprising fish oil and medium-chain triglycerides (MCT) at a ratio of 50:50; or
    omega-3 fatty acids and medium-chain triglycerides (MCT) at a ratio of 50:50.
5. The emulsion of any of paragraphs 1-4, wherein the emulsion is an oil in water emulsion.
6. The emulsion composition of any of paragraphs 1-5, wherein the composition further comprises alpha-tocopherol.
7. The emulsion composition of any of paragraphs 1-6, wherein the alpha-tocopherol is present at a level of at least 100 mg per liter of the emulsion composition.
8. The emulsion composition of any of paragraphs 1-7, wherein the alpha-tocopherol is present at a level of at least 120 mg per liter of the emulsion composition.
9. The emulsion composition of any of paragraphs 1-8, wherein the emulsion composition comprises alpha-tocopherol and other forms of vitamin E at a ratio of at least 2:1.
10. The emulsion composition of any of paragraphs 1-9, wherein the emulsion composition comprises alpha-tocopherol and other forms of vitamin E at a ratio of at least 10:1.
11. The emulsion composition of any of paragraphs 1-10, wherein the emulsion composition does not comprise forms of vitamin E other than alpha-tocopherol.
12. The emulsion composition of any of paragraphs 1-11, wherein phytosterols are present in the composition.

13. The emulsion composition of any of paragraphs 1-12, wherein phytosterols are present in the composition at a concentration of less than 50 mg per liter of the emulsion composition.
14. The emulsion composition of any of paragraphs 1-13, wherein arachidonic acid is present in the composition at a concentration of at least 900 mg/L.
15. The emulsion composition of any of paragraphs 1-14, wherein docosahexaenoic acid is present in the composition at a concentration of at least 13.4 grams/L.
16. The emulsion composition of any of paragraphs 1-15, wherein eicosapentaenoic acid is present in the composition of at least 11.6 grams/L.
17. The emulsion composition of any of paragraphs 1-16, wherein the composition comprises a mixture of an emulsion of a fish oil and/or omega-3 fatty acid oil and an emulsion of MCT.
18. The emulsion composition of any of paragraphs 1-17, wherein the composition comprises an emulsion of a mixture of a fish oil and/or omega-3 fatty acid oil and an MCT.
19. The emulsion composition of any of paragraphs 1-18, wherein the fish oil and/or omega-3 fatty acid oil have not been distilled or re-esterified.
20. The emulsion composition of any of paragraphs 1-19, wherein the total triglyceride+diglyceride content of the fish oil and/or omega-3 fatty acid oil comprise no more than 10% diglyceride.
21. The emulsion composition of any of paragraphs 1-20, formulated for parenteral or intravenous administration.
22. The emulsion composition of any of paragraphs 1-21, further comprising an additive of one or more additional fatty acids or a mixture thereof.
23. The emulsion composition of paragraph 22, wherein the additive comprises one or more fatty acids which are therapeutic for a disease.
24. The emulsion composition of any of paragraphs 1-23, wherein the composition comprises a mixture of a) an emulsion of the additive and b) one or more emulsions of i) the fish oil and/or omega-3 fatty acids and ii) the MCT.
25. The emulsion composition of any of paragraphs 1-24, further comprising one or more of egg phospholipid, glycerin, sodium oleate, and sodium hydroxide.
26. The emulsion composition of any of paragraphs 1-25, further comprising egg phospholipid, glycerin, sodium oleate, and sodium hydroxide.
27. A method comprising administering an emulsion composition of any of paragraphs 1-26 to a subject in need thereof
28. The method of paragraph 27, wherein the administration is parenteral administration.
29. The method of paragraph 28, wherein the administration is total parenteral administration.
30. The method of any of paragraphs 27-29, wherein the subject is in need of parenteral nutrition.
31. The method of any of paragraphs 27-30, wherein the subject is in need of total parenteral nutrition.
32. The method of any of paragraphs 27-31, wherein the patient does not receive oral nutrition.
33. The method of any of paragraphs 27-32, wherein the patient does not receive other parenteral formulations.
34. The method of any of paragraphs 27-33, wherein the patient does not receive oral nutrition which is sufficient to maintain a nutritional balance.
35. The method of any of paragraphs 27-34, wherein the patient does not receive other parenteral formulations which are sufficient to maintain a nutritional balance.
36. The method of any of paragraphs 27-35, wherein the patient does not receive other nutritional sources of fatty acids.
37. The method of any of paragraphs 27-36, wherein the patient does not receive other parenteral nutritional sources of fatty acids.
38. The method of any of paragraphs 27-37, wherein the patient does not receive other nutritional sources of essential fatty acids.
39. The method of any of paragraphs 27-38, wherein the patient does not receive other parenteral nutritional sources of essential fatty acids.
40. The method of any of paragraphs 27-39, wherein the emulsion composition of any of paragraphs 1-26 is administered as a monotherapy.
41. The method of any of paragraphs 27-40, wherein the emulsion composition of any of paragraphs 1-26 is administered as a monotherapy for nutritional needs.
42. The method of any of paragraphs 27-41, wherein the patient is a patient in need of treatment for a condition selected from the group consisting of:
   hepatic steatosis; intestinal failure; parenteral nutrition-associated liver disease (PNALD); sepsis; cystic fibrosis; sickle cell anemia; pancreatitis; inflammatory bowel disease; Crohn's disease; biliary atresia; primary sclerosis cholangitis; an inflammatory infection; an inflammatory condition; systemic inflammatory response syndrome (SIRS); hypertriglyceridemia; severe hypertriglyceridemia; severe hepatic steatosis; retinopathy of prematurity; acute tubular necrosis; IgA nephropathies; ischemia-reperfusion injury; traumatic brain injury; multi-system organ failure; respiratory distress syndrome; acute myocardial infarction; myocardial infarction; status anginosus; status asthmaticus; status epilepticus; status lacunaris; inflammatory bowel disease; regional enteritis; ulcerative colitis; severe or debilitating arthritis; arthritis; psoriasis; severe psoriasis; burns; third degree burns; pancreatitis; acute pancreatitis; intestinal failure associated liver disease (IFALD), parenteral nutrition associated cholestasis (PNAC), essential fatty acid deficiency (EFAD), parenteral nutrition dependency complicated by soy allergy or allergy to lipid emulsions comprising ingredients other than MCTs and fish oil, omega-3 predominate fatty acid oil, and/or omega-3 fatty acids.
43. The method of any of paragraphs 27-42, wherein the dose administered is from about 0.5 g fatty acids/kg/day to about 5 g fatty acids/kg/day.
44. The method of any of paragraphs 27-43, wherein the dose administered is from about 1 g fatty acids/kg/day to about 3 g fatty acids/kg/day.
45. The method of any of paragraphs 27-44, wherein the dose administered is about 2 g fatty acids/kg/day.
46. The method of any of paragraphs 27-45, wherein the dose administered is from about 0.5 g fish oil/kg/day to about 5 g fish oil/kg/day.
47. The method of any of paragraphs 27-46, wherein the dose administered is from about 1 g fish oil/kg/day to about 3 g fish oil/kg/day.
48. The method of any of paragraphs 27-47, wherein the dose administered is about 2 g fish oil/kg/day.

49. The method of any of paragraphs 27-48, further comprising administering an additive of one or more additional fatty acids or a mixture thereof.
50. The method of paragraph 49, wherein the additive comprises one or more fatty acids which are therapeutic for a disease.
51. The method of any of paragraphs 27-50, wherein the emulsion composition comprises a mixture of a) an emulsion of the additive and b) one or more emulsions of i) the fish oil and/or omega-3 fatty acids and ii) the MCT.
52. The method of paragraph 51, wherein the mixture is prepared at the time or location of administration.
53. The method of paragraph 52, further comprising preparing the mixture as clinically indicated.
54. An emulsion composition of any of paragraph 1-26, for use in providing parenteral nutrition to a subject in need thereof
55. The emulsion composition of paragraph 54, wherein the emulsion composition is administered by parenteral administration.
56. The emulsion composition of any of paragraphs 54-55, wherein the emulsion composition is administered by total parenteral administration.
57. The emulsion composition of any of paragraphs 54-56, wherein the subject is in need of total parenteral nutrition.
58. The emulsion composition of any of paragraphs 54-57, wherein the patient does not receive oral nutrition.
59. The emulsion composition of any of paragraphs 54-58, wherein the patient does not receive other parenteral formulations.
60. The emulsion composition of any of paragraphs 54-59, wherein the patient does not receive oral nutrition which is sufficient to maintain a nutritional balance.
61. The emulsion composition of any of paragraphs 54-60, wherein the patient does not receive other parenteral formulations which are sufficient to maintain a nutritional balance.
62. The emulsion composition of any of paragraphs 54-61, wherein the patient does not receive other nutritional sources of fatty acids.
63. The emulsion composition of any of paragraphs 54-62, wherein the patient does not receive other parenteral nutritional sources of fatty acids.
64. The emulsion composition of any of paragraphs 54-63, wherein the patient does not receive other nutritional sources of essential fatty acids.
65. The emulsion composition of any of paragraphs 54-64, wherein the patient does not receive other parenteral nutritional sources of essential fatty acids.
66. The emulsion composition of any of paragraphs 54-65, wherein the emulsion composition of any of paragraphs 1-26 is administered as a monotherapy.
67. The emulsion composition of any of paragraphs 54-66, wherein the emulsion composition of any of paragraphs 1-26 is administered as a monotherapy for nutritional needs.
68. The emulsion composition of any of paragraphs 54-67, wherein the patient is a patient in need of treatment for a condition selected from the group consisting of:
hepatic steatosis; intestinal failure; parenteral nutrition-associated liver disease (PNALD); sepsis; cystic fibrosis; sickle cell anemia; pancreatitis; inflammatory bowel disease; Crohn's disease; biliary atresia; primary sclerosis cholangitis; an inflammatory infection; an inflammatory condition; systemic inflammatory response syndrome (SIRS); hypertriglyceridemia; severe hypertriglyceridemia; severe hepatic steatosis; retinopathy of prematurity; acute tubular necrosis; IgA nephropathies; ischemia-reperfusion injury; traumatic brain injury; multi-system organ failure; respiratory distress syndrome; acute myocardial infarction; myocardial infarction; status anginosus; status asthmaticus; status epilepticus; status lacunaris; inflammatory bowel disease; regional enteritis; ulcerative colitis; severe or debilitating arthritis; arthritis; psoriasis; severe psoriasis; burns; third degree burns; pancreatitis; acute pancreatitis; intestinal failure associated liver disease (IFALD), parenteral nutrition associated cholestasis (PNAC), essential fatty acid deficiency (EFAD), parenteral nutrition dependency complicated by soy allergy or allergy to lipid emulsions comprising ingredients other than MCTs and fish oil, omega-3 predominate fatty acid oil, and/or omega-3 fatty acids.
69. The emulsion composition of any of paragraphs 54-68, wherein the dose administered is from about 0.5 g fatty acids/kg/day to about 5 g fatty acids/kg/day.
70. The emulsion composition of any of paragraphs 54-69, wherein the dose administered is from about 1 g fatty acids/kg/day to about 3 g fatty acids/kg/day.
71. The emulsion composition of any of paragraphs 54-70, wherein the dose administered is about 2 g fatty acids/kg/day.
72. The emulsion composition of any of paragraphs 54-71, wherein the dose administered is from about 0.5 g fish oil/kg/day to about 5 g fish oil/kg/day.
73. The emulsion composition of any of paragraphs 54-72, wherein the dose administered is from about 1 g fish oil/kg/day to about 3 g fish oil/kg/day.
74. The emulsion composition of any of paragraphs 54-73, wherein the dose administered is about 2 g fish oil/kg/day.
75. The emulsion composition of any of paragraphs 54-74, wherein the patient is further administered an additive of one or more additional fatty acids or a mixture thereof.
76. The emulsion composition of any of paragraphs 54-74, wherein the emulsion composition further comprises an additive of one or more additional fatty acids or a mixture thereof.
77. The emulsion composition of any of paragraphs 54-76, wherein the additive comprises one or more fatty acids which are therapeutic for a disease.
78. The emulsion composition of any of paragraphs 54-77, wherein the emulsion composition comprises a mixture of a) an emulsion of the additive and b) one or more emulsions of i) the fish oil and/or omega-3 fatty acids and ii) the MCT.
79. The emulsion composition of paragraph 78, wherein the mixture is prepared at the time or location of administration.
80. The emulsion composition of paragraph 79, further comprising preparing the mixture as clinically indicated.

EXAMPLES

Example 1—The Role of Alpha-Tocopherol and Phytosterols in Fish Oil-Mediated Protection from Parenteral Nutrition-Associated Liver Injury Parenteral nutrition-associated liver disease (PNALD) is a risk of long-term parenteral nutrition (PN)-dependence characterized by the development of hepatic inflammation and cholestasis. Use of soybean oil-based intravenous lipid emulsions as parenteral fat sources can exacerbate the risk of developing PNALD, however intravenous fat for PN-dependent patients cannot be eliminated due to the risk of essential fatty acid deficiency. Intravenous fish oil lipid emulsions can effectively treat PNALD while providing sufficient essential fatty acids. However, the mechanisms by which fish oil protects the liver are not completely understood. Two important differences between fish oil and soybean oil are phytosterol content and alpha-tocopherol content. As described herein, intravenous lipid emulsions were formulated in the laboratory to explore the roles of phytosterols and alpha-tocopherol in modulating hepatic protection in a murine model of parenteral nutrition-associated liver injury. Utilizing lipid emulsions formulated in the laboratory, a soybean oil emulsion (SO) was unable to protect from PN-induced hepatosteatosis in mice whereas an emulsion of soybean oil to which α-tocopherol had been added (SO+AT) preserved normal hepatic architecture. A fish oil emulsion (FO) and an emulsion of fish oil to which phytosterols had been added (FO+P) were both able to protect from PN-induced steatosis. Expression of key hepatic fat metabolism genes, acetyl CoA carboxylase (ACC) and peroxisome proliferator-activated receptor gamma (PPARγ), was increased in animals administered SO, whereas ACC and PPARγ levels were comparable to chow-fed controls in animals receiving SO+AT, FO, and FO+P. This study demonstrates a hepatoprotective role for α-tocopherol in PN-induced liver injury and that phytosterols do not appear to compromise the hepatoprotective effects of fish oil.

Parenteral nutrition (PN) is the intravenous administration of macronutrients and micronutrients, including carbohydrates, protein in the form of amino acids, lipids, vitamins, and trace elements. PN is a critical component of therapy for patients with intestinal failure (IF) who are unable to absorb sufficient nutrients ingested orally due to inadequate intestinal length or intestinal malfunction. Although PN is life sustaining for IF patients, there are complications associated with administration of nutrition intravenously. One such complication is the development of parenteral nutrition-associated liver disease (PNALD), which is characterized by cholestatic liver disease that can progress to cirrhosis and end-stage liver disease necessitating liver transplantation. Traditionally, the progression of PNALD could only be stopped if patients could wean off PN and achieve enteral autonomy. More recently, it has been demonstrated that use of fish oil as a parenteral fat source can prevent PN-induced liver injury in animal models and reverse cholestasis and stop or slow the progression of liver disease in patients with PNALD.

Fat is an important component of PN. Fat in PN is an energy-dense calorie source as well as a source of the long-chain polyunsaturated essential fatty acids (EFA), which include the omega-3 and omega-6 fatty acid families. Administration of fat-free PN requires excess carbohydrate calories to meet caloric demand. Provision of fat-free PN also results in the development of essential fatty acid deficiency (EFAD), which may be characterized by dermatitis, hair loss, developmental delay, and growth impairment. PN-dependent patients can be biochemically monitored for EFAD through serum fatty acid profiling and measurement of the ratio of the nonessential omega-9 fatty acid mead acid, which is a triene, to the essential omega-6 fatty acid arachidonic acid, which is a tetraene. The biochemical definition of EFAD is a triene to tetraene ratio greater than 0.2.

Fat in PN is administered as an oil-in-water emulsion in which the oil is dispersed as globules surrounded by a phospholipid monolayer within an aqueous medium. Globules must be small enough to travel in the circulation without causing embolic events. In the United States, the United States Pharmacopeia (USP) has set standards that intravenous fat emulsions must have a mean globule size of less than 500 nm in diameter and a percentage of fat globules greater than 5 μm in diameter (PFAT5) of no more than 0.05%. The types and proportions of fatty acids administered are determined by the composition of the oils used to formulate the emulsion. Oils may also contain naturally occurring non-triglyceride components or additives that are incorporated into emulsions formulated with such oils.

Soybean oil-based fat emulsions are the most commonly used parenteral fat sources. In the United States, the only parenteral fat sources approved by the Food and Drug Administration (FDA) contain soybean oil. Exposure to intravenous soybean oil emulsions (SO) can exacerbate the risk of developing PNALD. Intravenous fish oil emulsions (FO) have been shown to prevent PN-induced liver injury in animal models. When administered as the sole parenteral fat source to patients who develop PNALD, FO can reverse cholestasis and stop the progression of liver disease. While the mechanisms for the hepatoprotective properties of FO and hepatotoxic properties of SO are not completely understood, there are several differences between fish oil and soybean oil that may be important contributors to the differential effects of SO and FO on the liver.

The purpose of this study is to test the hypothesis that α-tocopherol contributes hepatoprotective properties and phytosterols contribute hepatotoxic properties to intravenous fat emulsions. In order to test this hypothesis, it is not possible to utilize commercially available intravenous fat emulsions, as SO and FO with varying levels of phytosterols and α-tocopherol do not exist. Therefore, emulsions were formulated in the laboratory to allow for both control of the amount of α-tocopherol and phytosterols in each emulsion and uniformity of all emulsion components with variation in only the oil type. SO and FO formulated in the laboratory are safe and well tolerated in mice. FO and SO made in the laboratory have the same effects on the liver as their commercial counterparts in a murine model of PN-induced liver injury. Here it was tested whether the addition of phytosterols to fish oil rendered FO hepatotoxic, and whether the addition of α-tocopherol to soybean oil rendered SO hepatoprotective.

Methods:

Fish oil can protect from parenteral nutrition-induced hepatosteatosis in a murine model. An approach was used to test whether addition of phytosterols to fish oil compromises the hepatoprotective properties of intravenous fish oil emulsions and/or whether the addition of alpha-tocopherol to soybean oil renders soybean oil emulsions more hepatoprotective.

In the laboratory 20% oil-in-water emulsions containing soybean oil (SO), fish oil (FO), soybean oil to which 200 mg/L alpha-tocopherol had been added (SO+AT), or fish oil to which 450 mg/L phytosterols (85% beta-sitosterol, 15% stigmasterol) had been added (FO+P) were formulated. Emulsions were formulated using high-pressure homogenization. All final emulsions contained 20% oil, 1.2% egg phospholipid, 2.5% glycerin, and 0.03% sodium oleate. Table 2 shows the phytosterol and α-tocopherol levels in the emulsions made with these oils, as well as in commercially available FO (OM) and SO (IL). Phytosterol levels in the emulsions formulated with SO, SO+AT, and FO+P were comparable. Alpha-tocopherol levels in the emulsions formulated with FO, FO+P, and SO+AT were comparable. Mean globule size and PFAT5 analysis for all emulsions met USP standards (Table 1).

In the examples provided herein, the fish oil used was Crystalpure 28/12 TG™ (Product No. 30572344; BASF Pharma, Florham Park N.J.) which comprises a mixture of approximately 38% EPA+DHA, where 11.4% is DHA and 26.9% is EPA (by area). Unless specified otherwise, each component of the emulsions used in each of the Examples described herein was pharmaceutical, food, and/or technical grade.

Emulsions were utilized as fat sources in a murine model of PN-induced liver injury. Mice were placed on a standard chow diet or an oral liquid diet consisting of fat-free PN, equivalent to what patients receive. PN fed mice were administered either saline (no fat source) or one of the emulsions formulated (2.4 g/kg/day intravenously via tail vein injection). After 19 days on their respective diets, mice were euthanized. Livers were procured for histology (Hematoxylin and eosin and oil red 0), gene expression analysis by RT-PCR, and protein expression analysis by Western Blot. Right kidneys and spleens were also procured for histology.

Lipid Emulsion Formulation

Materials for Emulsions: Sterile water for injection (SWFI, Hospira, Lake Forest, Ill.), Egg phospholipid (Lipoid LLC, Newark, N.J.), Sodium Oleate (Lipoid LLC, Newark N.J.), and Glycerin (Sigma-Aldrich, St. Louis, Mo.) were used to formulate the dispersion. Oils used were USP-grade soybean oil (Spectrum Chemicals, New Brunswick, N.J.) and CrystalPure EPA 28/12 TG fish oil (BASF Ludwigshafen, Germany). Additives used were α-tocopherol (Sigma-Aldrich, St. Louis, Mo.), beta-sitosterol (Sigma-Aldrich, St. Louis, Mo.), and stigmasterol (Sigma-Aldrich, St. Louis, Mo.). Commercial emulsions used for analyses included Omegaven (Fresenius Kabi, Bad Homburg, Germany) and Intralipid (Fresenius Kabi, Uppsala, Sweden).

Preparation of FO+P oil: CrystalPure EPA 28/12 TG fish oil was heated to maintain temperature between 50-60° C. under constant stirring conditions. Phytosterols were added (85% beta-sitosterol, 15% stigmasterol) to a final concentration of 2.25 mg phytosterols per gram of oil and stirred until dissolved. When used to formulate a 20% emulsion, the calculated phytosterol concentration is 450 mg phytosterols per liter emulsion.

Preparation of SO+AT oil: Soybean oil was heated to maintain temperature between 50-60° C. under constant stirring conditions. Alpha-tocopherol was added to a final concentration of 1 mg α-tocopherol per gram of oil and stirred for 10-15 minutes. When used to formulate a 20% emulsion, the calculated α-tocopherol content is 200 mg α-tocopherol per liter emulsion.

Emulsion Formulation: Emulsion were formulated via high-pressure homogenization as previously described (Fell et al. JPEN 2017 41:181-187). All steps were performed at 40-45° C. unless otherwise specified. All steps were performed under a nitrogen atmosphere.

A dispersion was first formulated by adding frozen egg phospholipid to SWFI heated to 75-90° C. under high-speed shear mixing conditions and allowing the mixture to equilibrate at 40-45° C. Sodium oleate was added and shear mixing continued (4000-4100 RPM) for 40 minutes, after which glycerin was added. The crude dispersion was homogenized (Panda Plus™ Homogenizer, GEA Niro Saovi, Columbia, Md.) at 9000 psi for 20 cycles. The dispersion was filtered through a 0.45 um membrane and pH adjusted to 10.4 with 0.5N sodium hydroxide. The final dispersion was composed of 12% egg phospholipid, 25% glycerin, and 0.3% sodium oleate. One batch of dispersion was sufficient for the formulation of five 1-liter emulsions.

Emulsions were formulated by adding oil to an appropriate volume of dispersion under high-speed shear mixing conditions (3800-4200 RPM, adjusted to avoid foaming), with mixing continued for 40-45 minutes and slowly brought to a final volume of 500 mL with SWFI, maintaining the temperature 40-45° C. The crude emulsion was homogenized at 5000 psi for at least 9 cycles. The final emulsion was pH adjusted to 9-9.5 using 0.1N sodium hydroxide, packaged in 20 mL serum vials with head spaces flooded with nitrogen gas, and the packaged emulsions autoclaved. Final emulsion composition was 20% oil, 1.2% egg phospholipid, 2.5% glycerin, and 0.03% sodium oleate.

All emulsions underwent mean globule size and PFAT5 testing (Micro Measurements, Deerfield, Ill.) in accordance with USP <401> standards.

Determination of Phytosterol and Alpha-tocopherol Levels in Emulsions: To determine phytosterol levels, samples were saponified with 2 mol/L ethanolic KOH and sterols extracted with n-Heptane. Extracts were evaporated and separated on a capillary gas chromatography column. Detection was with flame ionization detector. Quantification was performed using epicoprostanol as an internal control. Alpha-tocopherol levels were determined as described (Xu et al. Eur. J. Lipid Sci Technol. 2015 117:15-22), however instead of using an internal calibration, external calibration was used.

Murine Model of PN-Induced Liver Injury. All animal experiments were approved by the Boston Children's Hospital Institutional Animal Care and Use Committee. Six week-old C57BL/6 mice (Jackson Labs, Bar Harbor, Me.) were administered either a standard chow diet or a liquid diet composed of the PN administered to patients at Boston Children's Hospital (20% Dextrose, 2% amino acids, 30 mEq/L sodium, 20 mEq/L potassium, 15 mEq/L calcium, 10 mEq/L Magnesium, 10 mMol/L phosphate, 36.67 mEq/L chloride, 19.4 mEq/L acetate, Pediatric multivitamins, Pediatric trace elements). PN-fed mice were administered intravenous (IV) saline, IV FO, IV FO+P, IV SO, or IV SO+AT (2.4 g/kg/day by tail vein injection). After 19 days, animals were euthanized by carbon dioxide asphyxiation. Blood was drawn for serum collection. Livers, spleens, and the right kidney were procured for further analysis. This experiment was performed twice with different batches of emulsions for each experiment. In the first experiment, 5 mice per treatment groups were used, and in the second experiment 10 mice per treatment group were used.

Organ Processing and Histology. Spleens, kidneys, and one portion of each liver were placed in 10% formalin and stored at 4° C. for 24 hours, then transferred to 70% ethanol. Samples were embedded in paraffin and sectioned for Hematoxylin and Eosin (H&E) staining to assess hepatic architecture. A second portion of each liver was placed in Optimum Cutting Temperature (OCT) medium (Fisher Scientific, Pittsburgh, Pa.) and frozen in liquid nitrogen. Samples underwent frozen sectioning and oil red 0 staining to assess hepatic fat accumulation. Visualization was with a Zeiss Axiophot™ microscope (Oberkochen, Germany). Slides were analyzed by a board-certified pathologist who was blinded to the treatment groups. A third portion of each liver was flash-frozen in liquid nitrogen and stored at −80° C. for gene and protein expression analysis.

Serum Fatty Acid Profiling. Serum fatty acid extraction was performed as previously described (Meisel et al. J Pediatr Surg 2011 46:666-673). Briefly, serum samples (30

μL per sample) with tricosanoic acid added as an internal standard underwent chloroform and methanol extraction in a ratio of 2:1 to isolate the lipid fraction. Samples were saponified with 0.5N methanolic sodium hydroxide. Samples were incubated in 14% BF3/methanol for 30 minutes at 100° C. Steps were performed under nitrogen gas atmosphere to minimize oxidation. Analysis was performed with gas liquid chromatography (Hewlett Packard 6890™) and detection with a flame ionization detector. An external fatty acid methyl ester standard (NuCheck Prep™, Elysian, Minn.) was used to identify sample fatty acid peaks.

Gene Expression Analysis. Livers were cut to 25 mg per sample and RNA was extracted using the Qiagen AllPrep™ DNA/RNA/Protein kit (Gaithersburg, Md.) according to the manufacturer's instructions. For each reaction Taqman primers (Invitrogen, Carlsbad, Calif.) and reagents (Agilent Technologies, Santa Clara, Calif.) were used according to manufacturers instructions with 200 ng RNA. A 2-step cycling RT-PCR protocol was used in an ABI One Step Plus™ cycler. An initial reverse transcription step of 30 minutes at 50° C. and 10 minutes at 95° C. was followed by an amplification step consisting 15 seconds at 95° C. and 1 minute at 60° C. cycled 40 times. Target gene expression was normalized to the GAPDH gene and compared to the chow-fed control group using the 2-ΔΔCt method.

Protein Analysis. Livers were cut to 25 mg per sample and homogenized in radioimmunoprecipitation assay (RIPA) buffer with protease inhibitor and phosphatase inhibitor using stainless steel beads in a Bullet Blender™. Protein concentrations were determined using a Bradford Assay (Bio-Rad, Hercules, Calif.). Ten milligrams of protein per sample was separated using a 4-12% Bis Tris polyacrylamide gel (Invitrogen, Carlsbad, Calif.) before being transferred to a nitrocellulose membrane. Membranes were blocked in 5% non-fat milk for 1 hour. Membranes were incubated in primary antibody overnight and in secondary antibody for 1 hour. ACC and PPARγ antibodies were from Cell Signaling technologies (Danvers, Mass.). Beta-actin antibody was from Santa Cruz Biotechnologies (Paso Robles, Calif.).

Results:

All emulsions met USP criteria for mean globule size and PFAT5 (Table 1). FO, FO, and SO+AT had similar levels of alpha tocopherol while SO contained little alpha-tocopherol, similar to the commercial SO emulsion (IL) (Table 2). On analysis of phytosterol levels, SO, SO+AT, and FO+P contained similar amounts of phytosterols, while FO and the commercial fish oil emulsion OM contain very little phytosterols (Table 2).

Figure 1B:
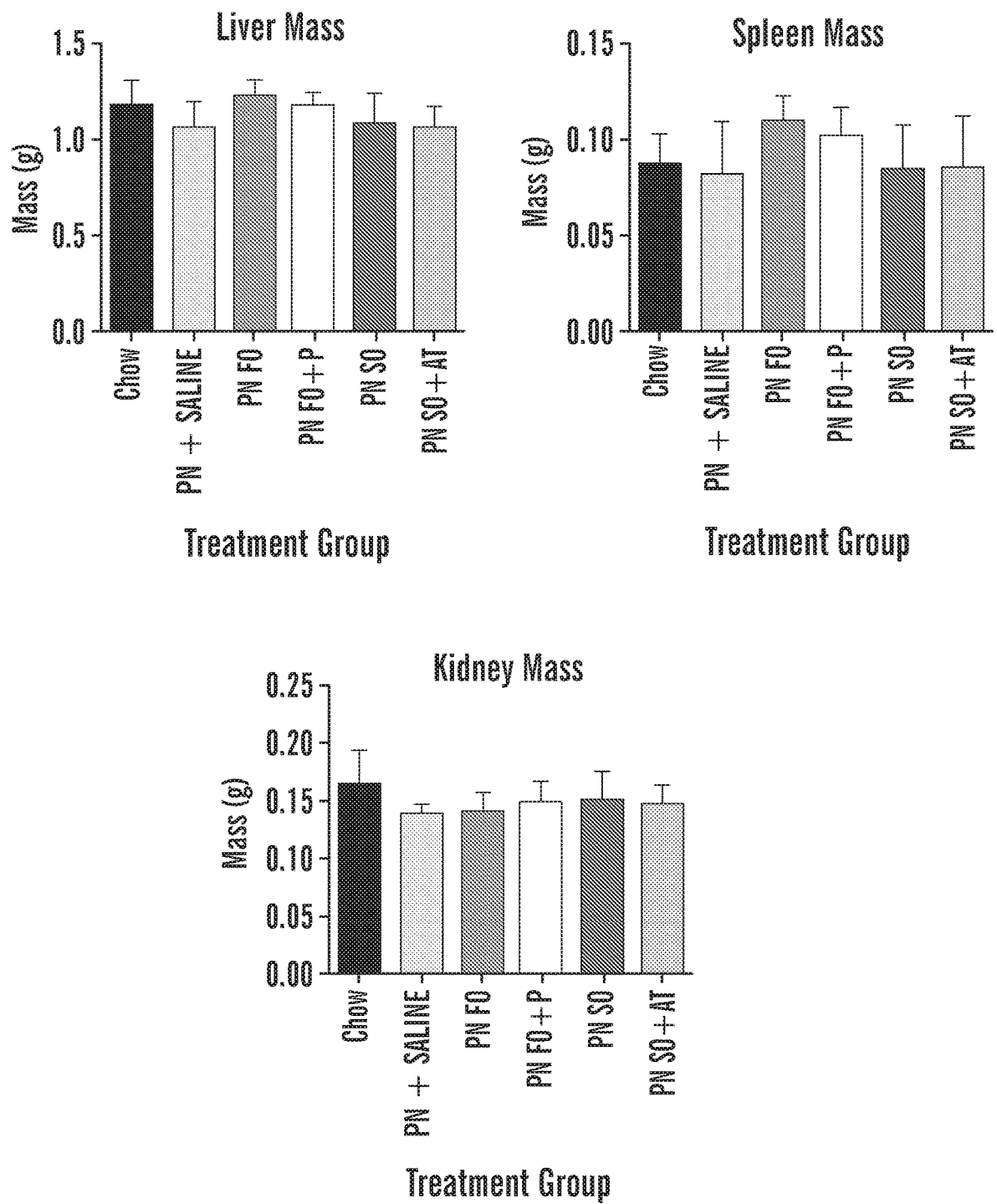

There were no adverse clinical effects with administration of any of the emulsions used, and animals tolerated all emulsions well. There were no differences in growth parameters between treatment groups, nor were there differences in gross organ assessment between groups (FIGS. 1A-1B).

Unstable intravenous emulsions can result in organomegaly, particularly enlargement of the spleen and liver due to deposition of fat globules. There was no evidence of organomegaly in any of the treatment groups. Liver (FIG. 1B), spleen (FIG. 1C), and kidney (FIG. 1D) masses were similar across all treatment groups.

Figure 2A:
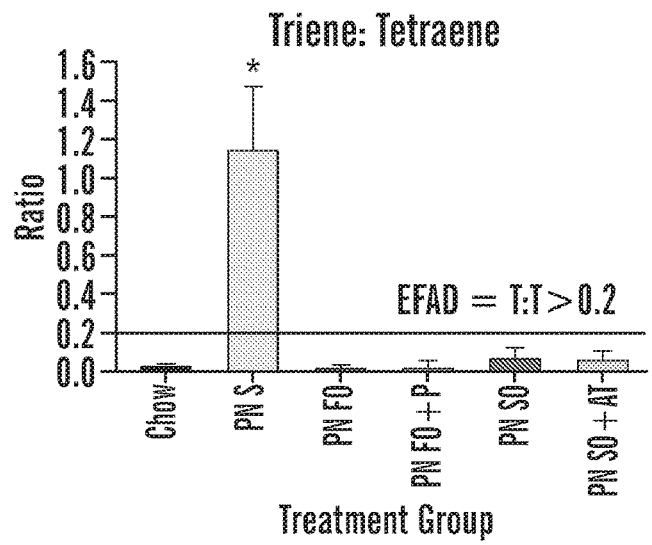
FIGS. 2A-2C depict serum levels of essential fatty acids.
Figure 2B:
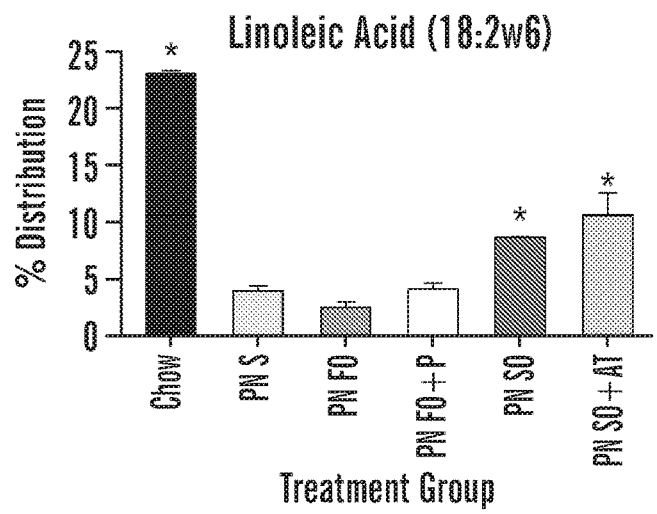
Figure 2B:
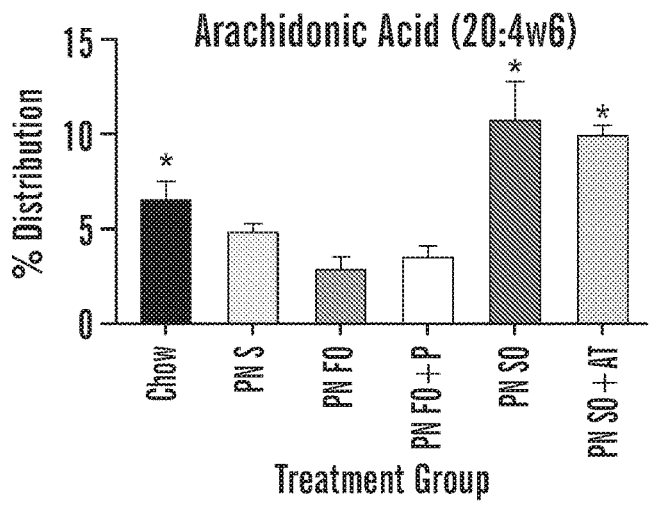
Figure 2C:
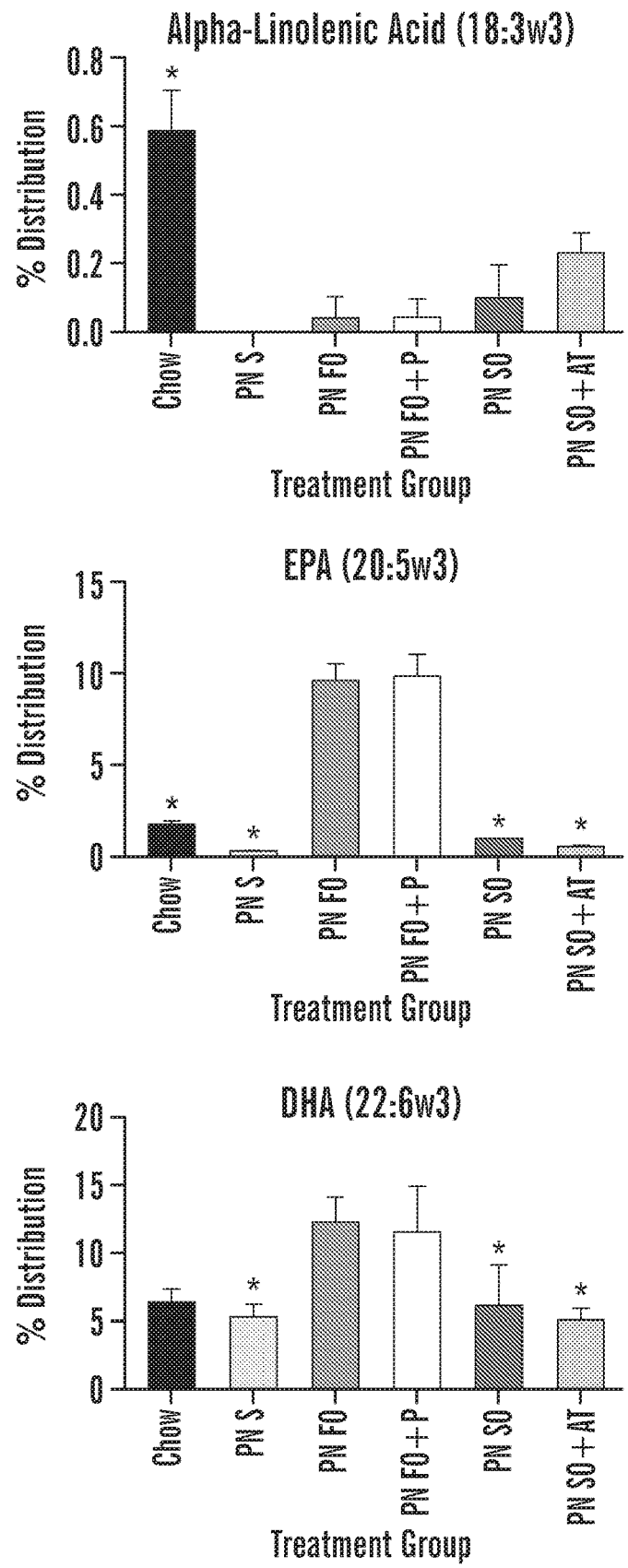

Serum fatty acid profiles were performed in order to confirm that each emulsion was able to prevent EFAD and delivered the expected complement of EFA for the oil used in the emulsion. SO is abundant in omega-6 fatty acids and contains few omega-3 fatty acids, while FO is more abundant in omega-3 fatty acids and contains a paucity of omega-6 fatty acids. These EFA balances should be reflected in the serum of animals in each respective treatment group. All emulsions prevented biochemical essential fatty acid deficiency (FIG. 2A). FO and FO+P emulsions resulted in lower serum levels of the omega-6 fatty acid arachidonic acid and higher serum levels of the omega-3 fatty acids eicosapentanoic acid (EPA) and docosahexaeonic acid (DHA) compared to the SO and SO+AT emulsions (FIG. 2C).

Serum fatty acid analysis demonstrates that only the mice receiving PN with no fat source developed essential fatty acid deficiency, defined as a triene-to-tetraene ratio greater than 0.2 (FIG. 2A). The balance of essential fatty acids reflected the fat source each group received. Mice receiving SO and SO+AT had higher levels of serum omega-6 fatty acids than the FO and FO+P groups (FIG. 2B), and mice receiving FO and FO+P had higher levels of omega-3 fatty acids than those receiving SO and SO+AT.

Figure 3A:
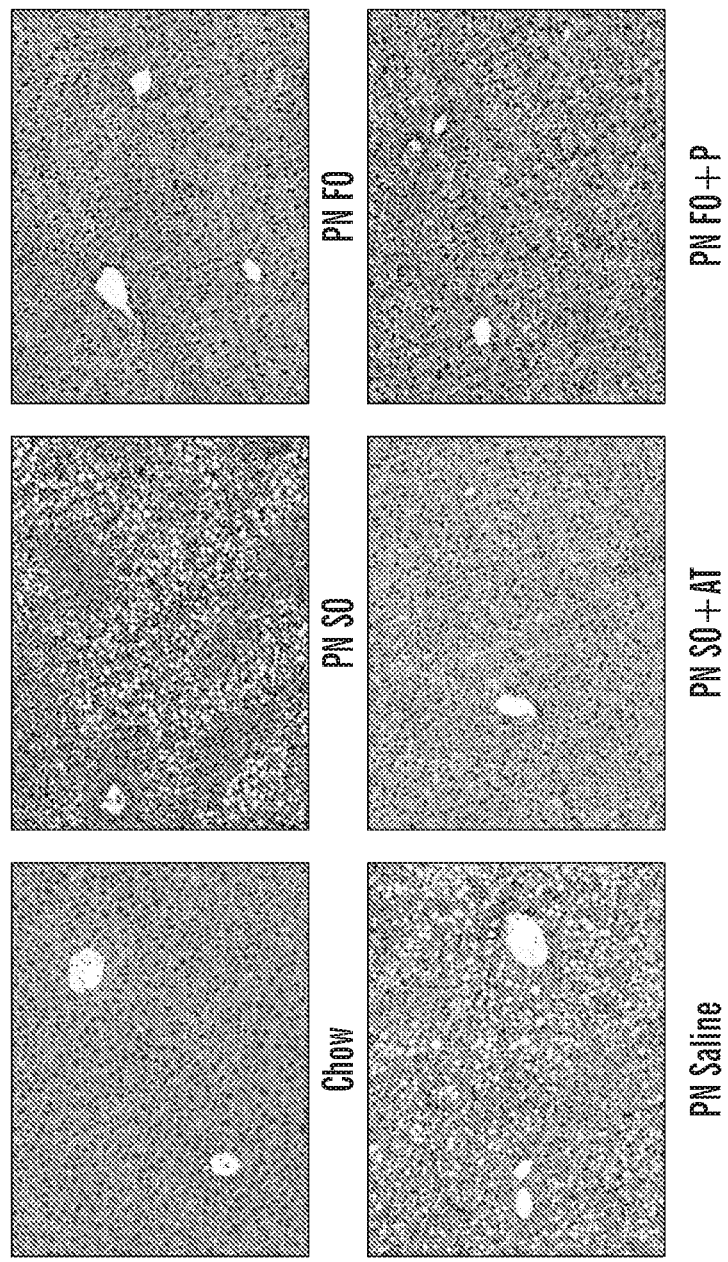
FIGS. 3A-3B demonstrate that alpha-tocopherol confers hepatoprotective properties to SO. SO+AT results in normalized hepatic architecture (FIG. 3A, bottom row, middle column) and decreased hepatic fat accumulation (FIG. 3B, bottom row, middle column) compared to SO (FIGS. 3A and 3B, top row, middle column). Phytosterols (FO+P) do not compromise the hepatoprotective properties of FO (FIGS. 3A and 3B, right column, both rows).
Figure 3B:
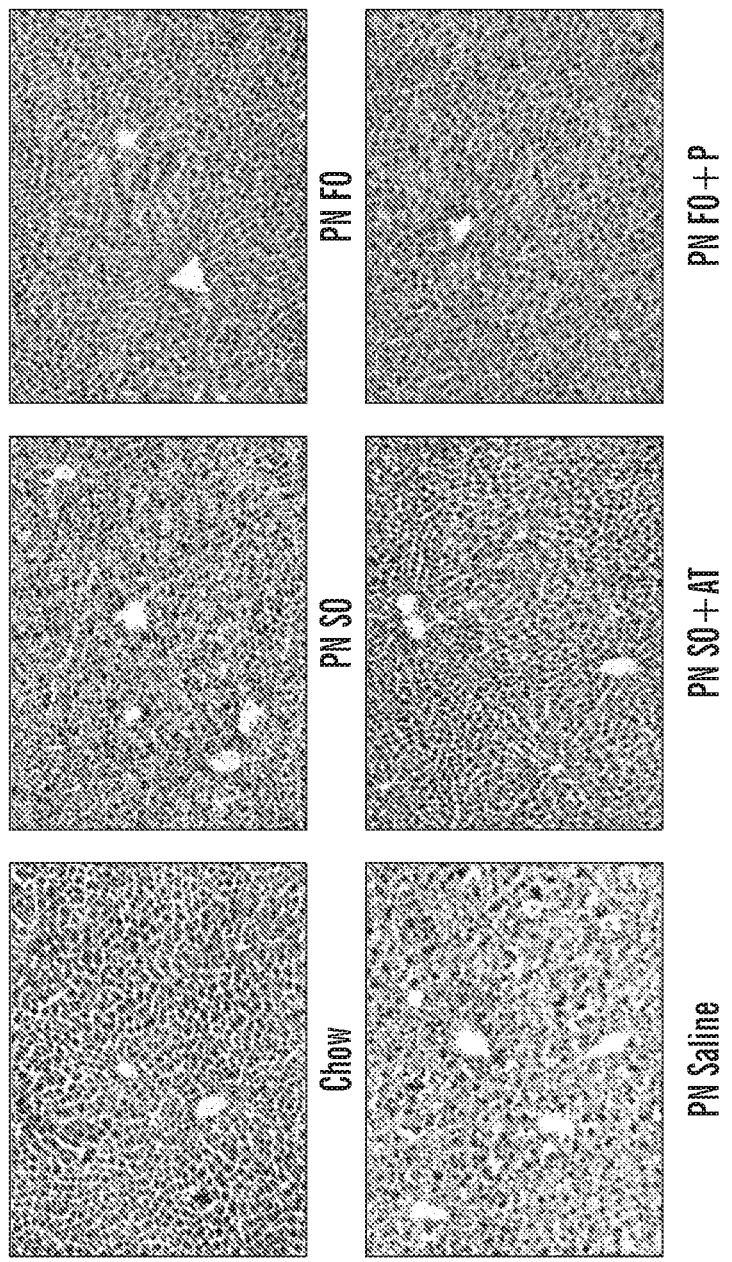

To assess the effect of each emulsion on the development of PN-induced steatosis, hepatic histologic analysis was performed. SO did not prevent PN-induced steatosis (FIG. 3A). However, addition of α-tocopherol to SO (SO+AT) resulted in preservation of normal hepatic architecture in PN-fed animals (FIG. 3A). FO and FO+P also preserved normal hepatic architecture (FIG. 3A) indicating that the addition of phytosterols to FO does not compromise the ability of FO to protect the liver from PN-induced steatosis. On Oil Red O analysis to assess hepatic fat accumulation, SO+AT resulted in decreased hepatic fat accumulation compared to SO (FIG. 3B), indicating that α-tocopherol confers hepatoprotective properties to SO. Both FO and FO+P had minimal hepatic fat accumulation, again suggesting that the addition of phytosterols to FO does not compromise the hepatoprotective properties of FO (FIG. 3B). Histologically, the PN-fed group receiving saline developed hepatosteatosis, as has been previously shown. The SO emulsion was not able to protect the liver from PN-induced steatosis. FO, FO+P, and SO+AT were able to prevent PN-induced hepatosteatosis (FIGS. 3A-3B).

Figure 4:
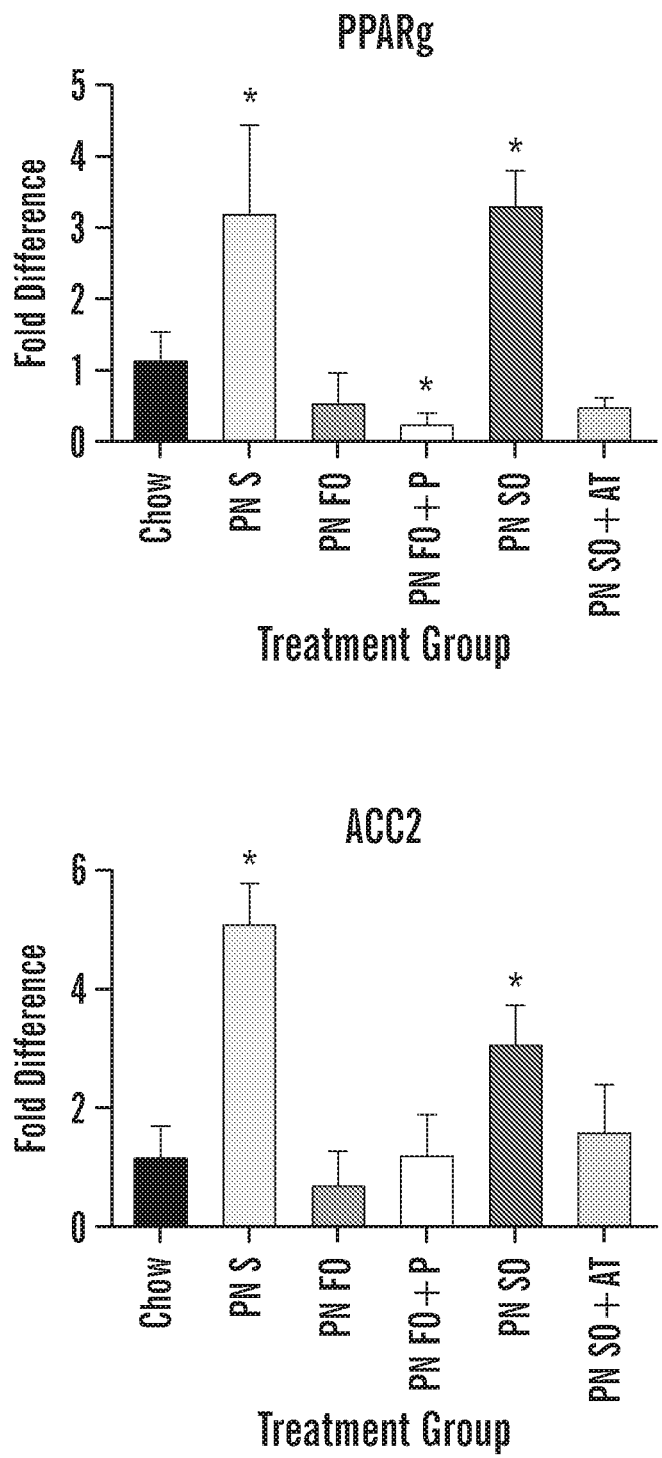
FIG. 4 depicts gene expression profiles for PPARg and ACC2. Fat-free PN and PN-fed mice administered SO had increased expression of PPARg and ACC2. FO-treated groups had normal expression of these genes, as did the SO+AT group. *=p<0.05 compared to chow by single-factor ANOVA. Results are shown as the fold difference as compared to chow diet controls.
Figure 5A:
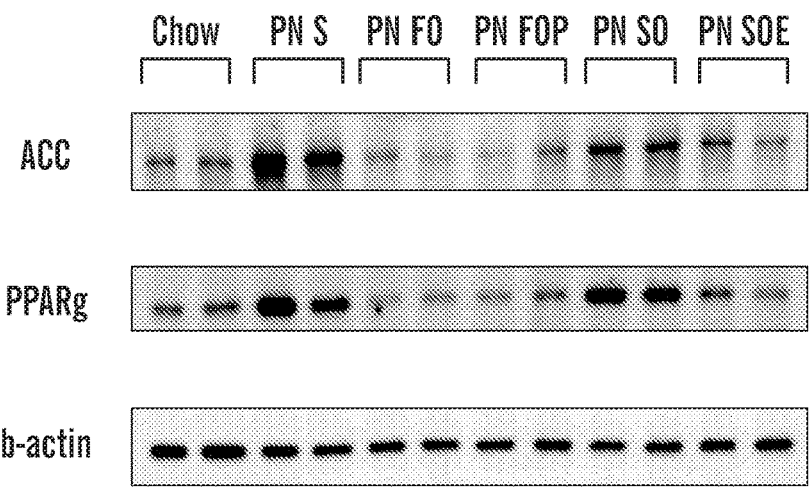
FIGS. 5A-5B depict protein expression of PPARg and ACC.
Figure 5B:
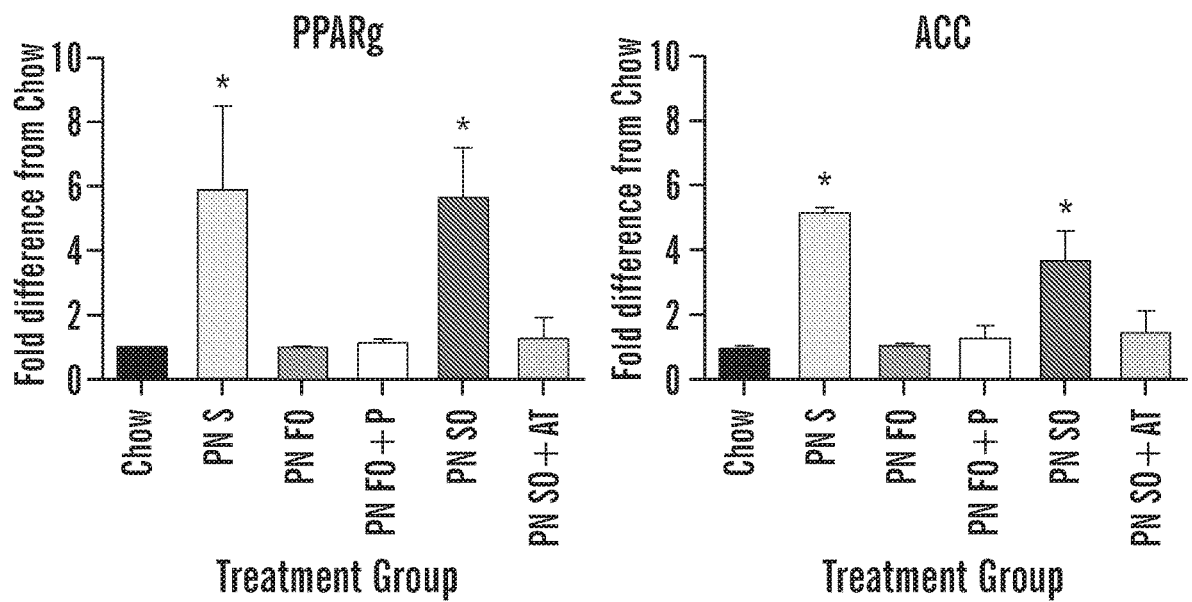

As the PN diet results in hepatic steatosis and accumulation of hepatic fat, it was hypothesized that these histologic changes may be associated with altered expression of hepatic fat-handling genes and that fish oil may preserve normal expression of such genes. On gene expression analysis, Peroxisome Proliferator-Activated Receptor gamma (PPARg), which is a transcriptional regulator of hepatic fat-handling; and Acetyl CoA Carboxylase 2 (ACC) which catalyzes the rate-limiting step of de novo lipogenesis, were increased with the fat-free PN diet and the PN-fed mice receiving SO, but were normalized to near levels of chow-fed controls in mice receiving FO, FO+P, and SO+AT (FIG. 4). This pattern was also observed at the protein expression level (FIGS. 5A-5B). This indicates that the addition of α-tocopherol can impart hepatoprotective properties to SO. Both FO and FO+P resulted in normalized gene (FIG. 4) and protein (FIG. 5) expression of ACC2 and PPARγ, indicating that at the molecular level, the addition of phytosterols does not compromise the hepatoprotective properties of FO.

This murine model histologically demonstrates steatosis in response to the PN+SO diet. However, the clinical correlate, PN-associated liver disease, is characterized by cholestasis. Therefore, it is hypothesized that phytosterol-containing intravenous fat may cause derangements in the expression of genes that regulate bile synthesis and transport. It is demonstrated herein that:

a. The addition of phytosterols does not compromise the hepatoprotective properties of fish oil in this mouse model of PN-induced liver injury b. The addition of alpha-tocopherol confers hepatoprotective properties to soybean oil, both histologically and at the molecular level, suggesting that alpha-tocopherol contributes to the hepatoprotective properties of fish oil.

c. Molecular markers (PPARg and ACC) that characterize a more hepatoprotective lipid emulsion, and distinguish such emulsions from more hepatotoxic lipid emulsions have been identified.

SHP (Small heterodimer partner) acts with FXR to regulate bile acid transport. and its expression is up-regulated in the presence of phytosterols, while the presence of alpha-tocopherol trends it towards normalizing. FXR itself is interestingly down-regulated in expression in the presence of phytosterols. MRP3 (also MRP2 and BSEP) is a target of FXR-mediated gene expression. MRP3 is down-regulated by SO, AT is unable to normalize MRP3 levels, but phytosterols do not appear to be modulating this decrease in expression as FO+P administration does not decrease MRP3 expression. Cyp7a1 is typically decreased in the setting of cholestasis. The treatment regimens described herein is is decreased in all mice receiving PN regardless of the fat source. Those receiving PN+SO or PN+FOP have more dramatic decreases in expression compared to the other groups, and it appears that alpha-tocopherol is able to partially normalize expression in animals receiving SO+AT. But it does not appear that added phytosterols to FO (FO+P compared to FO) adversely effect Cyp7a1 expression. (Some data not shown)

In this study, an intravenous lipid emulsion formulated in the laboratory using soybean oil to which α-tocopherol had been added was able to preserve normal hepatic architecture and normal expression of 2 important hepatic fat-handling genes in a murine model of PN-induced liver injury. An intravenous lipid emulsion formulated in the laboratory using soybean oil that did not contain added α-tocopherol was not able to protect from PN-induced hepatosteatosis and dysregulation of hepatic fat handling. Here, α-tocopherol was added to the soybean oil prior to formulating the emulsions.

This study also identified PPARγ and ACC2 as genes that are dysregulated by the PN diet, normalized by FO and α-tocopherol-containing SO, but not by SO alone. PPARγ is a transcriptional regulator of systemic and hepatic fat metabolism as well as inflammation. Interestingly this study did not find a hepatotoxic effect of adding phytosterols to fish oil in PN-induced liver injury. One possible conclusion is that the phytosterols in soybean oil are not responsible for the soy oil-associated hepatotoxic effects in the murine model of PN-induced liver injury. An alternative explanation is that phytosterols do have hepatotoxic properties but are unable to overcome the hepatoprotective properties of fish oil. The omega-3 fatty acids abundant in fish oil are precursors of anti-inflammatory lipid mediators, and fish oil is also abundant in α-tocopherol. These properties may offer hepatoprotection that cannot be overcome by the presence of phytosterols. A third possible explanation is that specific phytosterols at specific concentrations, or that a certain balance of phytosterols is required for phytosterol-associated hepatotoxic properties to occur. In this study, the composition of phytosterols added to fish oil approximated the types and amounts of phytosterols found in soybean oil.

All emulsions formulated in this study protected from the development of EFAD. Traditionally linoleic (LA) and alpha-linolenic (ALA) acids, the parent omega-6 and omega-3 fatty acids respectively, have been considered the EFAs. Interestingly, this study found that serum ARA, EPA, and DHA reflected the balance of EFAs provided by the emulsion administered rather than serum LA and ALA levels.

The ability of α-tocopherol to render SO less hepatotoxic in a model of PN-induced liver injury indicates that α-tocopherol can be useful in the clinical management of PNALD and other similar hepatic pathologies.

TABLE 1

USP <729> Analysis of Emulsions

| Emulsion | Mean Globule Size (nm) | PFAT5 (%) |
|---|---|---|
| FO | 238.7 | 0.032 |
| FO + P | 242.3 | 0.015 |
| SO | 252.8 | 0.009 |
| SO + AT | 252.8 | 0.013 |

TABLE 2

Phytosterol and Alpha-tocopherol Content of Emulsions

| Emulsion | Phytosterols (mg/L) | Alpha-tocopherol (mg/L) |
|---|---|---|
| OM | 10 | 193 |
| IL | 570 | 12 |
| FO | 46 | 133 |
| FO + P | 424 | 129 |
| SO | 461 | 7 |
| SO + AT | 446 | 164 |

Example 2—Formulation of Lipid Emulsions with Anti-Inflammatory Benefit for PN-Dependent Patients Long-term and short-term PN-dependent patients can be vulnerable to inflammatory insults. For long-term PN-dependent patients, chronic disease states and a long-term indwelling central venous catheter for the delivery of PN can precipitate a pro-inflammatory state. Short-term PN-dependent patients are also subject to pro-inflammatory challenges, and include trauma patients, post-operative patients, and acutely ill patients requiring an intensive care unit.

Parenteral lipid emulsions can modulate the inflammatory response, and affect the inflammatory status of PN-dependent patients. Soybean oil-based lipid emulsions are rich in pro-inflammatory omega-6 fatty acids while fish oil lipid emulsions contain an abundance of the more anti-inflammatory omega-3 fatty acids. Fish oil lipid emulsions have been utilized to treat parenteral nutrition-associated liver disease (PNALD) in patients, characterized by hepatic inflammation and cholestasis. However, in studies of the effect of oral fat sources on the inflammatory response, it has been demonstrated that fish oil as the sole fat source did not provide a greater anti-inflammatory benefit than soybean oil. Rather, mixtures of fish oil and medium-chain triglycerides (MCT) provided increased anti-inflammatory benefit as the ratio of fish oil-to-MCT decreased.

While alpha-tocopherol is an important component of fish oil to prevent oxidative degradation of the fatty acids, it remains unknown whether alpha-tocopherol may play a role in blunting the inflammatory response for PN-dependent patients. As there are many populations of PN-dependent patients who stand to benefit from blunting of the inflammatory response, the goal of this study was to develop intravenous lipid emulsions that offer anti-inflammatory benefits for the PN-dependent population while still providing adequate amounts of essential fatty acids.

It was tested whether:
a. Mixed emulsion compositions of fish oil and MCT provide more anti-inflammatory benefit than fish oil alone in response to a lipopolysaccharide challenge in a murine model
b. Emulsion compositions containing fish oil with additional alpha-tocopherol provide more anti-inflammatory benefit than fish oil alone Methods 20% oil-in-water emulsion compositions of soybean oil (SO), fish oil (FO), or MCT. SO, FO, and varying ratios of FO:MCT were tested as fat sources in a murine model of PN-induced liver injury, and their effects on the inflammatory markers Tumor Necrosis Factor-alpha (TNFa) and Interleukin-6 (IL-6) following a lipopolysaccharide (LPS) challenge were tested. LPS challenge was conducted as described in Ling PR, Malkan A, Le HD, Puder M, Bistrian BR.Arachidonic acid and docosahexaenoic acid supplemented to an essential fatty acid-deficient diet alters the response to endotoxin in rats. Metabolism. 2012 March; 61(3):395-406.

The MCT used was MCT OIL™ obtained from Nestle Health Science (Bridgewater, N.J.; HCPCS Code B4155) which is an oil emulsion comprising medium chain triglycerides obtained from coconut and/or palm kernel oil. The fatty acids are <1% shorter than C8, 54% C8 (octanoic), 41% C10 (decanoic), and less than 5% longer than C10.

Emulsion compositions containing either 20% SO, 20% FO, or 20% MCT were formulated using high-pressure homogenization. All emulsions contained 20% oil, 1.2% egg phospholipid, 2.5% glycerin, and 0.03% sodium oleate.

Mice were administered either standard chow or an oral liquid diet consisting of the fat-free PN patients receive. PN-fed mice were administered saline (no fat), or one of the following fat emulsion compositions (2.4 g/kg/day, intravenously by tail vein injection: SO, FO, 70% FO:30% MCT (70:30), 50% FO:50% MCT (50:50), 30% FO:70% MCT (70:30). After 19 days of treatment, animals were administered either saline or LPS (150 μg/kg intraperitoneally). Four hours after intraperitoneal injection, animals were euthanized. Serum was collected for fatty acid analysis and TNFa and IL-6 measurement by ELISA. Livers, spleens, and right kidneys were procured for histologic analysis.

20% oil-in-water emulsion compositions were formulated from 100% pure oil compositions of SO, FO, FO to which 500 mg/L alpha-tocopherol had been added (FOE), or MCT. Mixtures of the foregoing at different ratios were then prepared using volume, e.g., 100 mL of a 50:50 mixture of MCT:FO as described herein is made by combining 50 ml of a 20% MCT emulsion and 50 mL of a 20% FO emulsion. The emulsion compositions used in the Examples herein are therefore always a 20% total fat composition as measured by w/v.

SO, FO, FOE, and 50%:50% mixtures of FO:MCT and FOE:MCT were tested as fat sources in a murine model of PN-induced liver injury and their effects on inflammatory markers TNFa and IL-6 following an LPS challenge were tested.

Emulsions containing either 20% SO, 20% FO, 20% FOE, or 20% MCT were formulated using high-pressure homogenization. All emulsions contained 20% oil, 1.2% egg phospholipid, 2.5% glycerin, and 0.03% sodium oleate. The rest of the emulsion compositions comprised water.

Mice were administered either standard chow or an oral liquid diet consisting of the fat-free PN patients receive. PN-fed mice were administered saline (no fat), or one of the following fat emulsion compositions (2.4 g/kg/day, intravenously by tail vein injection: SO, FO, FOE, 50% FO:50% MCT (FO/MCT), or 50% FOE:50% MCT (FOE/MCT). After 19 days of treatment, animals were administered LPS (150 μg/kg intraperitoneally). Four hours after intraperitoneal injection, animals were euthanized. Serum was collected for fatty acid analysis and TNFa and IL-6 measurement by ELISA. Livers, spleens, and right kidneys were procured for histologic analysis.

Results:

All emulsions met United States Pharmacopeia criteria for mean globule size and percentage of particles larger than 0.5 μm diameter (PFAT5) (Table 3).

Figure 6A:
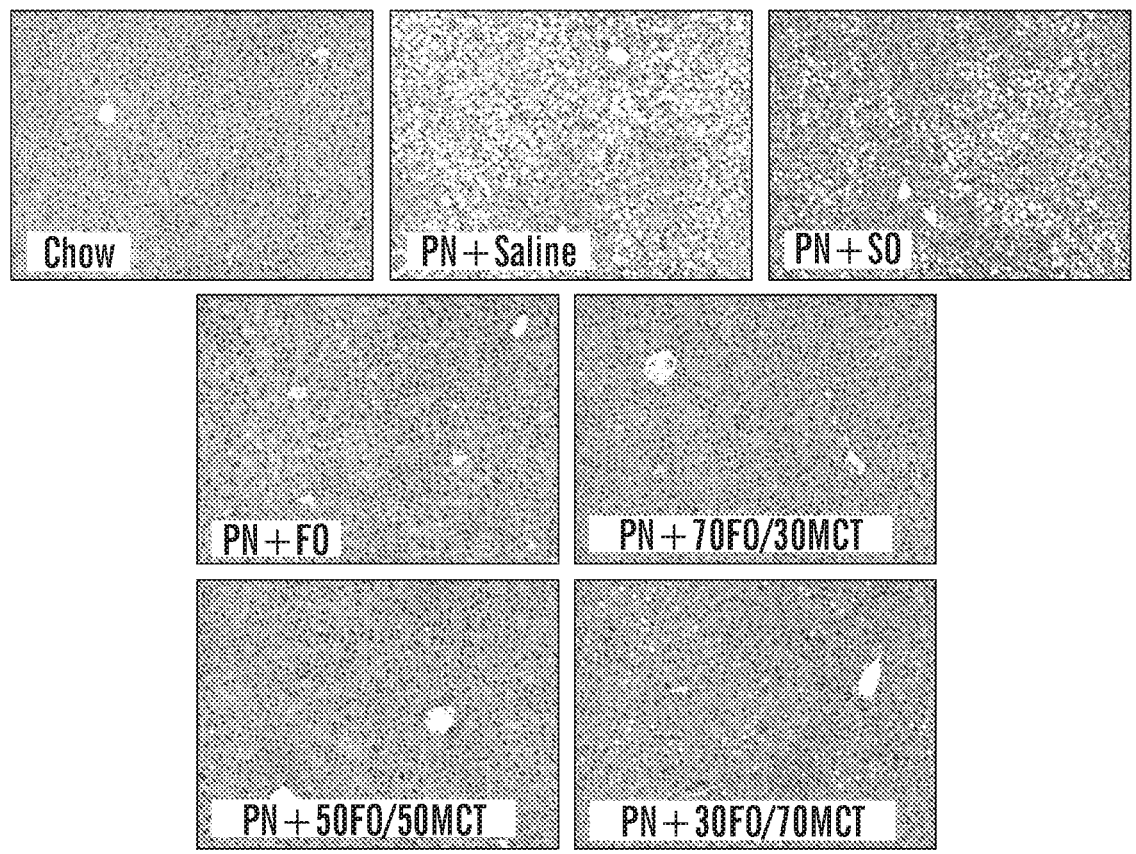
FIG. 6A depicts Hemotoxylin and Eosin.
Figure 6B:
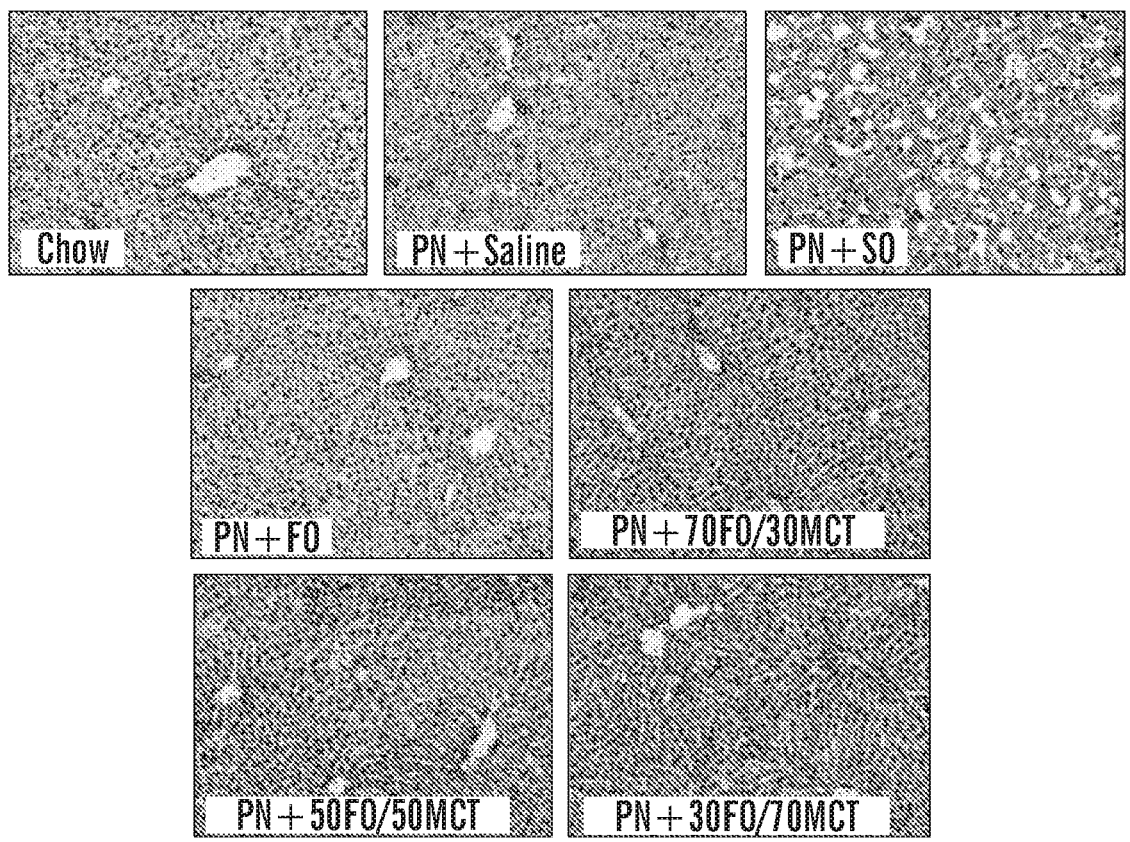
FIG. 6B depicts Oil Red O staining of livers. FO, 70:30, and 50:50 display normal hepatic architecture similar to chow. 30:70 has improved hepatic architecture compared to saline and SO groups, with mild steatosis (FIG. 6A). FO, 70:30, 50:50, and 30:70 have no observable hepatic fat accumulation (FIG. 6B).

Histologically, while PN without a fat source, and PN-fed mice with SO as a fat source developed hepatic steatosis (FIG. 6A) and hepatic fat accumulation on oil red O (FIG. 6B), PN-fed mice treated with FO or any ratio of FO:MCT had improved hepatic architecture (FIG. 6A) and minimal hepatic fat accumulation (FIG. 6B). While FO, 70:30, and 50:50 demonstrated completely normal hepatic architecture, 30:70 showed trace amounts of steatosis (FIG. 6B).

Figure 7:
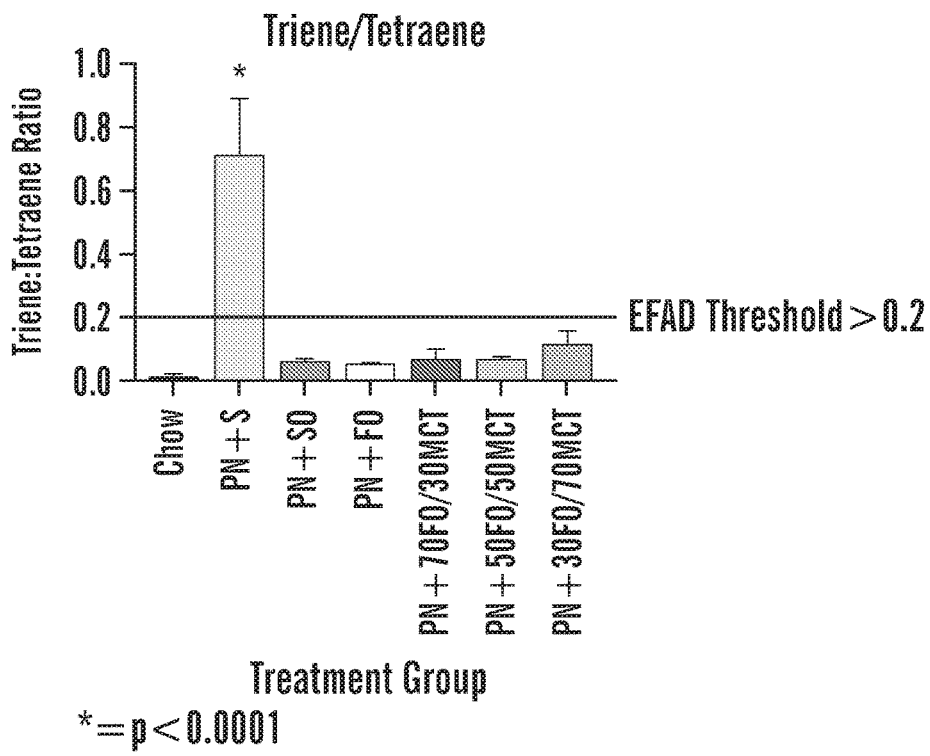
FIG. 7 demonstrates that FO, SO, and all mixtures of FO and MCT effectively prevent biochemical EFAD. *=p<0.0001 compared to chow by single-factor ANOVA.

As MCT contains no essential fatty acids, it was tested whether FO:MCT mixtures contained sufficient concentrations of essential fatty acids to prevent essential fatty acid deficiency (EFAD). SO, FO, and all mixtures of FO:MCT were able to prevent the development of biochemical EFAD (FIG. 7).

Figure 8A:
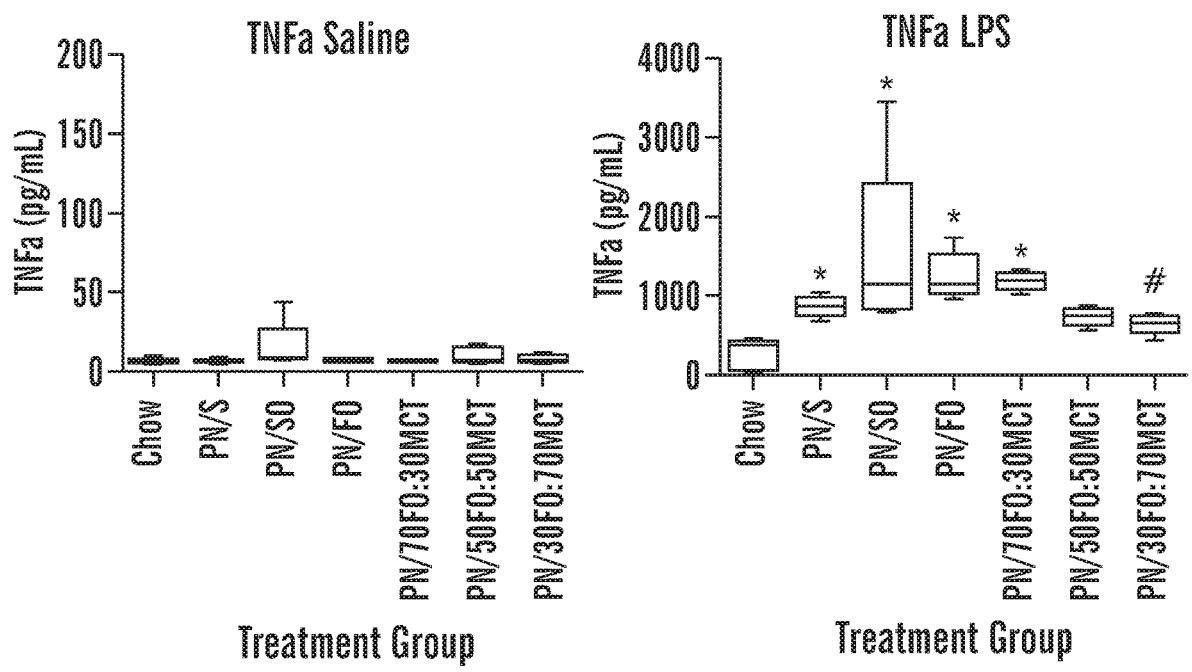
FIG. 8A depicts TNFa levels and FIG. 8B depicts IL-6 levels following saline or LPS challenge. 3A: *=p<0.05 compared to chow, and #=p<0.05 compared to FO by single-factor ANOVA 3B: *=p<0.002 compared to chow and #=p<0.05 compared to FO by single-factor ANOVA.
Figure 8B:
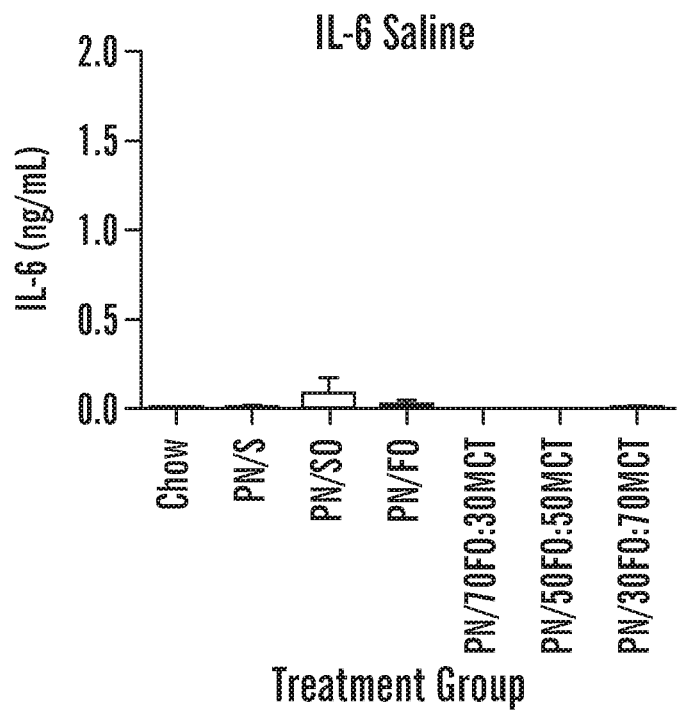
Figure 8B:
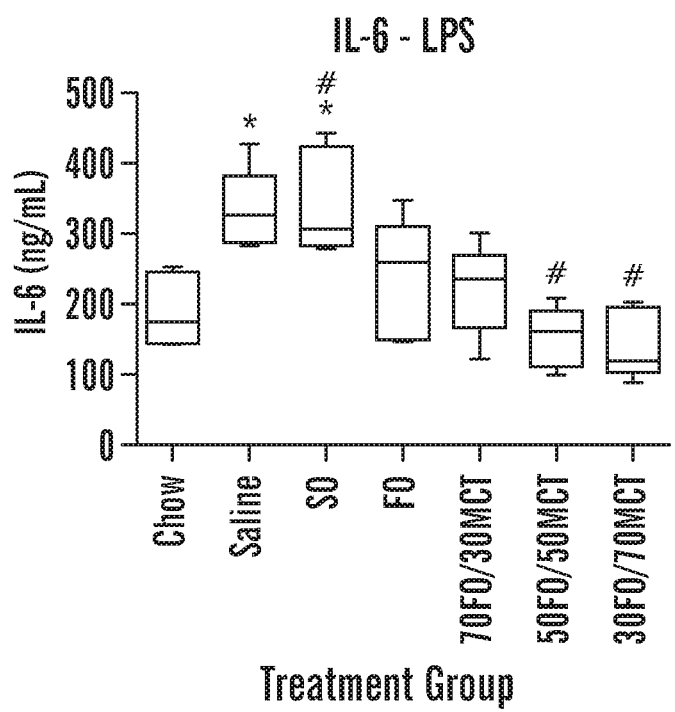

In assessment of serum TNFa and IL-6, mice injected with saline prior to euthanization demonstrated no significant elevations in either of these markers (FIGS. 8A and 8B, left graphs). Among LPS-injected mice, both IL-6 and TNFa levels following LPS injection decreased with decreasing FO:MCT ratio (FIGS. 8A and 8B, right graphs). Both 50:50 and 30:70 demonstrated significantly lower IL-6 than FO, and 30:70 also had significantly lower TNFa compared to FO.

All emulsions met United States Pharmacopeia criteria for mean globule size and PFAT5 (Table 4). Based on the above results, it was decided to utilize the 50% FO:50% MCT ratio in this experiment for mixed emulsion compositions of FO or FOE and MCT. The 50:50 group provided the most favorable balance of normal hepatic architecture and anti-inflammatory benefit in the above results.

In view of the foregoing results, additional ratios of FO:MCT were tested, including 40:60 and 60:40. Above 30% fish oil, hepatic architecture was improved, with further improvements detectable as the percentage of fish oil improved, up to 50%. Inclusion of 30% or greater MCT provided improvements in the anti-inflammatory profile, measured as described above. Accordingly, it is contemplated herein that compositions of FO and MCT with more than 30% and less than 70% fish oil (and accordingly, less than 70% and more than 30% MCT) provide a surprisingly advantageous mix of effects on hepatic architecture and anti-inflammatory activity.

Figure 9A:
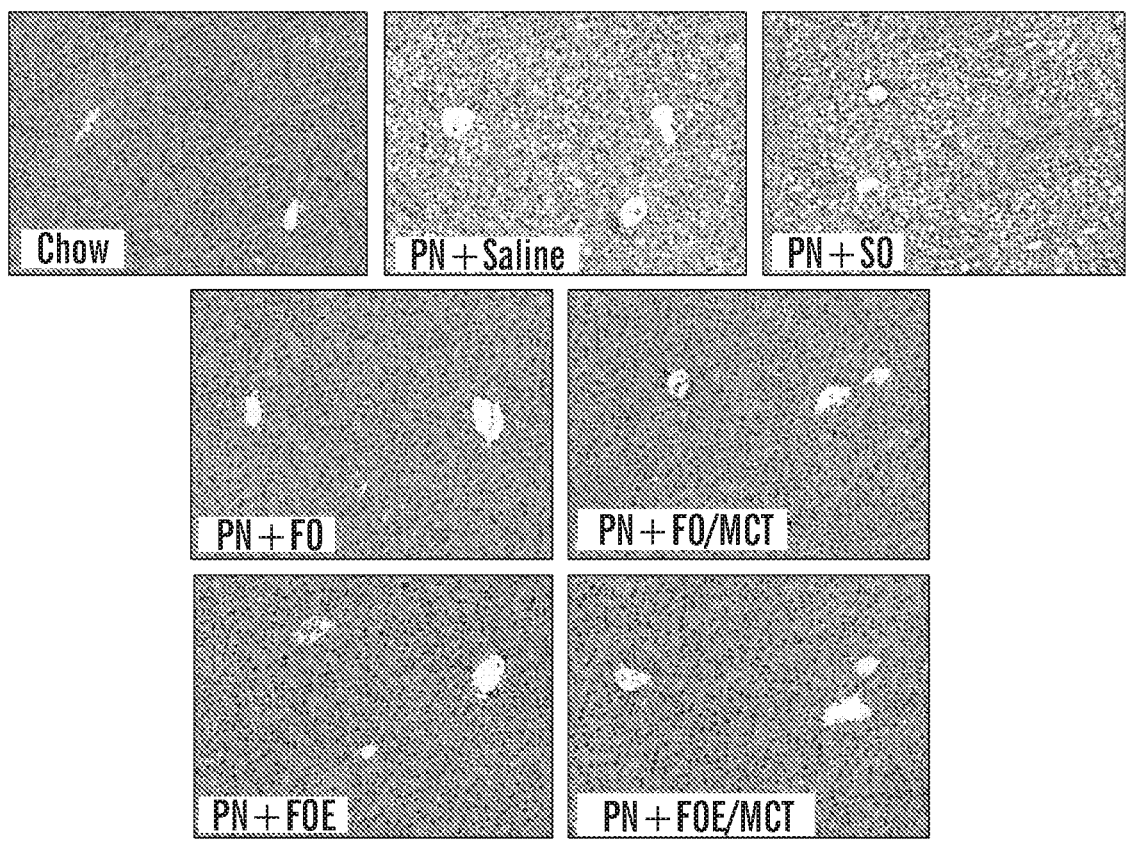
FIG. 9A depicts Hematoxylin and Eosin and FIG. 9B depicts Oil Red O analysis of livers from each treatment group. Saline and SO-treated mice developed hepatic steatosis (4A) and accumulated hepatic fat (FIG. 9B). FO, FOE, FO/MCT, and FOE/MCT preserved normal hepatic architecture (FIG. 9A), and accumulated no observable hepatic fat (FIG. 9B).
Figure 9B:
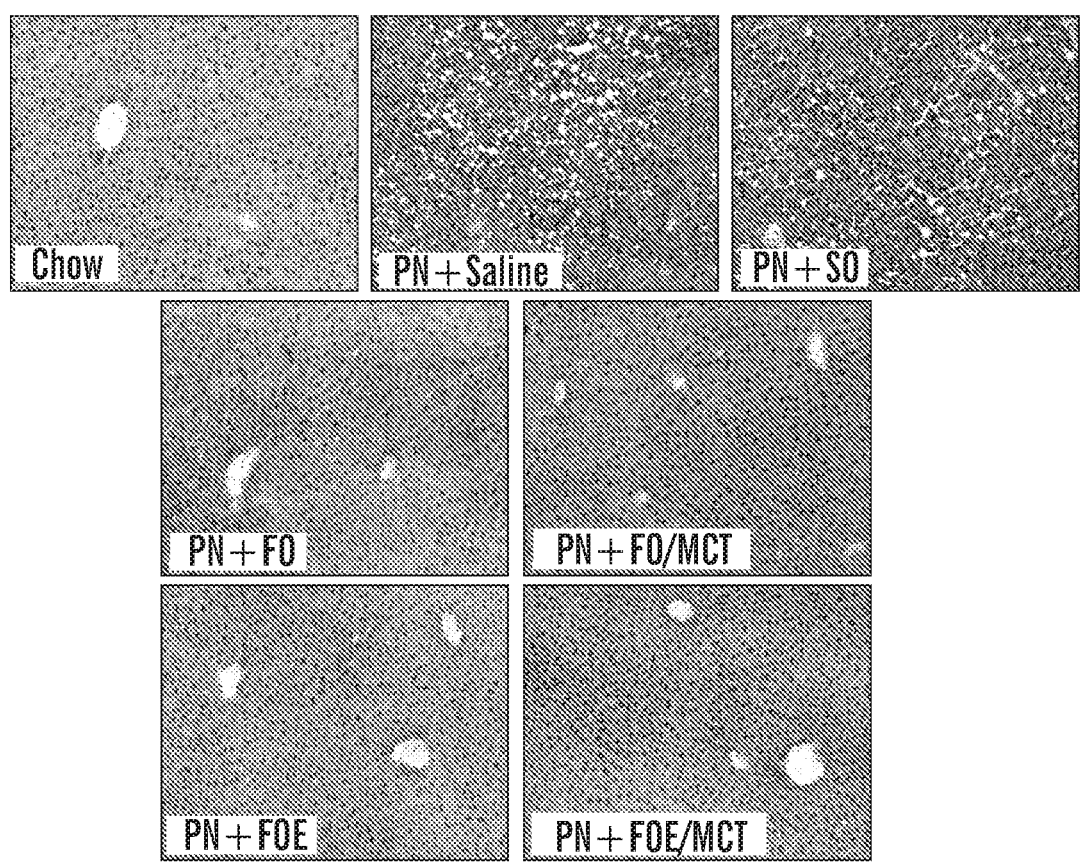

On histologic analysis, fat-free PN and PN-fed animals administered SO developed hepatosteatosis (FIG. 9A) and hepatic fat accumulation on oil red O staining (FIG. 9B). FO, FOE, FO/MCT and FOE/MCT groups preserved normal hepatic architecture similar to chow-fed controls (FIG. 9A) and had no significant hepatic fat accumulation (FIG. 9B).

Figure 10A:
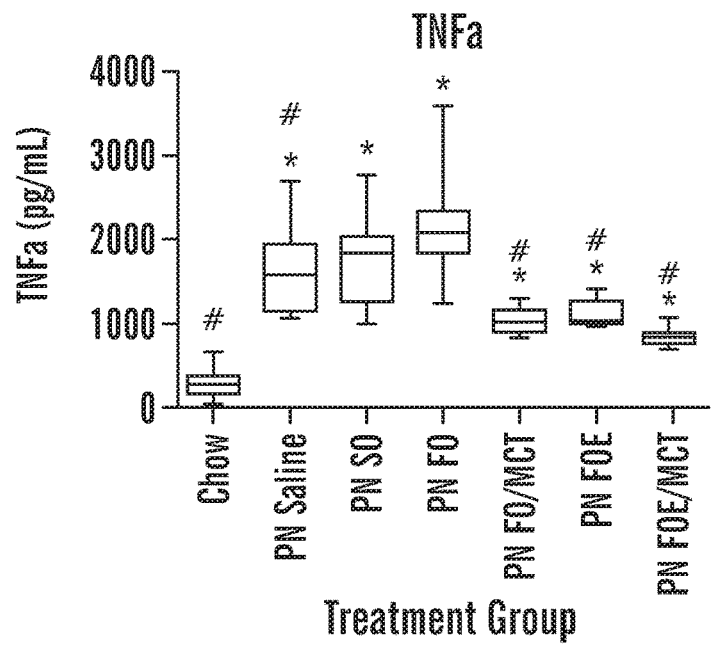
FIG. 10A depicts serum TNFa and FIG. 10B depicts serum IL-6 in LPS-treated mice. Both markers decreased compared to FO in FOE-, FO/MCT- and FOE/MCT-treated groups. There was no significant difference between FOE, FO/MCT, and FOE/MCT groups. *=p<0.003 compared to chow, and #=p<0.006 compared to FO by single-factor ANOVA.
Figure 10B:
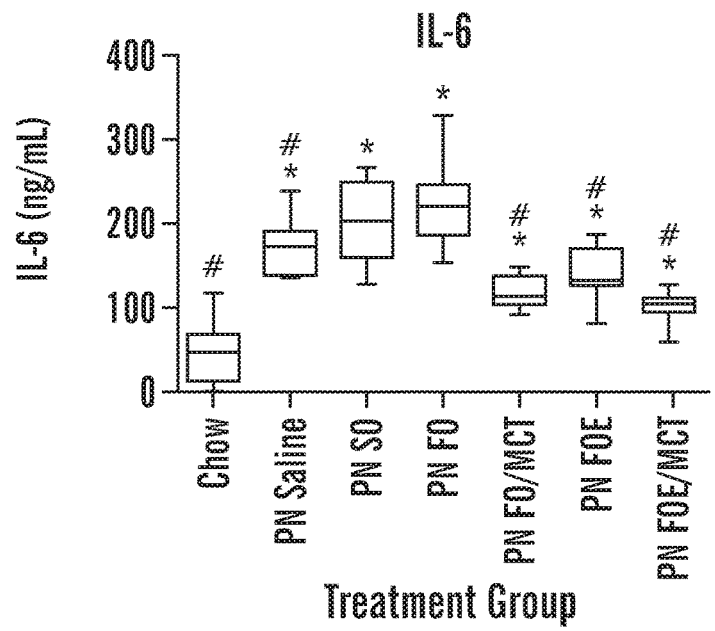

In assessment of serum TNFa and IL-6 following an LPS challenge, FOE, FO/MCT, and FOE/MCT had significantly lower levels of both markers compared to FO. There was no significant difference in levels of either of these markers between FOE, FO/MCT, and FOE/MCT groups (FIG. 10A-10B).

It is demonstrated herein that:
a. Mixed emulsion compositions of FO and MCT provide anti-inflammatory benefit in response to an inflammatory stimulus compared to FO alone. The 50:50 mixture of FO and MCT resulted in the best balance between preserved hepatic protection and blunting of the inflammatory response
b. Alpha-tocopherol added to FO results in improved anti-inflammatory benefit in response to an inflammatory stimulus compared to FO alone

TABLE 3

USP <729> Analysis of Emulsions Tested in Hypothesis 1

| Emulsion | Mean Globule Size (nm) | PFAT5 (%) |
|---|---|---|
| SO | 273.3 | 0.025 |
| FO | 238.3 | 0.033 |
| MCT | 235.4 | 0.025 |

TABLE 4

USP <729> Analysis of Emulsions Tested in Hypothesis 2

| Emulsion | Mean Globule Size (nm) | PFAT5 (%) |
|---|---|---|
| SO | 273.3 | 0.025 |
| FO | 238.3 | 0.033 |
| FOE | 235.9 | 0.013 |
| MCT | 235.4 | 0.025 |

Example 3

Parenteral nutrition-associated liver disease (PNALD) is a risk of parenteral nutrition (PN)-dependence. Intravenous soybean oil as a parenteral fat source can exacerbate the risk of developing PNALD while intravenous fish oil can stop the progression of liver disease. However, the mechanisms by which soybean oil harms and fish oil protects the liver are uncertain. Two properties that differentiate soybean oil and fish oil are α-tocopherol and phytosterol content. Soybean oil is rich in phytosterols and contains little α-tocopherol, whereas fish oil contains an abundance of α-tocopherol and only trace levels of phytosterols. This study aimed to test whether α-tocopherol confers hepatoprotective properties while phytosterols confer hepatotoxic properties to intravenous fat emulsions. Utilizing lipid emulsions formulated in the laboratory, a soybean oil emulsion (SO) was unable to protect from PN-induced hepatosteatosis in mice whereas an emulsion composition of soybean oil to which α-tocopherol had been added (SO+AT) preserved normal hepatic architecture. A fish oil emulsion (FO) and an emulsion of fish oil to which phytosterols had been added (FO+P) were both able to protect from PN-induced steatosis. Gene and protein expression of key hepatic fat-handling genes acetyl CoA carboxylase (ACC) and peroxisome proliferator-activated receptor gamma (PPARγ) were increased in animals administered SO, whereas ACC and PPARγ levels were comparable to chow-fed controls in animals receiving SO+AT, FO, and FO+P. This study demonstrates a hepatoprotective role for α-tocopherol in PN-induced liver injury and that phytosterols do not appear to compromise the hepatoprotective effects of fish oil.

Parenteral nutrition (PN) is the intravenous administration of macronutrients and micronutrients, including carbohydrates, protein in the form of amino acids, lipids, vitamins, and trace elements. PN is a critical component of therapy for patients with intestinal failure (IF) who are unable to absorb sufficient nutrients ingested orally due to inadequate intestinal length or intestinal malfunction. Although PN is life sustaining for IF patients, there are complications associated with administration of nutrition intravenously. One such complication is the development of parenteral nutrition-associated liver disease (PNALD), which is characterized by cholestatic liver disease that can progress to cirrhosis and end-stage liver disease necessitating liver transplantation. Traditionally, the progression of PNALD could only be stopped if patients could wean off PN and achieve enteral autonomy. More recently, it has been demonstrated that use of fish oil as a parenteral fat source can prevent PN-induced liver injury in animal models (1, 2) and reverse cholestasis and stop the progression of liver disease in patients with PNALD (3-9).

Fat is an important component of PN. Fat in PN is an energy-dense calorie source as well as a source of the long-chain polyunsaturated essential fatty acids (EFA), which include the omega-3 and omega-6 fatty acid families. Administration of fat-free PN requires excess carbohydrate calories to meet caloric demand. Provision of fat-free PN also results in the development of essential fatty acid deficiency (EFAD), which may be characterized by dermatitis, hair loss, developmental delay, and growth impairment (10, 11). PN-dependent patients can be biochemically monitored for EFAD through serum fatty acid profiling and measurement of the ratio of the nonessential omega-9 fatty acid mead acid, which is a triene, to the essential omega-6 fatty acid arachidonic acid, which is a tetraene. The biochemical definition of EFAD is a triene to tetraene ratio greater than 0.2 (12).

Fat in PN is administered as an oil-in-water emulsion in which the oil is dispersed as globules surrounded by a phospholipid monolayer within an aqueous medium. Globules must be small enough to travel in the circulation without causing embolic events. In the United States, the United States Pharmacopeia (USP) has set standards that intravenous fat emulsions must have a mean globule size of less than 500 nm in diameter and a percentage of fat globules greater than 5 μm in diameter (PFAT5) of no more than 0.05% (13, 14). The types and proportions of fatty acids administered are determined by the composition of the oils used to formulate the emulsion. Oils may also contain naturally occurring non-triglyceride components or additives that are incorporated into emulsions formulated with such oils.

Soybean oil-based fat emulsions are the most commonly used parenteral fat sources. In the United States, the only parenteral fat sources approved by the Food and Drug Administration (FDA) contain soybean oil. Exposure to intravenous soybean oil emulsions (SO) can exacerbate the risk of developing PNALD (15). Intravenous fish oil emulsions (FO) have been shown to prevent (1, 2) PN-induced liver injury in animal models. When administered as the sole parenteral fat source to patients who develop PNALD, FO can reverse cholestasis and stop the progression of liver disease (3-9). While the mechanisms for the hepatoprotective properties of FO and hepatotoxic properties of SO are not completely understood, there are several differences between fish oil and soybean oil that may be important contributors to the differential effects of SO and FO on the liver.

Soybean oil is naturally abundant in phytosterols, which are plant-based sterol compounds. The commercially available SO contains approximately 450 mg/L phytosterols (16). The predominant phytosterol in the commercial SO is beta-sitosterol, comprising ~70% of the total phytosterols (16). Stigmasterol and campesterol are present in smaller, but significant quantities, ~15% and ~13% respectively (16). In vitro studies have demonstrated that stigmasterol can inhibit expression of the bile acid transporter Farsenoid X Receptor (FXR) as well as genes modulated by FXR (17). In a murine model of PNALD, stigmasterol could exacerbate liver injury, suppress activation of bile acid transporters, and cause hepatic macrophage activation (18). In contrast to SO, FO contains only trace amounts of phytosterols.

Alpha-tocopherol is an anti-oxidant that is an important additive in fish oil to prevent oxidation of the long-chain polyunsaturated omega-3 fatty acids. Soybean oil contains fewer omega-3 fatty acids than fish oil and does not require the addition of α-tocopherol to maintain stability.

Figures 16, 17:
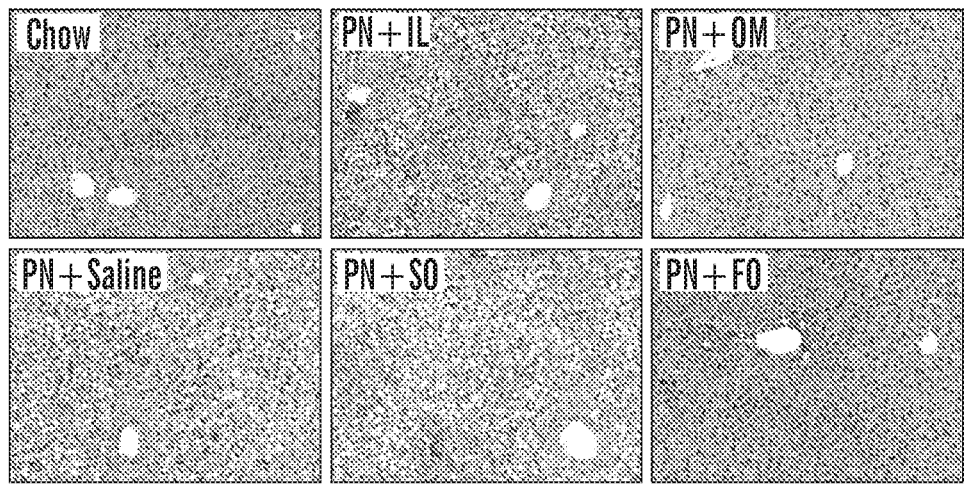

Described herein is the testing of the hypothesis that α-tocopherol contributes hepatoprotective properties and phytosterols contribute hepatotoxic properties to intravenous fat emulsions. In order to test this hypothesis, it is not possible to utilize commercially available intravenous fat emulsions, as SO and FO with varying levels of phytosterols and α-tocopherol do not exist. Therefore, emulsion compositions were formulated in the laboratory to allow for both control of the amount of α-tocopherol and phytosterols in each emulsion composition and uniformity of all emulsion components with variation in only the oil type. SO and FO formulated in the laboratory are safe and well tolerated in mice (22). FO and SO emulsions made in the laboratory have the same effects on the liver as their commercial counterparts in a murine model of PN-induced liver injury (FIG. 16). It was testd herein whether the addition of phytosteerols to fish oil renders FO hepatotoxic, and whether the addition of α-tocopherol to soybean oil renders SO hepatoprotective.

Results

Emulsion Analysis. The following oils were used to make 20% oil in water emulsions: fish oil, fish oil to which phytosterols had been added (FO+P), soybean oil, and soybean oil to which α-tocopherol had been added (SO+AT). FIG. 17 shows the phytosterol and α-tocopherol levels in the emulsions made with these oils, as well as in commercially available FO (OM) and SO (IL). Phytosterol levels in the emulsions formulated with SO, SO+AT, and FO+P were comparable. Alpha-tocopherol levels in the emulsions formulated with FO, FO+P, and SO+AT were comparable. Mean globule size and PFAT5 analysis for all emulsions met USP standards (FIG. 18).

Figure 11A:
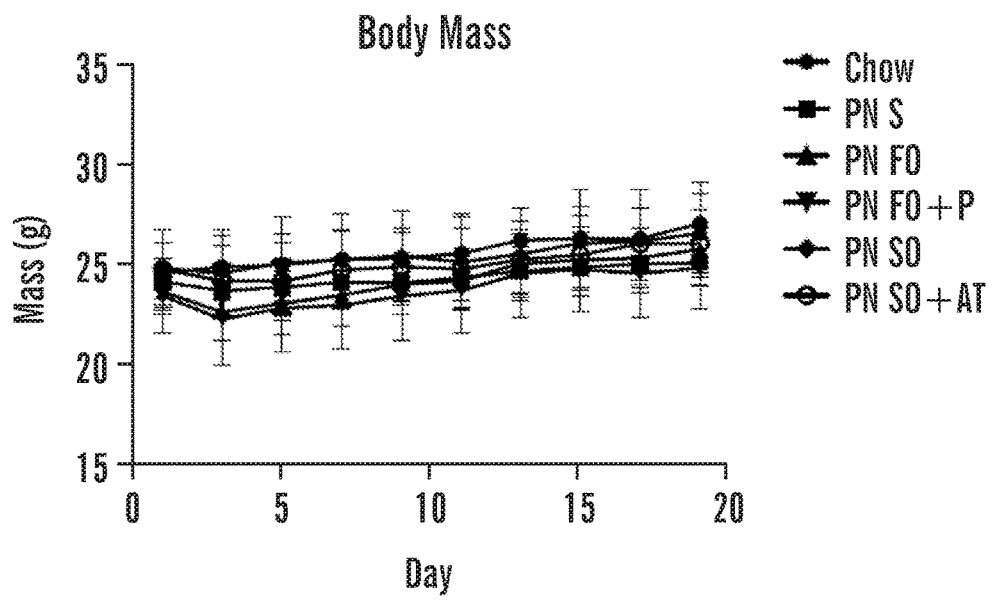
FIGS. 11A-11D demonstrate that there is no difference in growth parameters between groups administered the PN diet and administration of fat emulsions formulated in the laboratory.

Growth Parameters and Fatty Acid Profiles. There were no adverse clinical effects with administration of any of the emulsions used, and animals tolerated all emulsions well. There were no differences in growth between treatment groups (FIG. 11A).

Figure 11B:
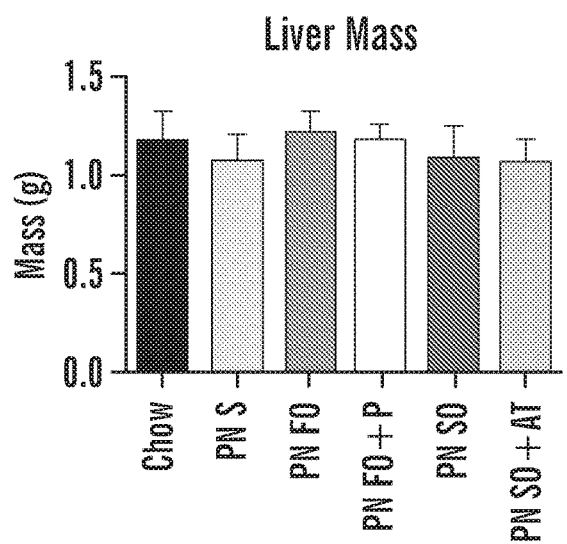
Figure 11C:
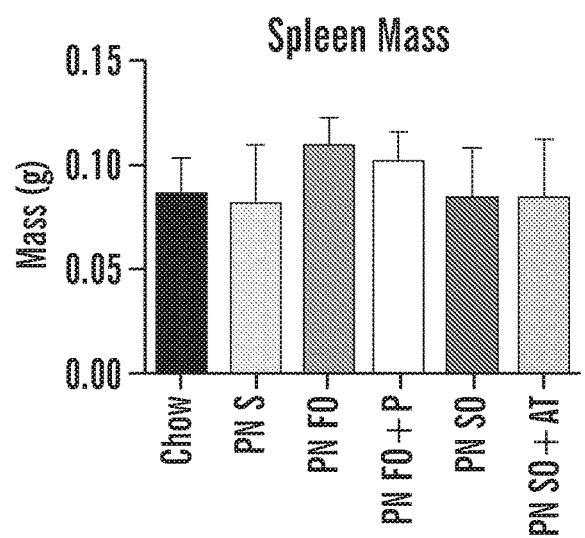
Figure 11D:
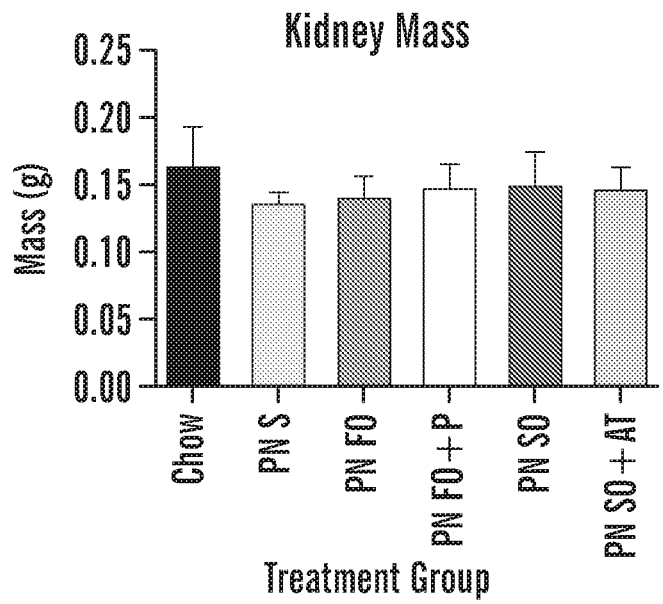

Unstable intravenous emulsions can result in organomegaly, particularly enlargement of the spleen and liver due to deposition of fat globules (23). There was no evidence of organomegaly in any of the treatment groups. Liver (FIG. 11B), spleen (FIG. 11C), and kidney (FIG. 11D) masses were similar across all treatment groups.

Figure 12A:
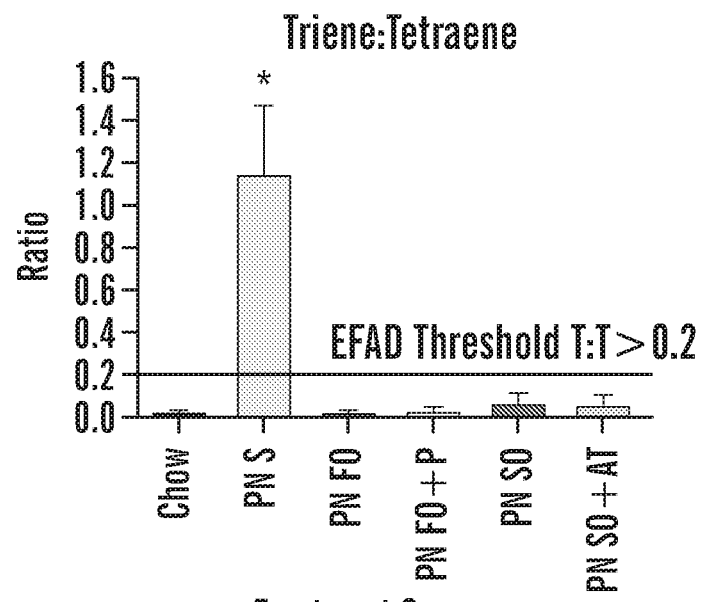
FIGS. 12A-12C depict serum fatty acid profiles after 19 days of the PN diet with administration of fat emulsions formulated in the laboratory.
Figure 12B:
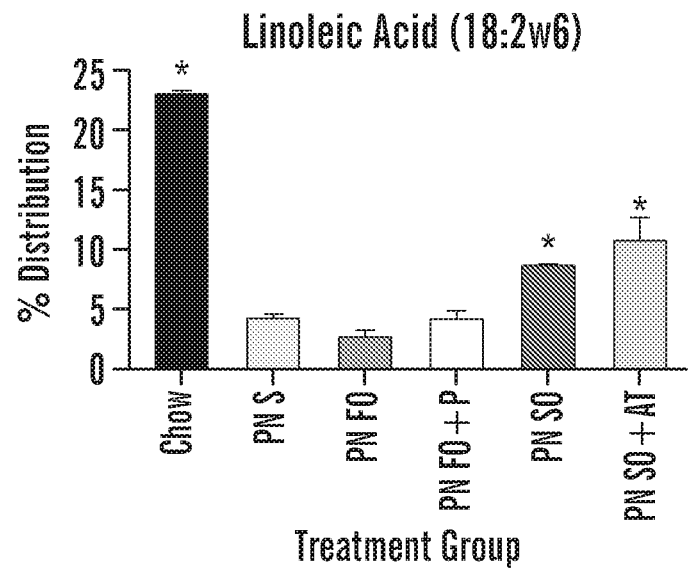
Figure 12B:
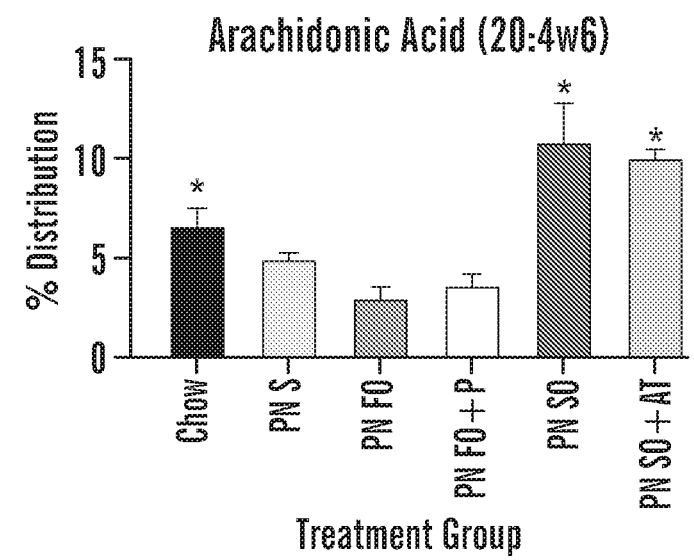
Figure 12C:
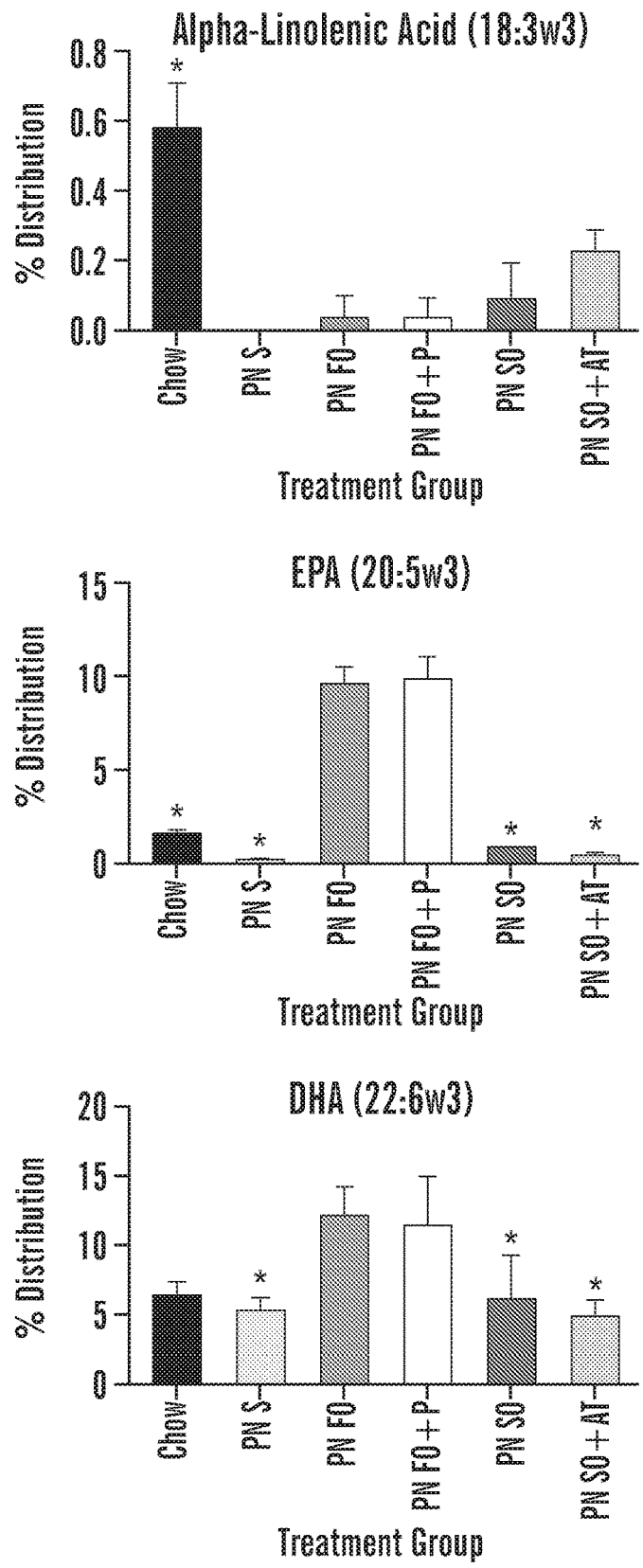

Serum fatty acid profiles were performed in order to confirm that each emulsion was able to prevent EFAD and delivered the expected complement of EFA for the oil used in the emulsion. SO is abundant in omega-6 fatty acids and contains few omega-3 fatty acids, while FO is more abundant in omega-3 fatty acids and contains a paucity of omega-6 fatty acids. These EFA balances should be reflected in the serum of animals in each respective treatment group. All emulsions prevented biochemical essential fatty acid deficiency (FIG. 12A). FO and FO+P emulsions resulted in lower serum levels of the omega-6 fatty acid arachidonic acid and higher serum levels of the omega-3 fatty acids eicosapentanoic acid (EPA) and docosahexaeonic acid (DHA) compared to the SO and SO+AT emulsions (FIGS. 12B and 12C).

Figure 13A:
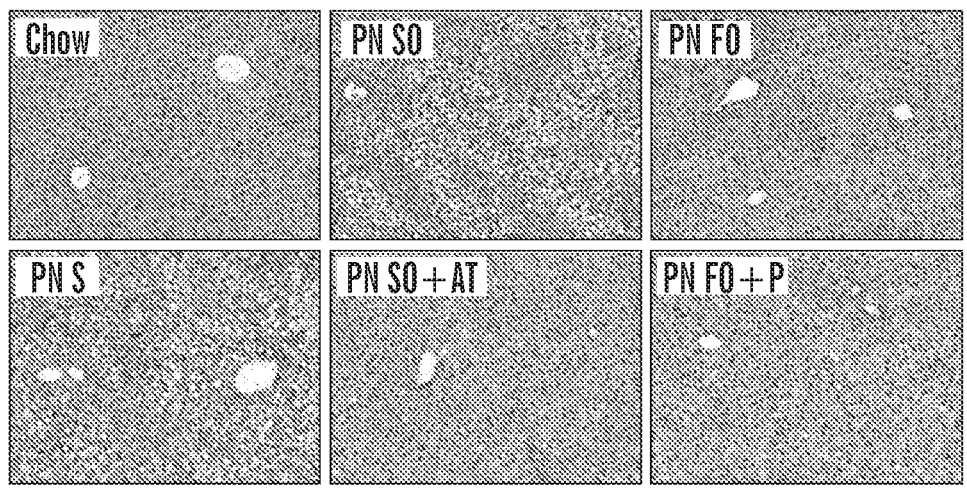
FIGS. 13A-13B depict normalization of hepatic architecture and hepatic fat accumulation with addition of α-tocopherol to SO in an intravenous fat source with the PN diet. Representative Hematoxylin and Eosin (H&E, FIG. 13A) and Oil Red O (FIG. 13B) images demonstrating hepatic architecture and hepatic fat accumulation respectively. N=10 samples per treatment group for H&E (FIG. 13A), and n=3 representative samples for Oil Red O (FIG. 13B). Images are 100× magnification (10× objective, 10× eyepiece).
Figure 13B:
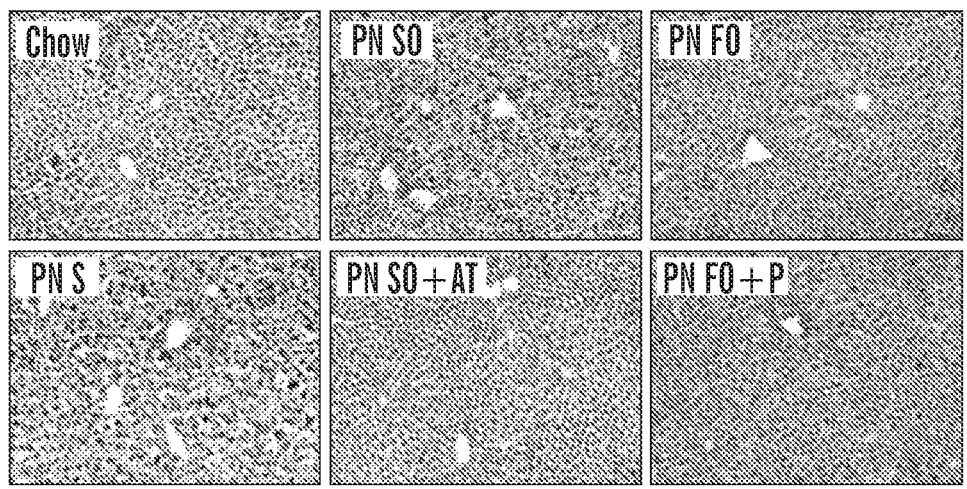

Histologic Analysis. To assess the effect of each emulsion on the development of PN-induced steatosis, livers underwent histologic analysis. SO was unable to prevent PN-induced steatosis (FIG. 13A top row, middle panel). However, addition of α-tocopherol to SO (SO+AT) resulted in preservation of normal hepatic architecture in PN-fed animals (FIG. 13A, bottom row, middle panel). FO and FO+P also preserved normal hepatic architecture (FIG. 13A, right panels) suggesting that the addition of phytosterols to FO does not compromise the ability of FO to protect the liver from PN-induced steatosis. On Oil Red O analysis to assess hepatic fat accumulation, SO+AT resulted in decreased hepatic fat accumulation compared to SO (FIG. 13B, middle panels), indicating that α-tocopherol confers hepatoprotective properties to SO. Both FO and FO+P had minimal hepatic fat accumulation, again indicating that the addition of phytosterols to FO does not compromise the hepatoprotective properties of FO (FIG. 13B, right panels).

Molecular Assessment

Figure 14A:
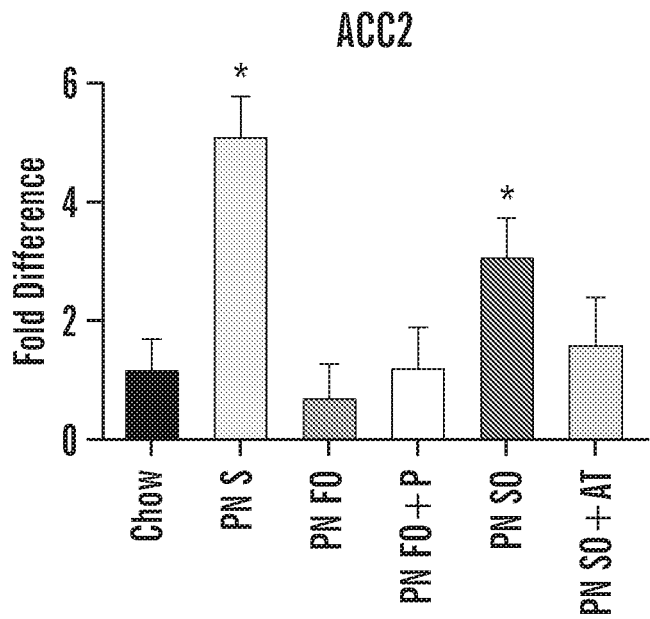
FIGS. 14A-14B depict expression of ACC (FIG. 14A) and PPARγ (FIG. 14B) is dysregulated by the fat-free PN diet and the PN diet with SO as a fat source, and normalized by FO and by the addition of α-tocopherol to SO as fat sources. Gene expression is measured as fold-difference compared to the chow-fed group. N=5 samples per treatment group, each performed in technical duplicate. Statistical analysis was with one-way ANOVA. Results are shown as the fold difference as compared to chow diet controls.
Figure 14B:
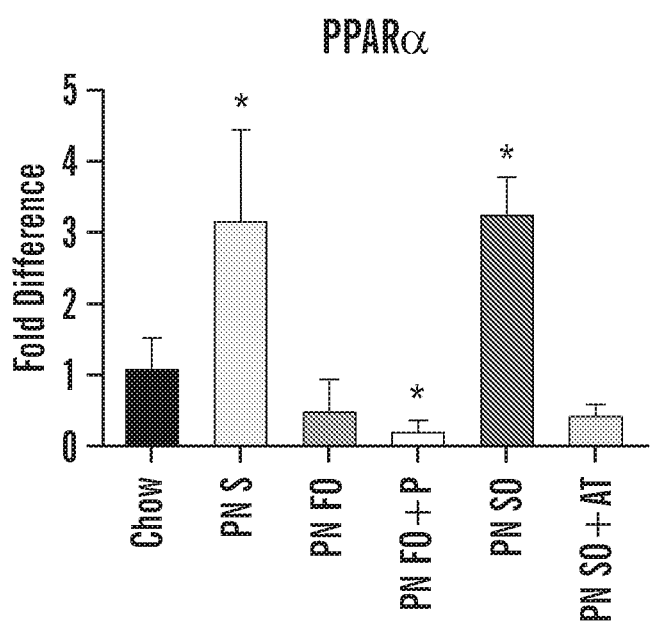
Figure 15A:
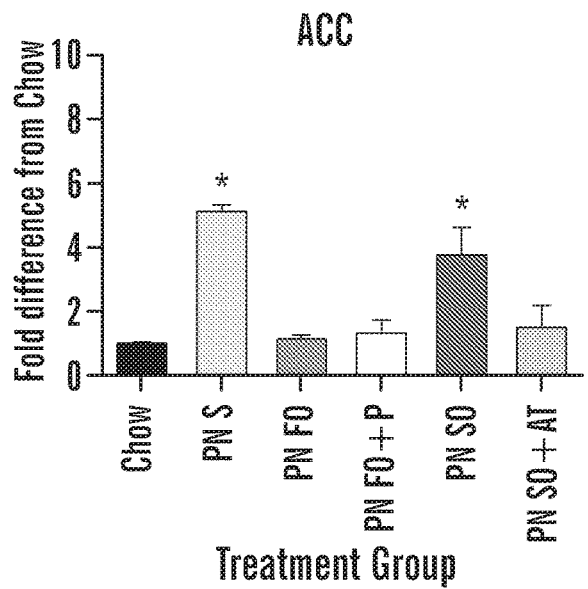
FIGS. 15A-15C depict protein levels of ACC (FIG. 15A) and PPARγ (FIG. 15B) upregulated by the fat-free PN diet and the PN diet with SO as a fat source, and normalized by FO and by the addition of α-tocopherol to SO as fat sources. Protein levels were quantified comparatively by normalizing each group to the corresponding beta-actin level and comparing to the chow-fed group. Western Blots performed in biological duplicate for each group. Statistical analysis was with one-way ANOVA.
Figure 15B:
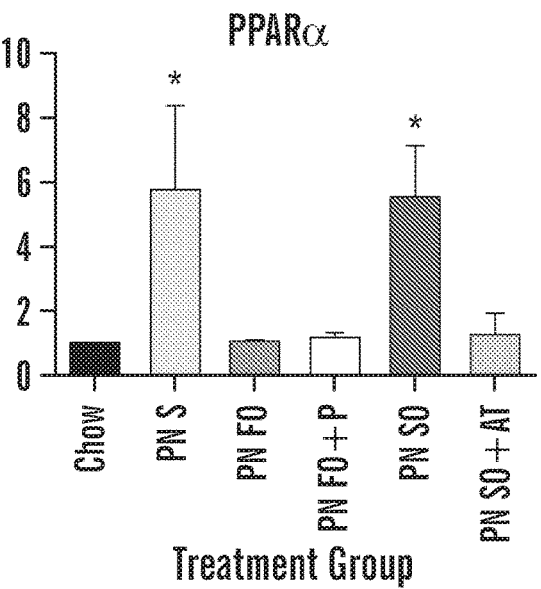
Figure 15C:
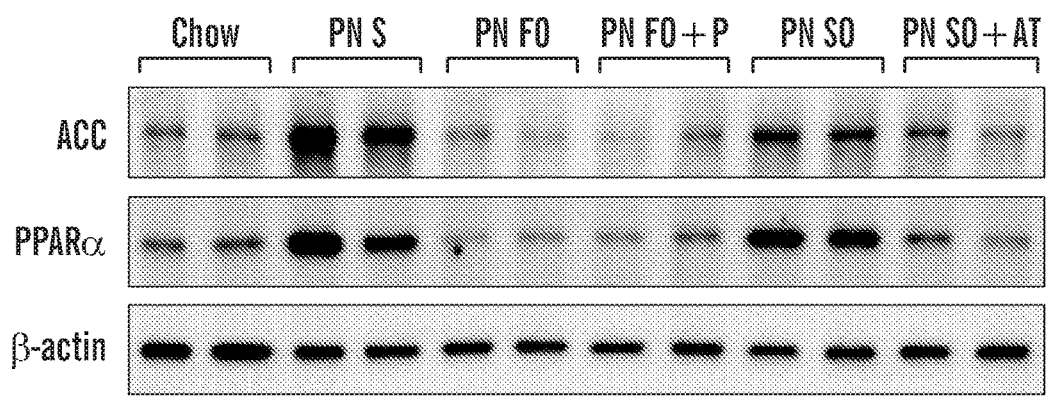

Given that mice administered the PN diet with SO as a fat source develop steatosis while those on the PN diet with FO as a fat source do not, it was hypothesized that SO and FO may differentially affect hepatic fat handling. In order to test the effect of each emulsion on hepatic fat handling, gene expression analysis of key hepatic fat-handling genes was performed. Acetyl CoA Carboxylase 2 (ACC2), which catalyzes the rate-limiting step in de novo lipogenesis, and Peroxisome Proliferator Activated Receptor-gamma (PPARγ), which is a transcriptional regulator of hepatic fat-handling were identified as genes whose expression is increased with a fat-free PN diet, is normalized by the provision of FO, but not by provision of SO (FIGS. 14A and 14B). SO+AT demonstrated normalization of ACC2 and PPARγ at the gene expression (FIGS. 14A and 14B) and protein expression (FIGS. 15A-15C) levels, indicating that the addition of α-tocopherol can impart hepatoprotective properties to SO. Both FO and FO+P resulted in normalized gene (FIGS. 14A and 14B) and protein (FIGS. 15A-15C) expression of ACC2 and PPARγ, indicating that at the molecular level, the addition of phytosterols does not compromise the hepatoprotective properties of FO.

Discussion

It has been demonstrated that serum and hepatic phytosterol levels are higher in PN-dependent patients receiving soybean oil-containing intravenous lipid emulsions than in patients who have been weaned off PN (24). Furthermore, among PN-dependent patients, levels of serum and liver phytosterols positively correlate with liver function laboratories as well as degree of portal inflammation and hepatic fibrosis on histologic analysis (24). In neonatal PN-dependent patients, serum phytosterol levels are higher in patients who meet biochemical criteria for PNALD than in those without PNALD (25). In vitro studies have shown that stigmasterol, one of the principle phytosterols in SO (16), inhibits expression of target genes of the bile acid-responsive nuclear receptor FXR (17). In contrast, Ng et al found no adverse effects on bile acid clearance with the addition of beta-sitosterol and stigmasterol to commercial FO in a preterm piglet model of PNALD (21). Studies performed by Muto et al in a neonatal piglet model of PNALD showed no improvements in bile flow, serum bile acid concentration, or serum direct bilirubin levels with the addition of α-tocopherol to a commercially available SO emulsion (26).

In this study, an intravenous lipid emulsion formulated in the laboratory using soybean oil to which α-tocopherol had been added was able to preserve normal hepatic architecture and normal expression of 2 important hepatic fat-handling genes in a murine model of PN-induced liver injury. An intravenous lipid emulsion formulated in the laboratory using soybean oil that did not contain added α-tocopherol was not able to protect from PN-induced hepatosteatosis and dysregulation of hepatic fat handling. These results are consistent with the findings of Ng et al; albeit in a different model of PN-induced liver injury utilizing intravenous lipid emulsions formulated in the laboratory. Formulation of the intravenous lipid emulsions in the laboratory allowed for control of the formulation protocol, and use of the same instruments and ingredients to ensure all emulsions used in the study were made in precisely the same way. Here, α-tocopherol was added to the soybean oil prior to formulating the emulsions, which recapitulates the process for formulating commercial FO emulsions and is the way α-tocopherol is integrated into commercially available emulsions.

This study also identified PPARγ and ACC2 as genes that are dysregulated by the PN diet, normalized by FO and α-tocopherol-containing SO, but not by SO alone. PPARγ is a transcriptional regulator of systemic and hepatic fat handling as well as inflammation. ACC encodes the enzyme that catalyzes the rate-limiting step of de novo lipogenesis. It has been demonstrated that the PPARγ agonist rosigliazone can reduce hepatic inflammation and associated biomarkers in a methionine- and choline-deficient diet mouse model of nonalcoholic steatohepatitis (27). In mice lacking the low-density lipoprotein receptor, rosiglitazone has been shown to improve high-fat diet-induced hepatosteatosis (28). Other studies have reported a positive correlation between increased PPARγ expression and the development of hepatosteatosis and accumulation of hepatic triglycerides in murine models of nonalcoholic fatty liver disease (29-31). The hepatic triglyceride-accumulating STAT5 knockout mice also exhibit reduced hepatic fat upon antagonism of PPARγ (32). In vitro studies also suggest an adipogenic effect associated with increased expression of PPARγ (33). Interestingly, it has also been shown that beta-sitosterol, one of the principle phytosterols in SO, upregulates expression of PPARγ in a rat model of radiation-induced oxidative stress (34). ACC2 expression has been shown to be upregulated in response to high-fructose conditions and normalized by treatment with the omega-3 fatty acid docosahexaenoic acid (DHA) in primary murine hepatocytes (35).

Interestingly this study did not find a hepatotoxic effect of adding phytosterols to fish oil in PN-induced liver injury. One possible conclusion is that the phytosterols in soybean oil are not responsible for the soy oil-associated hepatotoxic effects in the murine model of PN-induced liver injury. An alternative explanation is that phytosterols do have hepatotoxic properties but are unable to overcome the hepatoprotective properties of fish oil. The omega-3 fatty acids abundant in fish oil are precursors of anti-inflammatory lipid mediators (36, 37), and fish oil is also abundant in α-tocopherol. These properties may offer hepatoprotection that cannot be overcome by the presence of phytosterols. While results consistent with those in this study have been observed in a preterm piglet model of PNALD (21), other in vivo and in vitro studies suggest that phytosterols do have hepatotoxic properties (17, 18). A third possible explanation is that specific phytosterols at specific concentrations, or that a certain balance of phytosterols is required for phytosterol-associated hepatotoxic properties to occur. In this study, the composition of phytosterols added to fish oil approximated the types and amounts of phytosterols found in soybean oil.

All emulsions formulated in this study protected from the development of EFAD. Traditionally linoleic (LA) and alpha-linolenic (ALA) acids, the parent omega-6 and omega-3 fatty acids respectively, have been considered the EFAs. More recent data has suggested that provision of metabolites of LA and ALA, such as arachidonic acid (ARA), eicosapentaeonic acid (EPA), and DHA is sufficient to prevent the development of EFAD (38). Interestingly, this study found that serum ARA, EPA, and DHA reflected the balance of EFAs provided by the emulsion administered rather than serum LA and ALA levels.

The ability of α-tocopherol to render SO less hepatotoxic in a model of PN-induced liver injury implies that α-tocopherol is useful in the clinical management of PNALD and other similar hepatic pathologies. Currently FO may be used for the treatment of PNALD, however FO is not readily available to all patients. The benefits of α-tocopherol in the management of PNALD remain to be tested clinically, and it is likely that FO has additional properties, such as an abundance of omega-3 fatty acids, that make FO more beneficial than α-tocopherol alone. However, the results of this study indicate that α-tocopherol is an option in the prevention or treatment of PNALD in patients for whom FO is not available.

Experimental Procedures

Lipid Emulsion Formulation

Materials for Emulsions: Sterile water for injection (SWFI, Hospira, Lake Forest, Ill.), Egg phospholipid (Lipoid LLC, Newark, N.J.), Sodium Oleate (Lipoid LLC, Newark N.J.), and Glycerin (Sigma-Aldrich, St. Louis, Mo.) were used to formulate the dispersion. Oils used were USP-grade soybean oil (Spectrum Chemicals, New Brunswick, N.J.) and CrystalPure EPA 28/12 TG fish oil (BASF). Additives used were α-tocopherol (Sigma-Aldrich, St. Louis, Mo.), beta-sitosterol (Sigma-Aldrich, St. Louis, Mo.), and stigmasterol (Sigma-Aldrich, St. Louis, Mo.). Commercial emulsions used for analyses included Omegaven (Fresenius Kabi, Bad Homburg, Germany) and Intralipid (Fresenius Kabi, Uppsala, Sweden).

Preparation of FO+P oil: CrystalPure EPA 28/12 TG fish oil was heated to maintain temperature between 50-60° C. under constant stirring conditions. Phytosterols were added (85% beta-sitosterol, 15% stigmasterol) to a final concentration of 2.25 mg phytosterols per gram of oil and stirred until dissolved. When used to formulate a 20% emulsion, the calculated phytosterol concentration is 450 mg phytosterols per liter emulsion.

Preparation of SO+AT oil: Soybean oil was heated to maintain temperature between 50-60° C. under constant stirring conditions. Alpha-tocopherol was added to a final concentration of 1 mg α-tocopherol per gram of oil and stirred for 10-15 minutes. When used to formulate a 20% emulsion, the calculated α-tocopherol content is 200 mg α-tocopherol per liter emulsion.

Emulsion Formulation: Emulsion were formulated via high-pressure homogenization as previously described (22). All steps were performed at 40-45° C. unless otherwise specified. All steps were performed under a nitrogen atmosphere.

A dispersion was first formulated by adding frozen egg phospholipid to SWFI heated to 75-90° C. under high-speed shear mixing conditions and allowing the mixture to equilibrate at 40-45° C. Sodium oleate was added and shear mixing continued (4000-4100 RPM) for 40 minutes, after which glycerin was added. The crude dispersion was homogenized (Panda Plus Homogenizer, GEA Niro Saovi, Columbia, Md.) at 9000 psi for 20 cycles. The dispersion was filtered through a 0.45 um membrane and pH adjusted to 10.4 with 0.5N sodium hydroxide. The final dispersion was composed of 12% egg phospholipid, 25% glycerin, and 0.3% sodium oleate. One batch of dispersion was sufficient for the formulation of 5, 1-liter emulsions.

Emulsions were formulated by adding oil to an appropriate volume of dispersion under high-speed shear mixing conditions (3800-4200 RPM, adjusted to avoid foaming), with mixing continued for 40-45 minutes and slowly brought to a final volume of 500 mL with SWFI, maintaining the temperature 40-45° C. The crude emulsion was homogenized at 5000 psi for at least 9 cycles. The final emulsion was pH adjusted to 9-9.5 using 0.1N sodium hydroxide, packaged in 20 mL serum vials with head spaces flooded with nitrogen gas, and the packaged emulsions autoclaved. Final emulsion composition was 20% oil, 1.2% egg phospholipid, 2.5% glycerin, and 0.03% sodium oleate.

All emulsions underwent mean globule size and PFAT5 testing (Micro Measurements, Deerfield, Ill.) in accordance with USP <401> standards.

Determination of Phytosterol and Alpha-tocopherol Levels in Emulsions: To determine phytosterol levels, samples were saponified with 2 mol/L ethanolic KOH and sterols extracted with n-Heptane. Extracts were evaporated and separated on a capillary gas chromatography column. Detection was with flame ionization detector. Quantification was performed using epicoprostanol as an internal control.

Alpha-tocopherol levels were determined as described (39), however instead of using an internal calibration, external calibration was used.

Murine Model of PN-Induced Liver Injury. All animal experiments were approved by the Boston Children's Hospital Institutional Animal Care and Use Committee. Six week-old C57BL/6 mice (Jackson Labs, Bar Harbor, Me.) were administered either a standard chow diet or a liquid diet composed of the PN administered to patients at Boston Children's Hospital (20% Dextrose, 2% amino acids, 30 mEq/L sodium, 20 mEq/L potassium, 15 mEq/L calcium, 10 mEq/L Magnesium, 10 mMol/L phosphate, 36.67 mEq/L chloride, 19.4 mEq/L acetate, Pediatric multivitamins, Pediatric trace elements). PN-fed mice were administered intravenous (IV) saline, IV FO, IV FO+P, IV SO, or IV SO+AT (2.4 g/kg/day by tail vein injection). After 19 days, animals were euthanized by carbon dioxide asphyxiation. Blood was drawn for serum collection. Livers, spleens, and the right kidney were procured for further analysis. This experiment was performed twice with different batches of emulsions for each experiment. In the first experiment, 5 mice per treatment groups were used, and in the second experiment 10 mice per treatment group were used.

Organ Processing and Histology. Spleens, kidneys, and one portion of each liver were placed in 10% formalin and stored at 4° C. for 24 hours, then transferred to 70% ethanol. Samples were embedded in paraffin and sectioned for Hematoxylin and Eosin (H&E) staining to assess hepatic architecture. A second portion of each liver was placed in Optimum Cutting Temperature (OCT) medium (Fisher Scientific, Pittsburgh, Pa.) and frozen in liquid nitrogen. Samples underwent frozen sectioning and oil red O staining to assess hepatic fat accumulation. Visualization was with a Zeiss Axiophot™ microscope (Oberkochen, Germany). Slides were analyzed by a board-certified pathologist who was blinded to the treatment groups. A third portion of each liver was flash-frozen in liquid nitrogen and stored at −80° C. for gene and protein expression analysis.

Serum Fatty Acid Profiling. Serum fatty acid extraction was performed as previously described (2). Briefly, serum samples (30 µL per sample) with tricosanoic acid added as an internal standard underwent chloroform and methanol extraction in a ratio of 2:1 to isolate the lipid fraction. Samples were saponified with 0.5N methanolic sodium hydroxide. Samples were incubated in 14% $BF_3$/methanol for 30 minutes at 100° C. Steps were performed under nitrogen gas atmosphere to minimize oxidation. Analysis was with gas liquid chromatography (Hewlett Packard 6890) and detection was with a flame ionization detector. An external fatty acid methyl ester standard (NuCheck™ Prep, Elysian, Minn.) was used to identify sample fatty acid peaks.

Gene Expression Analysis. Livers were cut to 25 mg per sample and RNA was extracted using the Qiagen AllPrep™ DNA/RNA/Protein kit (Gaithersburg, Md.) per the manufacturer's instructions. For each reaction Taqman™ primers (Invitrogen, Carlsbad, Calif.) and reagents (Agilent Technologies, Santa Clara, Calif.) were used according to manufacturers instructions with 200 ng RNA. A 2-step cycling RT-PCR protocol was used in an ABI One Step Plus cycler. An initial reverse transcription step of 30 minutes at 50° C. and 10 minutes at 95° C. was followed by an amplification step consisting 15 seconds at 95° C. and 1 minute at 60° C. cycled 40 times. Target gene expression was normalized to the GAPDH gene and compared to the chow-fed control group using the $2^{-\Delta\Delta Ct}$ method (40).

Protein Analysis/Livers were cut to 25 mg per sample and homogenized in radioimmunoprecipitation assay (RIPA) buffer with protease inhibitor and phosphatase inhibitor using stainless steel beads in a Bullet Blender. Protein concentrations were determined using a Bradford Assay (Bio-Rad, Hercules, Calif.). Ten milligrams of protein per sample was separated using a 4-12% Bis Tris polyacrylamide gel (Invitrogen, Carlsbad, Calif.) before being transferred to a nitrocellulose membrane. Membranes were blocked in 5% non-fat milk for 1 hour. Membranes were incubated in primary antibody overnight and in secondary antibody for 1 hour. ACC and PPARγ antibodies were from Cell Signaling technologies (Danvers, Mass.). Beta-actin antibody was from Santa Cruz Biotechnologies (Paso Robles, Calif.).

REFERENCES

1. Alwayn, I. P., Gura, K., Nose, V., Zausche, B., Javid, P., Garza, J., Verbesey, J., Voss, S., Ollero, M., Andersson, C., Bistrian, B., Folkman, J., and Puder, M. (2005) Omega-3 fatty acid supplementation prevents hepatic steatosis in a murine model of nonalcoholic fatty liver disease. *Pediatr Res.* 57, 445-452
2. Meisel, J. A., Le, H. D., de Meijer, V. E., Nose, V., Gura, K. M., Mulkern, R. V, Akhavan Sharif, M. R., and Puder, M. (2011) Comparison of 5 intravenous lipid emulsions and their effects on hepatic steatosis in a murine model. *J Pediatr. Surg.* 46, 666-73
3. Diamond, I. R., Sterescu, A., Pencharz, P. B., Kim, J. H., and Wales, P. W. (2009) Changing the paradigm: omega-ven for the treatment of liver failure in pediatric short bowel syndrome. *J. Pediatr. Gastroenterol. Nutr.* 48, 209-15

4. Puder, M., Valim, C., Meisel, J. a, Le, H. D., de Meijer, V. E., Robinson, E. M., Zhou, J., Duggan, C., and Gura, K. M. (2009) Parenteral fish oil improves outcomes in patients with parenteral nutrition-associated liver injury. *Ann. Surg.* 250, 395-402
5. Gura, K. M., Duggan, C. P., Collier, S. B., Jennings, R. W., Folkman, J., Bistrian, B. R., and Puder, M. (2006) Reversal of parenteral nutrition-associated liver disease in two infants with short bowel syndrome using parenteral fish oil: implications for future management. *Pediatrics.* 118, e197-201
6. Calkins, K. L., Dunn, J. C. Y., Shew, S. B., Reyen, L., Farmer, D. G., Devaskar, S. U., and Venick, R. S. (2013) Pediatric Intestinal Failure-Associated Liver Disease Is Reversed With 6 Months of Intravenous Fish Oil. *JPEN. J Parenter. Enteral Nutr.* 38, 682-692
7. de Meijer, V. E., Gura, K. M., Le, H. D., Meisel, J. a, and Puder, M. (2009) Fish oil-based lipid emulsions prevent and reverse parenteral nutrition-associated liver disease: the Boston experience. *JPEN. J Parenter. Enteral Nutr.* 33, 541-7
8. Sorrell, M., Moreira, A., Green, K., Jacobs, R., Tragus, R., Keller, L., Quinn, A., McCurnin, D., Gong, A., El Sakka, A., Mittal, N., and Blanco, C. (2016) Favorable Outcomes of Preterm Infants with PNALD Treated with IV Fish Oil-Based Lipid Emulsion. *J. Pediatr. Gastroenterol. Nutr.* 10.1097/MPG.0000000000001397
9. Lam, H. S., Tam, Y. H., Poon, T. C. W., Cheung, H. M., Yu, X., Chan, B. P. L., Lee, K. H., Lee, B. S. C., and Ng, P. C. (2014) A Double-Blind Randomised Controlled Trial of Fish Oil-Based versus Soy-Based Lipid Preparations in the Treatment of Infants with Parenteral Nutrition-Associated Cholestasis. *Neonatology.* 105, 290-296
10. Jeppesen, P. B., Hoy, C. E., and Mortensen, P. B. (1998) Essential fatty acid deficiency in patients receiving home parenteral nutrition. *Am. J. Clin. Nutr.* 68, 126-33
11. Mascioli, E. A., Lopes, S. M., Champagne, C., and Driscoll, D. F. (1996) Essential fatty acid deficiency and home total parenteral nutrition patients. *Nutrition.* 12, 245-9
12. HOLMAN, R. T. (1960) The ratio of trienoic: tetraenoic acids in tissue lipids as a measure of essential fatty acid requirement. *J Nutr.* 70, 405-10
13. Driscoll, D. F. (2007) Globule-size distribution in injectable 20% lipid emulsions: Compliance with USP requirements. *Am. J Heal. Pharm.* 64, 2032-2036
14. Pharmacopoeia, T. U. S. (2012) Chapter 729: Globule Size Distribution in Lipid Injectable Emulsions. in *United States Pharmacopeia and National Formulary* (USP 36-NF 31), pp. 321-323
15. Teng, J., Arnell, H., Bohlin, K., Nemeth, A., and Fischler, B. (2015) Impact of parenteral fat composition on cholestasis in preterm infants *J Pediatr. Gastroenterol. Nutr.* 60, 702-7
16. Xu, Z., Harvey, K. A., Pavlina, T., Dutot, G., Hise, M., Zaloga, G. P., and Siddiqui, R. A. (2012) Steroidal compounds in commercial parenteral lipid emulsions. *Nutrients.* 4, 904-21
17. Carter, B. A., Taylor, 0. A., Prendergast, D. R., Zimmerman, T. L., Von Furstenberg, R., Moore, D. D., and Karpen, S. J. (2007) Stigmasterol, a soy lipid-derived phytosterol, is an antagonist of the bile acid nuclear receptor FXR. *Pediatr. Res.* 62, 301-6
18. El Kasmi, K. C., Anderson, A. L., Devereaux, M. W., Vue, P. M., Zhang, W., Setchell, K. D. R., Karpen, S. J., and Sokol, R. J. (2013) Phytosterols promote liver injury and Kupffer cell activation in parenteral nutrition-associated liver disease. *Sci. Transl. Med.* 5, 206ra137
19. Saboori, S., Shab-Bidar, S., Speakman, J. R., Yousefi Rad, E., and Djafarian, K. (2015) Effect of vitamin E supplementation on serum C-reactive protein level: a meta-analysis of randomized controlled trials. *Eur. J Clin. Nutr.* 10.1038/ejcn.2014.296
20. Shing, C. M., Fassett, R. G., Peake, J. M., and Coombes, J. S. (2014) Effect of tocopherol on atherosclerosis, vascular function, and inflammation in apolipoprotein E knockout mice with subtotal nephrectomy. *Cardiovasc. Ther.* 32, 270-5
21. Ng, K., Stoll, B., Chacko, S., Saenz de Pipaon, M., Lauridsen, C., Gray, M., Squires, E. J., Marini, J., Zamora, I. J., Olutoye, O. O., and Burrin, D. G. (2015) Vitamin E in New-Generation Lipid Emulsions Protects Against Parenteral Nutrition-Associated Liver Disease in Parenteral Nutrition-Fed Preterm Pigs. *JPEN. J. Parenter. Enteral Nutr.* 10.1177/0148607114567900
22. Fell, G. L., Cho, B. S., Pan, A., Nose, V., Anez-Bustillos, L., Dao, D. T., Baker, M. A., Nandivada, P., Gura, K. M., and Puder, M. (2017) A Comparison of Fish Oil Sources for Parenteral Lipid Emulsions in a Murine Model. *J. Parenter. Enter. Nutr.* 41, 181-187
23. Driscoll, D. F. (2006) Lipid injectable emulsions: Pharmacopeial and safety issues. *Pharm. Res.* 23, 1959-69
24. Hukkinen, M., Mutanen, A., Nissinen, M., Merras-Salmio, L., Gylling, H., and Pakarinen, M. P. (2016) Parenteral Plant Sterols Accumulate in the Liver Reflecting Their Increased Serum Levels and Portal Inflammation in Children With Intestinal Failure. *J Parenter. Enter. Nutr.* 10.1177/0148607116637855
25. Kurvinen, A., Nissinen, M. J., Andersson, S., Korhonen, P., Ruuska, T., Taimisto, M., Kalliomäki, M., Lehtonen, L., Sankilampi, U., Arikoski, P., Saarela, T., Miettinen, T. A., Gylling, H., and Pakarinen, M. P. (2012) Parenteral Plant Sterols and Intestinal Failure-associated Liver Disease in Neonates. *J. Pediatr. Gastroenterol. Nutr.* 54, 803-811
26. Muto, M., Lim, D., Soukvilay, A., Field, C., Wizzard, P. R., Goruk, S., Ball, R. O., Pencharz, P. B., Mi, S., Curtis, J., Wales, P. W., and Turner, J. M. (2015) Supplemental Parenteral Vitamin E Into Conventional Soybean Lipid Emulsion Does Not Prevent Parenteral Nutrition-Associated Liver Disease in Full-Term Neonatal Piglets. *J. Parenter. Enter. Nutr.* 10.1177/0148607115612030
27. Tahan, V., Eren, F., Avsar, E., Yavuz, D., Yuksel, M., Emekli, E., Imeryuz, N., Celikel, C., Uzun, H., Haklar, G., and Tozun, N. (2007) Rosiglitazone attenuates liver inflammation in a rat model of nonalcoholic steatohepatitis. *Dig. Dis. Sci.* 52, 3465-72
28. Gupte, A. A., Liu, J. Z., Ren, Y., Minze, L. J., Wiles, J. R., Collins, A. R., Lyon, C. J., Pratico, D., Finegold, M. J., Wong, S. T., Webb, P., Baxter, J. D., Moore, D. D., and Hsueh, W. A. (2010) Rosiglitazone attenuates age- and diet-associated nonalcoholic steatohepatitis in male low-density lipoprotein receptor knockout mice. *Hepatology.* 52, 2001-11
29. Bedoucha, M., Atzpodien, E., and Boelsterli, U. A. (2001) Diabetic KKAy mice exhibit increased hepatic PPARgamma1 gene expression and develop hepatic steatosis upon chronic treatment with antidiabetic thiazolidinediones. *J. Hepatol.* 35, 17-23
30. Yu, S., Matsusue, K., Kashireddy, P., Cao, W.-Q., Yeldandi, V., Yeldandi, A. V, Rao, M. S., Gonzalez, F. J., and Reddy, J. K. (2003) Adipocyte-specific gene expression and adipogenic steatosis in the mouse liver due to peroxisome proliferator-activated receptor gamma1 (PPARgamma1) overexpression. *J. Biol. Chem.* 278, 498-505

31. Jia, Y., Wu, C., Kim, J., Kim, B., and Lee, S.-J. (2016) Astaxanthin reduces hepatic lipid accumulations in high-fat-fed C57BL/6J mice via activation of peroxisome proliferator-activated receptor (PPAR) alpha and inhibition of PPAR gamma and Akt. *J. Nutr. Biochem.* 28, 9-18

32. Hosui, A., Tatsumi, T., Hikita, H., Saito, Y., Hiramatsu, N., Tsujii, M., Hennighausen, L., and Takehara, T. (2016) Signal transducer and activator of transcription 5 plays a crucial role in hepatic lipid metabolism through regulation of CD36 expression. *Hepatol. Res.* 10.1111/hepr.12816

33. Maruyama, H., Kiyono, S., Kondo, T., Sekimoto, T., and Yokosuka, O. (2016) Palmitate-induced Regulation of PPARγ via PGC1α: a Mechanism for Lipid Accumulation in the Liver in Nonalcoholic Fatty Liver Disease. *Int. J. Med. Sci.* 13, 169-178

34. Moustafa, E. M., and Thabet, N. M. (2017) Beta-sitosterol upregulated paraoxonase-1 via peroxisome proliferator-activated receptor-γ in irradiated rats. *Can. J. Physiol. Pharmacol.* 10.1139/cjpp-2016-0397

35. Zheng, J., Peng, C., Ai, Y., Wang, H., Xiao, X., and Li, J. (2016) Docosahexaenoic Acid Ameliorates Fructose-Induced Hepatic Steatosis Involving ER Stress Response in Primary Mouse Hepatocytes. *Nutrients.* 8, 55

36. Kalish, B. T., Le, H. D., Fitzgerald, J. M., Wang, S., Seamon, K., Gura, K. M., Gronert, K., and Puder, M. (2013) Intravenous fish oil lipid emulsion promotes a shift toward anti-inflammatory proresolving lipid mediators. *Am. J. Physiol. Gastrointest. Liver Physiol.* 305, G818-28

37. Bagga, D., Wang, L., Farias-Eisner, R., Glaspy, J. a, and Reddy, S. T. (2003) Differential effects of prostaglandin derived from omega-6 and omega-3 polyunsaturated fatty acids on COX-2 expression and IL-6 secretion. *Proc. Natl. Acad. Sci. U.S.A.* 100, 1751-6

38. Le, H. D., Meisel, J. A., de Meijer, V. E., Fallon, E. M., Gura, K. M., Nose, V., Bistrian, B. R., and Puder, M. (2012) Docosahexaenoic Acid and Arachidonic Acid Prevent Essential Fatty Acid Deficiency and Hepatic Steatosis. *J. Parenter. Enter. Nutr.* 36, 431-441

39. Xu, Z., Harvey, K. A., Pavlina, T. M., Zaloga, G. P., and Siddiqui, R. A. (2015) Tocopherol and tocotrienol homologs in parenteral lipid emulsions. *Eur. J. Lipid Sci. Technol.* 117, 15-22

40. Schmittgen, T. D., and Livak, K. J. (2008) Analyzing real-time PCR data by the comparative CT method. *Nat. Protoc.* 3, 1101-1108

Example 4

In Examples 1-3, the oil emulsion composition mixtures were prepared as follows: Oil-in-water emulsions of the desired concentration were developed using the Panda Plus GEA Niro Soavi™. Using a high Silverson high shear mixer, phospholipidwas dispersed while still frozen in a volume of water for injection, previously heated to 100 degrees Celsius, equal to approximately 3 times the weight of the oil. Sodium Oleate was then added and dissolved with the mixing until it was finely divided and formed a viscous fluid. Glycerin was then added to the dispersion and mixed using the Silverson high shear mixer until uniform at a rate of 3000 rpm for 10 minutes. This solution was then passed through the Panda Plus GEA Niro Soavi™ homogenizer set at 500 psi (2nd stage) and 4500 psi (1st stage) for a total pressure of 5000 psi (+ or −400 psi) on a recirculation basis for a time equivalent to 10 complete passes of this volume of dispersion through the homogenizer. The temperature of the dispersion was maintained around 40 degrees Celsius throughout this process. Afterwards, the pH was recorded and adjusted to 10.2 to 10.8 at 40 degrees C. (range 38-42 degrees Celsius) with 0.5 Normal sodium hHydroxide solution. Oil was heated to approximately 40 degrees Celsius under nitrogen atmosphere, and added in a thin stream to the pH adjusted dispersion with approximately 200 mL water for injection (heated to 100 deg Celsius) using the Silverson high shear mixer and mixed at 3000 rpm for a total of 10 minutes, then at 4000 rpm for a total of 5 minutes. Water for injection (heated to 100 deg Celsius) was then added to the crude emulsion concentrate to 100% of the volume of the final emulsion. The diluted emulsion was then added to the Panda Plus GEA Niro Soavi™ hopper and was passed through the homogenizer at 900 psi (2nd stage) and 8100 psi (1st stage) for a total pressure of 9000 psi (pressure ratio is 1:10 2nd stage to 1st stage) for a time not less than that required for 9 consecutive complete passes. The emulsion in the hopper was in continuous circulation with a Heidolph RZR 2020™ mixer set at a power of 1 and a speed of 8. The temperature of the emulsion was kept steady around 40 degrees with a Thermo Cube™ water chiller set to 38 degrees Celsius. After the 9th pass, the emulsion was transferred to a clean glass container. The pH was recorded at 40 degrees Celsius (range 38-40 degrees Celsius) and adjusted to 9 (range 8.8-9.2) with 0.1 Normal sodium hydroxide solution. All components of this emulsion were maintained under a nitrogen gas atmosphere in the headspace of all vessels during manufacture. Vessels were made of 316 grade stainless steel containers. After pH adjustment, the emulsion was transferred to sterile washed vials for storage, autoclaved for 15 minutes, and stored in the refrigerator, not exceeding 30 degrees Celsius.

In embodiments where combinations of MCT, FO, and/or SO were utilized, emulsions of the indicated oil were prepared as in the preceding paragraph at a concentration of 20% w/v in water. These emulsions were then blended together to yield different ratios. For example, 100 mL of a 50:50 MCT:FO emulsion composition was prepared by blending 50 mL of a 20% MCT emulsion and 50 mL of a 20% FO emulsion. In this way, the final emulsion compositions were 20% total fat/volume.

What is claimed herein is:

1. An emulsion composition comprising:
   fish oil and medium-chain triglycerides (MCT) at a ratio between, but not inclusive of, 30:70 to about 70:30; or
   omega-3 fatty acids and medium-chain triglycerides (MCT) at a ratio of about 30:70 to about 70:30;
   wherein the total triglyceride+diglyceride content of the fish oil and/or omega-3 fatty acids comprises no more than 10% diglyceride.

2. The emulsion composition of claim 1, comprising:
   fish oil and medium-chain triglycerides (MCT) at a ratio of about 40:60 to about 60:40; or
   omega-3 fatty acids and medium-chain triglycerides (MCT) at a ratio of about 40:60 to about 60:40.

3. The emulsion composition of claim 1, comprising
   fish oil and medium-chain triglycerides (MCT) at a ratio of about 50:50; or
   omega-3 fatty acids and medium-chain triglycerides (MCT) at a ratio of about 50:50.

4. The emulsion composition of claim 1, wherein the composition further comprises alpha-tocopherol.

5. The emulsion composition of claim 4, wherein the alpha-tocopherol is present at a level of at least 100 mg per liter of the emulsion composition.

6. The emulsion composition of claim 1, wherein the fish oil and medium-chain triglycerides (MCT) or omega-3 fatty acids and medium-chain triglycerides (MCT) comprise phytosterols.

7. The emulsion composition of claim 1, wherein the fish oil and medium-chain triglycerides (MCT) or omega-3 fatty acids and medium-chain triglycerides (MCT) comprise phytosterols at a concentration of less than 50 mg per liter of the emulsion composition.

8. The emulsion composition of claim 1, wherein the fish oil and medium-chain triglycerides (MCT) or omega-3 fatty acids and medium-chain triglycerides (MCT) comprise arachidonic acid at a concentration of at least 900 mg/L of the emulsion composition.

9. The emulsion composition of claim 1, wherein the fish oil and medium-chain triglycerides (MCT) or omega-3 fatty acids and medium-chain triglycerides (MCT) comprise docosahexaenoic acid at a concentration of at least 13.4 grams/L of the emulsion composition.

10. The emulsion composition of claim 1, wherein the fish oil and medium-chain triglycerides (MCT) or omega-3 fatty acids and medium-chain triglycerides (MCT) comprise eicosapentaenoic acid at a concentration of at least 11.6 grams/L of the emulsion composition.

11. The emulsion composition of claim 1, wherein the composition comprises a mixture of an emulsion of a fish oil and/or omega-3 fatty acid oil and an emulsion of MCT.

12. The emulsion composition of claim 1, wherein the composition comprises an emulsion of a mixture of a fish oil and/or omega-3 fatty acid oil and an MCT.

13. The emulsion composition of claim 1, wherein the fish oil and/or omega-3 fatty acid oil have not been distilled or re-esterified.

14. The emulsion composition of claim 1, formulated for parenteral or intravenous administration.

15. The emulsion composition of claim 1, further comprising an additive of one or more additional fatty acids or a mixture thereof.

16. The emulsion composition of claim 15, wherein the composition comprises a mixture of a) an emulsion of the additive and b) one or more emulsions of i) the fish oil and/or omega-3 fatty acids and ii) the MCT.

17. The emulsion composition of claim 1, further comprising one or more of egg phospholipid, glycerin, sodium oleate, and sodium hydroxide.

18. A method comprising administering an emulsion composition of claim 1 to a subject.

19. The method of claim 18, wherein the patient is a patient in need of treatment for a condition selected from the group consisting of: hepatic steatosis; intestinal failure; parenteral nutrition-associated liver disease (PNALD); sepsis; cystic fibrosis; sickle cell anemia; pancreatitis; inflammatory bowel disease; Crohn's disease; biliary atresia; primary sclerosis cholangitis; an inflammatory infection; an inflammatory condition; systemic inflammatory response syndrome (SIRS); hypertriglyceridemia; severe hypertriglyceridemia; severe hepatic steatosis; retinopathy of prematurity; acute tubular necrosis; IgA nephropathies; ischemia-reperfusion injury; traumatic brain injury; multisystem organ failure; respiratory distress syndrome; acute myocardial infarction; myocardial infarction; status *anginosus*; status asthmaticus; status epilepticus; status lacunaris; inflammatory bowel disease; regional enteritis; ulcerative colitis; severe or debilitating arthritis; arthritis; psoriasis; severe psoriasis; burns; third degree burns; pancreatitis; acute pancreatitis; intestinal failure associated liver disease (IFALD), parenteral nutrition associated cholestasis (PNAC), essential fatty acid deficiency (EFAD), parenteral nutrition dependency complicated by soy allergy or allergy to lipid emulsions comprising ingredients other than MCTs and fish oil, omega-3 predominate fatty acid oil, and/or omega-3 fatty acids.

20. The method of claim 18, wherein the administration is chronic.

21. The emulsion formulation of claim 1, wherein the fish oil and medium-chain triglycerides (MCT) or omega-3 fatty acids and medium-chain triglycerides (MCT) comprise phytosterols or omega-6 fatty acids at a concentration of less than 100 mg/L of the emulsion composition.

22. The emulsion composition of claim 1, wherein the omega-3 fatty acids are provided as an omega-3 predominate fatty acid oil which has not undergone re-esterification.

23. The emulsion composition of claim 1, wherein the fish oil and/or omega-3 fatty acids comprise no diglycerides.

24. The emulsion composition of claim 1, wherein the composition comprises a) the fish oil and the MCT at a concentration of 10 g to 50 g per 100 mL or b) the omega-3 fatty acids and the MCT at a concentration of 10 g to 50 g per 100 mL.

25. The emulsion composition of claim 1, wherein the fish oil and medium-chain triglycerides (MCT) or omega-3 fatty acids and medium-chain triglycerides (MCT) comprise omega-6 fatty acids at a concentration of less than 100 mg/mL of the emulsion composition.

26. The emulsion composition of claim 1, wherein the fish oil and medium-chain triglycerides (MCT) or omega-3 fatty acids and medium-chain triglycerides (MCT) comprise omega-6 fatty acids at a concentration of less than 50 mg/mL of the emulsion composition.

* * * * *

UNITED STATES PATENT AND TRADEMARK OFFICE
CERTIFICATE OF CORRECTION

PATENT NO. : 11,324,697 B2
APPLICATION NO. : 16/634194
DATED : May 10, 2022
INVENTOR(S) : Mark Puder et al.

It is certified that error appears in the above-identified patent and that said Letters Patent is hereby corrected as shown below:

In the Claims

At Column 62, Lines 40-49:
"25. The emulsion composition of claim 1, wherein the fish oil and medium-chain triglycerides (MCT) or omega-3 fatty acids and medium-chain triglycerides (MCT) comprise omega-6 fatty acids at a concentration of less than 100 mg/mL of the emulsion composition.

26. The emulsion composition of claim 1, wherein the fish oil and medium-chain triglycerides (MCT) or omega-3 fatty acids and medium-chain triglycerides (MCT) comprise omega-6 fatty acids at a concentration of less than 50 mg/mL of the emulsion composition."

Should be replaced with:
— 25. The emulsion composition of claim 1, wherein the fish oil and medium-chain triglycerides (MCT) or omega-3 fatty acids and medium-chain triglycerides (MCT) comprise omega-6 fatty acids at a concentration of less than 100 mg/L of the emulsion composition.

26. The emulsion composition of claim 1, wherein the fish oil and medium-chain triglycerides (MCT) or omega-3 fatty acids and medium-chain triglycerides (MCT) comprise omega-6 fatty acids at a concentration of less than 50 mg/L of the emulsion composition. —.

Signed and Sealed this
Thirteenth Day of December, 2022

*Katherine Kelly Vidal*
Katherine Kelly Vidal
*Director of the United States Patent and Trademark Office*